(12) United States Patent
Fehr Pereira Lopes

(10) Patent No.: US 10,328,155 B2
(45) Date of Patent: *Jun. 25, 2019

(54) COMPOSITIONS OF JASMONATE COMPOUNDS AND METHODS OF USE

(71) Applicant: Nanocare Technologies, Inc., New York, NY (US)

(72) Inventor: Jose E. Fehr Pereira Lopes, Sao Carlos (BR)

(73) Assignee: NANOCARE TECHNOLOGIES, INC., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/433,581

(22) Filed: Feb. 15, 2017

(65) Prior Publication Data

US 2018/0000958 A1 Jan. 4, 2018

Related U.S. Application Data

(63) Continuation of application No. 14/525,199, filed on Oct. 27, 2014, now Pat. No. 9,592,305, which is a
(Continued)

(51) Int. Cl.
*A61K 47/61* (2017.01)
*A61K 9/00* (2006.01)
(Continued)

(52) U.S. Cl.
CPC ............ *A61K 47/61* (2017.08); *A61K 9/0017* (2013.01); *A61K 9/0051* (2013.01);
(Continued)

(58) Field of Classification Search
CPC ................ A61K 47/61; A61K 47/6911; A61K 47/6951; A61K 9/1075; C08L 5/08
See application file for complete search history.

(56) References Cited

U.S. PATENT DOCUMENTS

| 5,662,932 A | 9/1997 | Amselem et al. |
| 6,469,061 B1 | 10/2002 | Flescher et al. |
| (Continued) | | |

FOREIGN PATENT DOCUMENTS

| BR | PI0604024-1 A | 4/2008 |
| CA | 2630666 A1 | 6/2007 |
| (Continued) | | |

OTHER PUBLICATIONS

"Gum Arabic," American Heritage Science Dictionary. 2009 [Online], Nov. 6, 2013. Retrieved from the Internet: <URL: http://www.thefreedictionary.com/Acacia+gum>.
(Continued)

*Primary Examiner* — Carlos A Azpuru
(74) *Attorney, Agent, or Firm* — Cooley LLP

(57) ABSTRACT

The disclosure describes nanocarried and/or microcarried jasmonate compounds and their pharmaceutical compositions, as well as use thereof for treating or preventing angiogenesis-related or NF-κB-related disorders. Also disclosed are methods of making the nanocarried and/or microcarried compounds and their compositions.

11 Claims, 45 Drawing Sheets

Related U.S. Application Data continuation of application No. 13/621,570, filed on Sep. 17, 2012, now Pat. No. 8,883,220.

(60) Provisional application No. 61/612,774, filed on Mar. 19, 2012, provisional application No. 61/607,318, filed on Mar. 6, 2012, provisional application No. 61/603,042, filed on Feb. 24, 2012, provisional application No. 61/555,690, filed on Nov. 4, 2011, provisional application No. 61/535,836, filed on Sep. 16, 2011.

(51) Int. Cl.

| | | |
|---|---|---|
| *A61K 31/5578* | (2006.01) | |
| *A61K 31/573* | (2006.01) | |
| *A61K 31/19* | (2006.01) | |
| *A61K 31/215* | (2006.01) | |
| *A61K 47/08* | (2006.01) | |
| *A61K 47/24* | (2006.01) | |
| *A61K 9/107* | (2006.01) | |
| *A61K 9/127* | (2006.01) | |
| *A61K 9/51* | (2006.01) | |
| *C08B 37/08* | (2006.01) | |
| *C08L 5/08* | (2006.01) | |
| *C08L 101/00* | (2006.01) | |
| *A61K 47/69* | (2017.01) | |

(52) U.S. Cl.
CPC ............ *A61K 9/1075* (2013.01); *A61K 9/127* (2013.01); *A61K 9/5123* (2013.01); *A61K 9/5153* (2013.01); *A61K 9/5161* (2013.01); *A61K 31/19* (2013.01); *A61K 31/215* (2013.01); *A61K 31/5578* (2013.01); *A61K 31/573* (2013.01); *A61K 47/08* (2013.01); *A61K 47/24* (2013.01); *A61K 47/6911* (2017.08); *A61K 47/6939* (2017.08); *A61K 47/6951* (2017.08); *C08B 37/003* (2013.01); *C08L 5/08* (2013.01); *C08L 101/005* (2013.01); *C08L 2205/18* (2013.01)

(56) References Cited

U.S. PATENT DOCUMENTS

| | | | |
|---|---|---|---|
| 6,790,815 | B1 | 9/2004 | Bettiol et al. |
| 7,425,651 | B2 | 9/2008 | Flescher et al. |
| 7,683,211 | B2 | 3/2010 | Flescher et al. |
| 8,883,220 | B2 * | 11/2014 | Fehr Pereira Lopes ............. A61K 31/19 424/499 |
| 9,592,305 | B2 * | 3/2017 | Fehr Pereira Lopes ............. A61K 31/19 |
| 2002/0173470 | A1 | 11/2002 | Flescher et al. |
| 2003/0224024 | A1 | 12/2003 | Leveque et al. |
| 2004/0209795 | A1 | 10/2004 | Vlad |
| 2008/0044364 | A1 | 2/2008 | Carola et al. |
| 2009/0098200 | A1 | 4/2009 | Temtsin Krayz et al. |
| 2009/0133166 | A1 | 5/2009 | Scheer et al. |
| 2009/0197939 | A1 | 8/2009 | Walke et al. |
| 2009/0291904 | A1 | 11/2009 | Kashman et al. |
| 2010/0160623 | A1 | 6/2010 | Strassburger |
| 2011/0305731 | A1 | 12/2011 | Lopes |
| 2013/0089615 | A1 | 4/2013 | Lopes |
| 2013/0203828 | A1 | 8/2013 | Chen et al. |
| 2013/0338120 | A1 | 12/2013 | Sang |
| 2014/0220132 | A1 | 8/2014 | Lopes |
| 2015/0140110 | A1 | 5/2015 | Lopes |
| 2016/0354312 | A1 | 12/2016 | Lopes |
| 2017/0368186 | A1 | 12/2017 | Lopes |

FOREIGN PATENT DOCUMENTS

| | | |
|---|---|---|
| CN | 1054605 A | 9/1991 |
| CN | 101818100 A | 9/2010 |
| EP | 0392608 A2 | 10/1990 |
| EP | 1379229 B1 | 2/2007 |
| EP | 1814894 A2 | 8/2007 |
| JP | 10-059829 A | 3/1998 |
| JP | 3568325 B2 | 9/2004 |
| WO | WO 1998/056340 A1 | 12/1998 |
| WO | WO 2001/002589 | 1/2001 |
| WO | WO 2002/072011 A2 | 9/2002 |
| WO | WO 2002/080890 A2 | 10/2002 |
| WO | WO 2006/028311 A1 | 3/2006 |
| WO | WO 2006/056308 A2 | 6/2006 |
| WO | WO 2006/068665 A1 | 6/2006 |
| WO | WO 2007/010080 A2 | 1/2007 |
| WO | WO 2007/066336 | 6/2007 |
| WO | WO 2007/066337 | 6/2007 |
| WO | WO 2007/103336 A2 | 9/2007 |
| WO | WO 2007/145663 A1 | 12/2007 |
| WO | WO 2008/007367 A1 | 1/2008 |
| WO | WO 2008/083213 A2 | 7/2008 |
| WO | WO 2009/019693 A2 | 2/2009 |
| WO | WO 2009/060165 A2 | 5/2009 |
| WO | WO 2009/106662 A1 | 9/2009 |
| WO | WO 2010/006392 A2 | 1/2010 |
| WO | WO 2010/143180 A1 | 12/2010 |
| WO | WO 2012/114196 A1 | 8/2012 |
| WO | WO 2013/040556 A1 | 3/2013 |
| WO | WO 2013/056754 A1 | 4/2013 |
| WO | WO 2014/009429 | 1/2014 |

OTHER PUBLICATIONS

Costantini, P. et al., "Mitochondrion as a Novel Target of Anticancer Chemotherapy," Journal of the National Cancer Institute, vol. 92, No. 13, Jul. 5, 2000, pp. 1042-1053.

Dias, M. L. N. et al., "Pharmacokinetics and tumor uptake of a derivatized form of paclitaxel associated to a cholesterol-rich nanoemulsion (LDE) in patients with gynecologic cancers," Cancer Chemother Pharmacol (2007) 59:105-111.

Drumond, W. S. et al., "Synthesis and Characterization of Poly(lactic acid-b-ethylene glycol) Copolymer," Polímeros: Ciência e Tecnologia, vol. 14, No. 2, (2004), pp. 74-79 (with English Abstract).

Favero, G. M. et al., "Synthetic nanoemulsion resembling a protein-free model of 7-ketocholesterol containing low density lipoprotein: in vitro and in vivo studies," Biol. Res., 43:439-444 (2010).

Fingrut, O. et al., "Jasmonates Induce Nonapoptotic Death in High-Resistance Mutant p53-Expressing B-Lymphoma Cells," Brit. J. Pharmacol., 146 (2005) pp. 800-808.

Fingrut, O. et al., "Plant Stress Hormones Suppress the Proliferation and Induce Apoptosis in Human Cancer Cells," Leukemia, 16 (2002) pp. 608-616.

Flescher, E., "Jasmonates—A New Family of Anti-Cancer Agents," Anti-Cancer Drugs, vol. 16, (2005), pp. 911-916.

Flescher, E., "Jasmonates in Cancer Therapy," Cancer Letters 245 (2007) 1-10.

Gfeller, A. et al., "Jasmonate Biochemical Pathway," Science Signaling, vol. 3, No. 109, Feb. 16, 2010, pp. 1-6.

IUPAC Compendium of Chemical Terminology, "Inclusion Compound (inclusion complex)," (2014), 2nd ed. (the "Gold Book"), available online at https://doi.org/10.1351/goldbook.102998.

Molineux, G., "Pegylation: engineering improved pharmaceuticals for enhanced therapy," Cancer Treatment Reviews 2002; 28(Suppl. A): 13-16.

Palmieri, B. et al., "A preliminary study of the local treatment of preneoplastic and malignant skin lesions using methyl jasmonate," European Review for Medical and Pharmacological Sciences, vol. 15 (2011) 333-336.

Rajewski, R. A. et al., "Pharmaceutical Applications of Cyclodextrins. 2. In Vivo Drug Delivery," J. Pharmaceut. Sci., vol. 85, No. 11 (Nov. 1996), pp. 1142-1169.

(56) References Cited

OTHER PUBLICATIONS

Rotem, R. et al., "Jasmonates: Novel Anticancer Agents Acting Directly and Selectively on Human Cancer Cell Mitochondria," Cancer Res., vol. 65, No. 5 (Mar. 1, 2005), pp. 1984-1993.

Swamy, S. G. et al., "Triacontanol and Jasmonic Acid Differentially Modulate the Lipid Organization as Evidenced by the Fluorescent Probe Behavior and $^{31}P$ Magnetic Resonance Shifts in Model Membranes," J. Membrane Biol. 228 (2009)165-177.

Maeda, H. et al., "Tumor vascular permeability and the EPR effect in macromolecular therapeutics: a review," Journal of Controlled Release, 2000, vol. 65, pp. 271-284.

Van De Manakker, F. et al., "Cyclodextrin-Based Polymeric Materials: Synthesis, Properties, and Pharmaceutical/Biomedical Applications," Biomacromolecules, 2009, vol. 10, No. 12, pp. 3157-3175.

Maranhao, R. C. et al., "Plasma Kinetics and Biodistribution of a Lipid Emulsion Resembling Low-Density Lipoprotein in Patients with Acute Leukemia," Cancer Research, Sep. 1994, vol. 54, pp. 4660-4666.

Ginsburg, G. S. et al., "Microemulsions of phospholipids and cholesterol esters," The Journal of Biological Chemistry, vol. 257, No. 14, Jul. 25, 1982, pp. 8216-8227.

Yeruva, L. et al., "Perillyl alcohol and methyl jasmonate sensitize cancer cells to cisplatin," Anti-cancer Drugs, 2010, vol. 21, No. 1, pp. 1-9.

Wang, Y. et al., "Methyl jasmonate sensitizes human bladder cancer cells to gambogic acid induced apoptosis through down-regulation of EZH2 expression by miR-101," British Journal of Pharmacology, 2014, vol. 171, pp. 618-635.

Dorwald, F. Z., Preface In: Side Reactions in Organic Synthesis. A Guide to Successful Synthesis Design, Wiley-VCH Verlag GmbH & Co. KGaA, Weinheim, p. IX, 2005.

Zhang, M. et al., "Methyl Jasmonate and its Potential in Cancer Therapy," Plant Signaling & Behavior, vol. 10, Issue 9, pp. e1062199-1-e1062199-3, Sep. 2015.

* cited by examiner

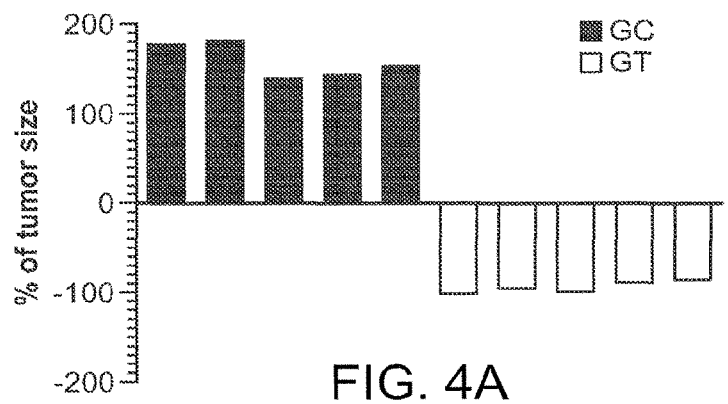
FIG. 4A
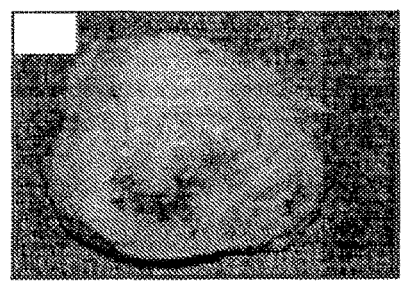
FIG. 4B
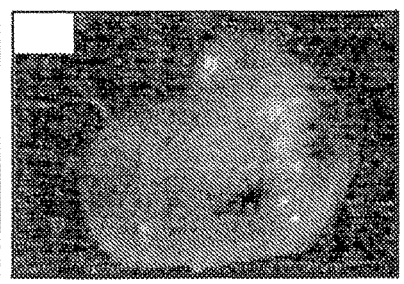
FIG. 4C
FIG. 4D
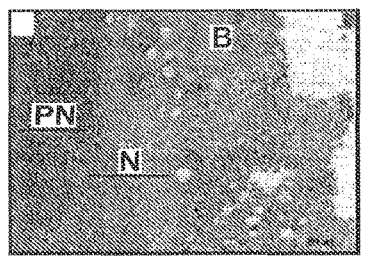
FIG. 4E
FIG. 4F
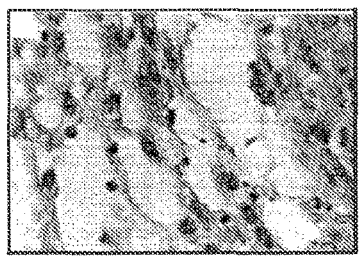
FIG. 4G
FIG. 4H
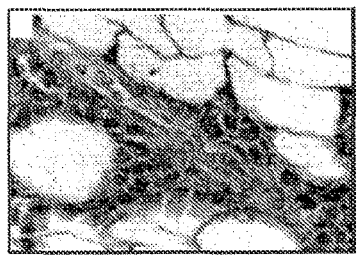
FIG. 4I
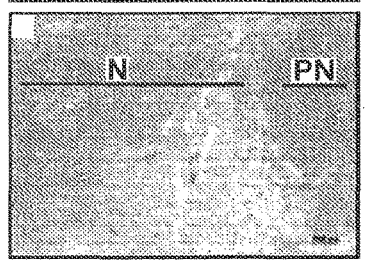
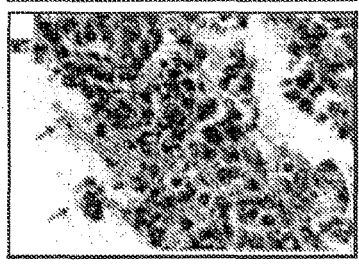

| GENE SYMBOL | Microarray (Fold change) | qPCR |
|---|---|---|
| WNT5A | -5.716 | -6.33 |
| Cyclin D | +3.775 | +1.90 |
| HIF-1 | -2.464 | -4.32 |
| TGFβ | -1.807 | -3.17 |
| TGFβR1 | +4.002 | +4.98 |
| MT | -2.029 | -4.02 |

FIG. 6E

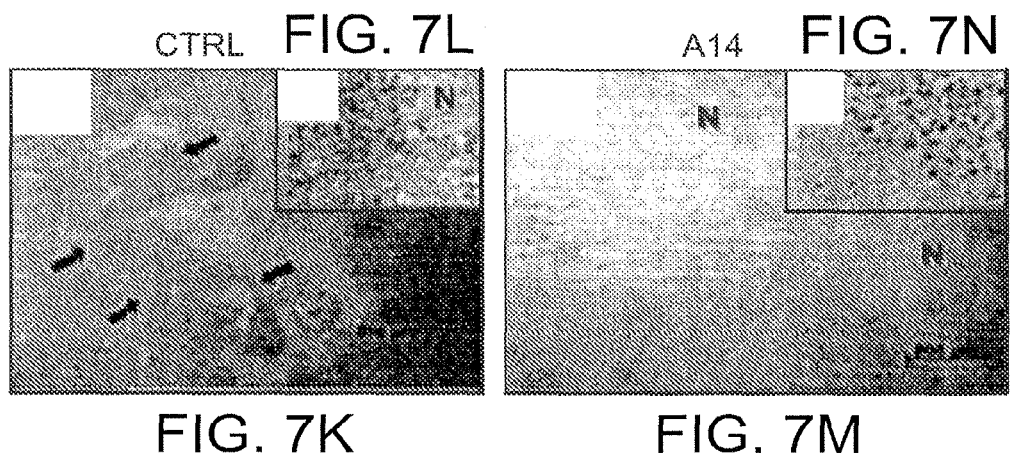
FIG. 7L  FIG. 7N
FIG. 7K  FIG. 7M
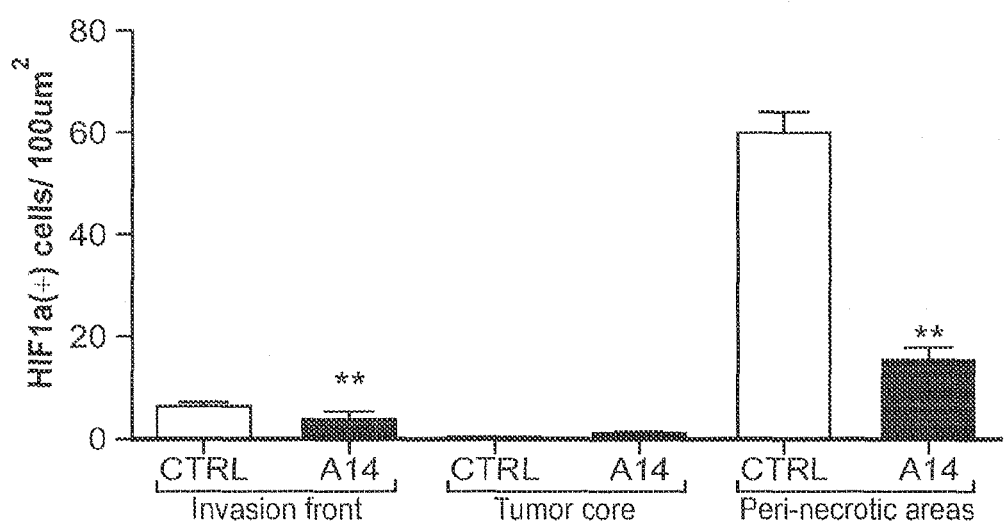
FIG. 7O

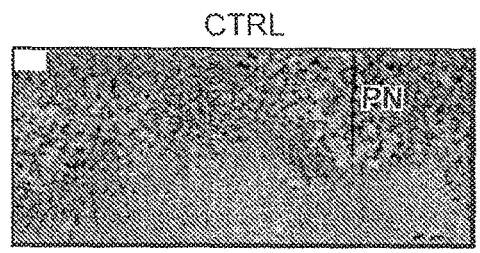
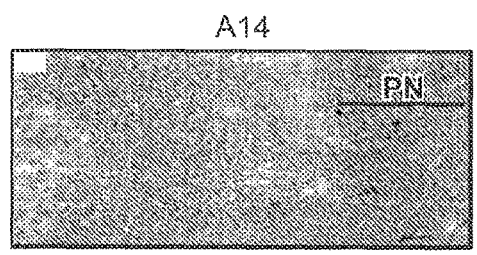
FIG. 8A  FIG. 8B
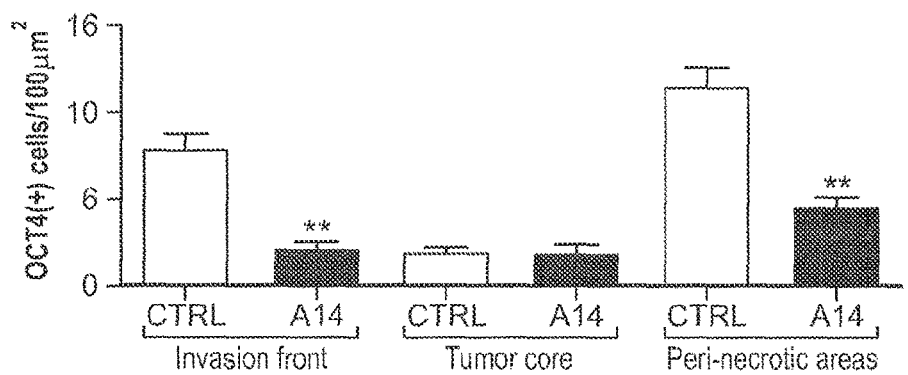
FIG. 8C
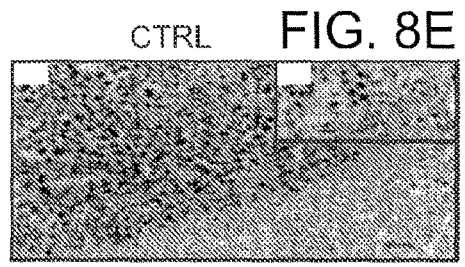
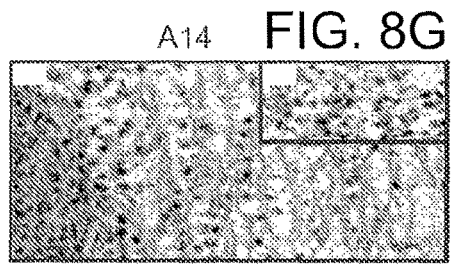
FIG. 8D  FIG. 8F
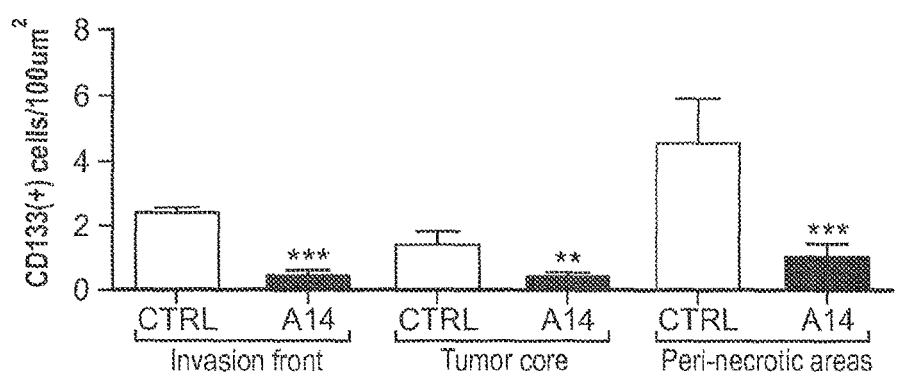
FIG. 8H

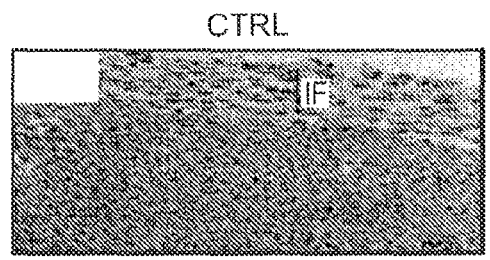
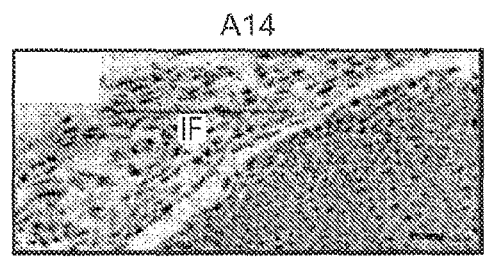
FIG. 8Q  FIG. 8R
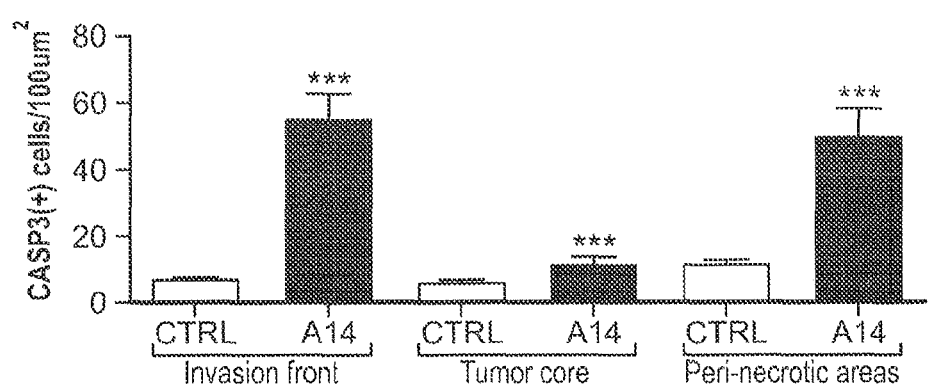
FIG. 8S

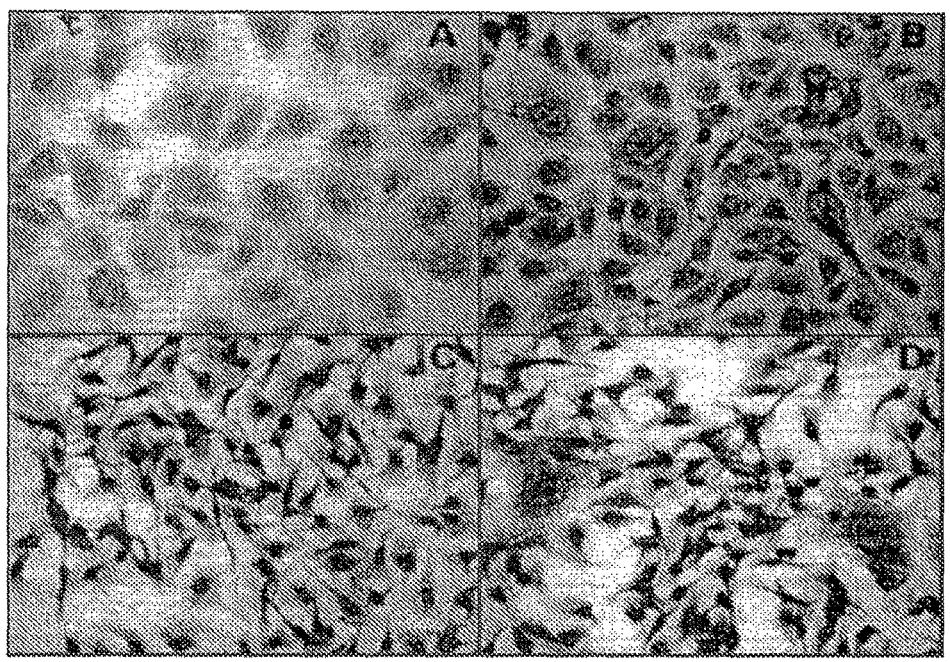
FIG. 12A  FIG. 12B
FIG. 12C  FIG. 12D
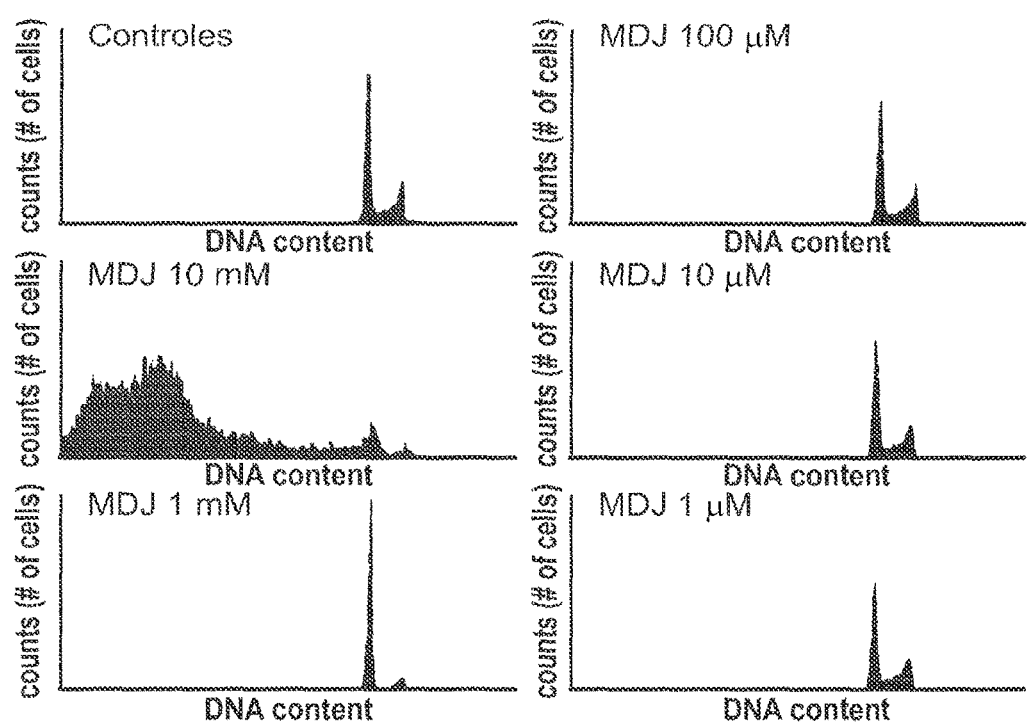
FIG. 13

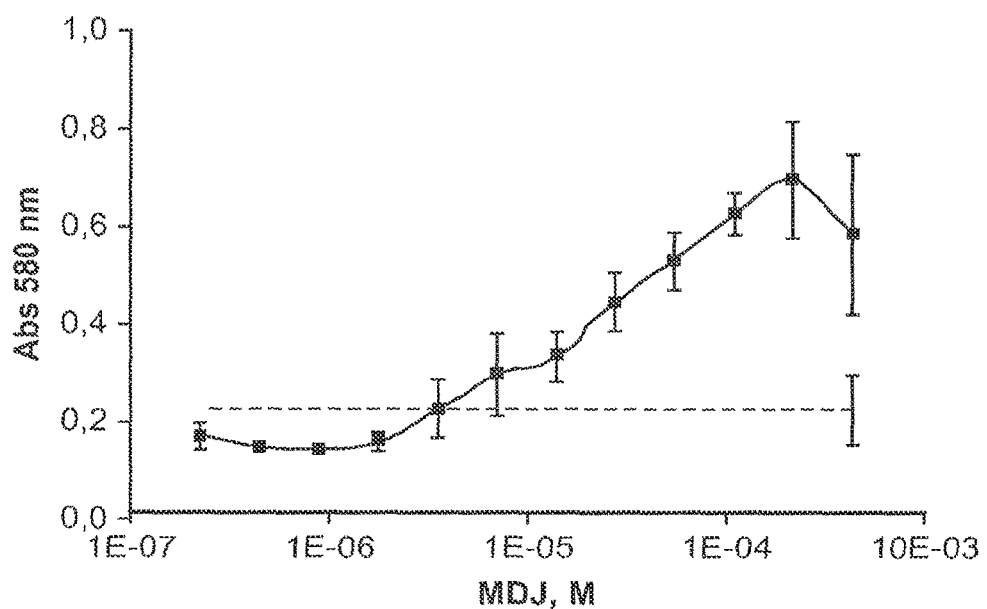
FIG. 14
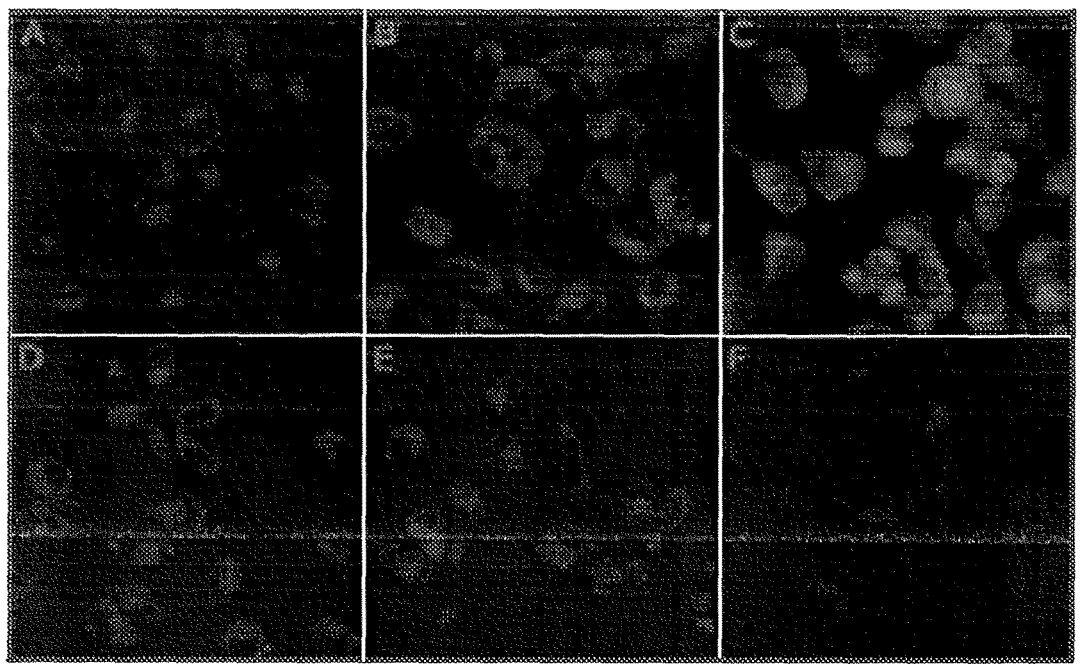
FIG. 15A    FIG. 15B    FIG. 15C
FIG. 15D    FIG. 15E    FIG. 15F

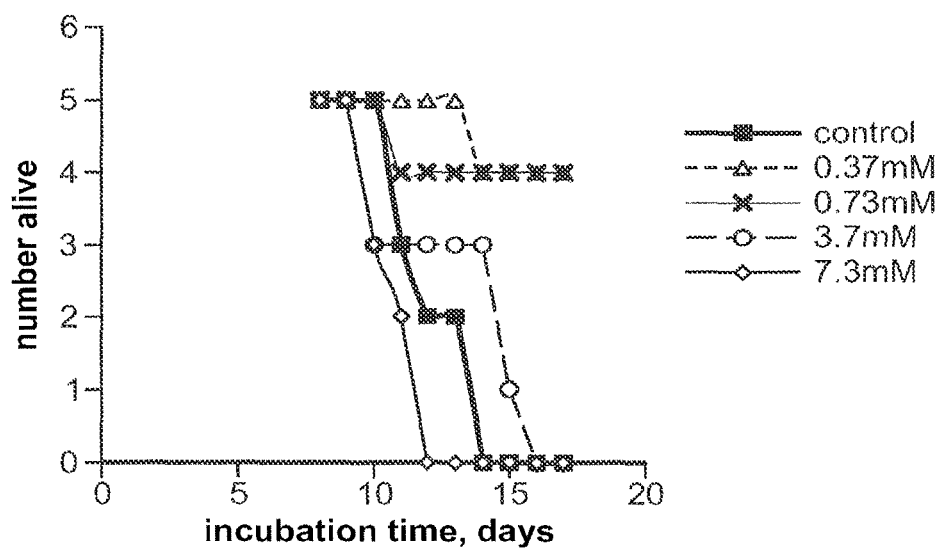
FIG. 19
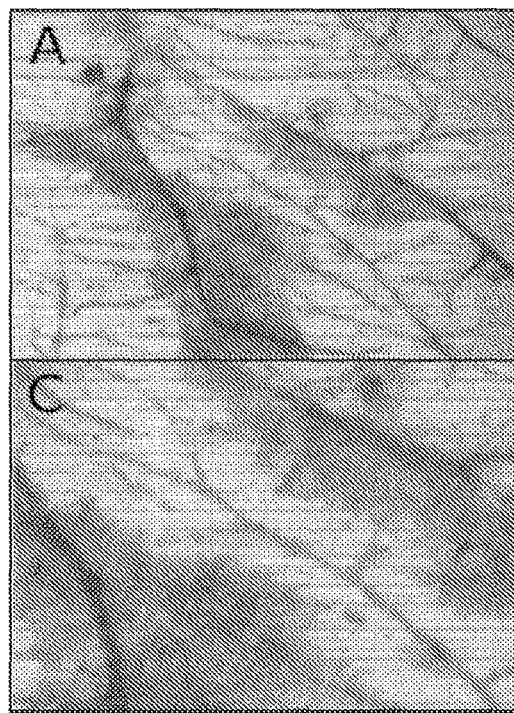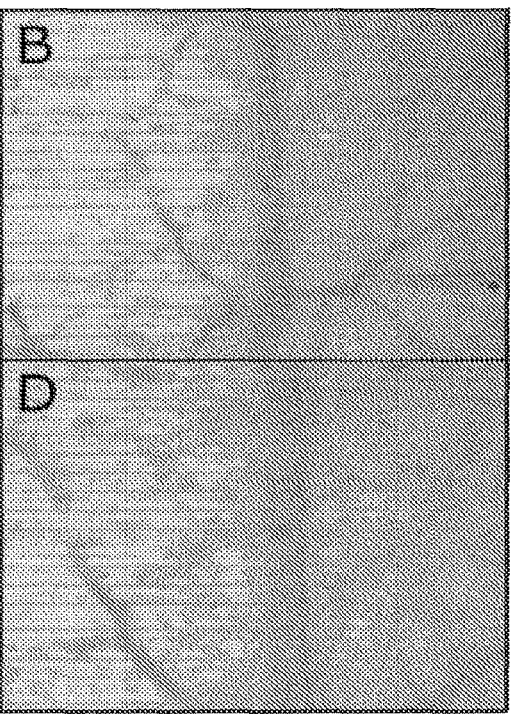
FIG. 20A    FIG. 20B
FIG. 20C    FIG. 20D

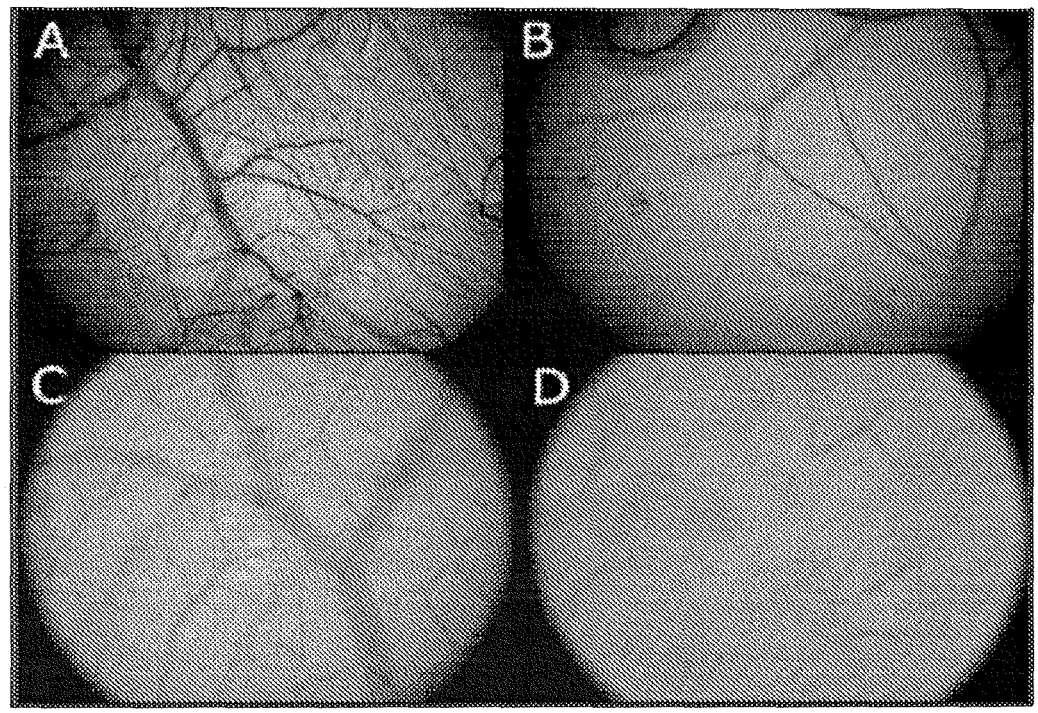
FIG. 24A  FIG. 24B
FIG. 24C  FIG. 24D
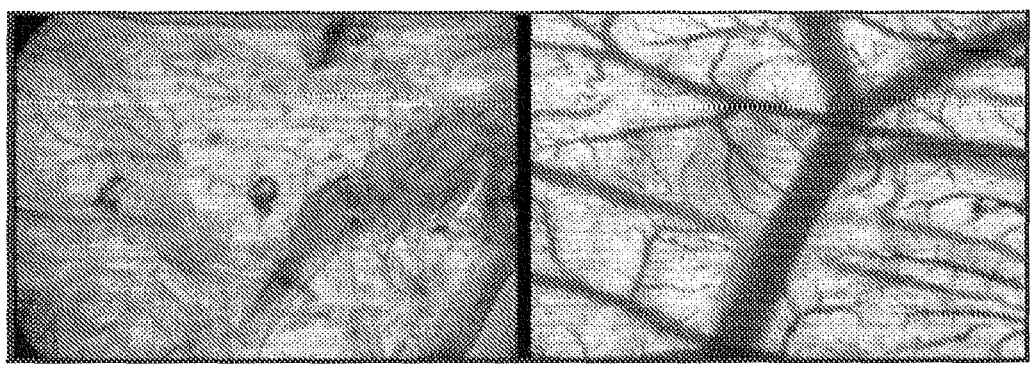
FIG. 25

Melanoma Treated With A-14 After 12 Hours With a Concentration 100 Micro Mols

A-14 Project

*In vivo* angiogenesis

*In vivo* angiogenesis

A: Untreated
B: Lipid carrier only
C: A14, $3 \times 10^{-5}$ M
D: A14, $3 \times 10^{-5}$ M in lipid carrier FIG. 42A
FIG. 42B
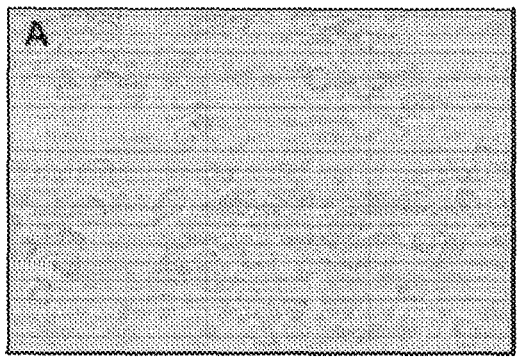
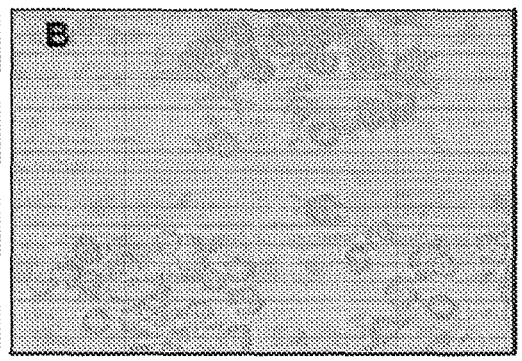
No Apoptosis
Macrophage activated by A14 and
increases the number of macrophage
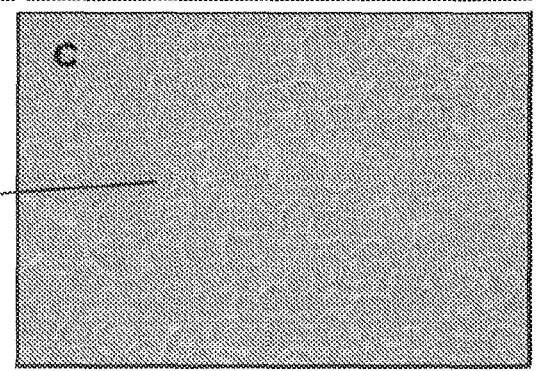
FIG. 42C

COMPOSITIONS OF JASMONATE COMPOUNDS AND METHODS OF USE

RELATED APPLICATIONS

This application is a continuation application of U.S. application Ser. No. 14/525,199, filed Oct. 27, 2014 (now allowed), which is a continuation application of U.S. application Ser. No. 13/621,570, filed Sep. 17, 2012 (now U.S. Pat. No. 8,883,220), which claims priority to, and the benefit of, U.S. provisional application Nos. 61/535,836, filed Sep. 16, 2011; 61/555,690, filed Nov. 4, 2011; 61/603,042, filed Feb. 24, 2012; 61/607,318, filed Mar. 6, 2012; and 61/612,774, filed Mar. 19, 2012; and International Application No. PCT/132012/000364, filed Feb. 27, 2012. The entire contents of each of the above applications are incorporated herein by reference in their entireties.

FIELD OF THE INVENTION

The present invention relates to pharmaceutical compositions of jasmonate compounds (e.g., nanocarried or microcarried jasmonate compounds) useful for the treatment and prevention of various diseases and disorders.

BACKGROUND OF THE INVENTION

Jasmonate compounds or jasmonates are characterized by the cyclopentanone ring and are known as plant stress hormones produced by plants facing a stressful situation. Examples of jasmonates include, but are not limited to, jasmonic acid (JA), methyl jasmonate (MJ), and cis-/trans-jasmone (see, e.g., U.S. Pat. No. 6,469,061 and WO 2007/066337). It has been shown that MJ and JA are both effective and selective against tumors cells (see, e.g., Flescher, *Anti-Cancer Drugs* 2005, 16:901-916 and US 2002/0173470). Yet, when administered in vivo, jasmonates are usually metabolized by, e.g., esterases, before they reach target cancer cells, rending them less attractive as anti-cancer agents.

SUMMARY OF THE INVENTION

The present invention, in part, provides nanocarried or microcarried jasmonates, especially, nanocarried or microcarried methyl dihydrojasmonate (MDJ, also known as methyl 2-(3-oxo-2-pentylcyclopentyl)acetate), for the application of treating or preventing various disorders, such as angiogenesis-related disorders and inflammatory diseases. The chemical structure of MDJ is shown below.

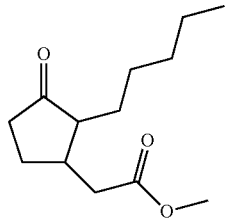 [SMILES: CCCCCC1C(=O)CCC1CC(=O)OC]

In one aspect, the present disclosure provides a pharmaceutical composition including a pharmaceutically acceptable solvent and a plurality of nanocarriers and/or microcarriers that contain MDJ. The nanocarriers and/or the microcarriers are formed of a cyclodextrin or a dendrimer, or a liposome, or are synthetic nanoemulsion particles (LDEs) comprising a cholesteryl ester core surrounded by a phospholipid outerlayer; the nanocarriers have a size ranging from 1 nanometer (nm) to 1000 nm (e.g., 1-900 nm, 1-800 nm, 1-700 nm, 1-600 nm, 1-500 nm, 1-400 nm, 1-300 nm, 1-200 nm, 1-100 nm, 1-90 nm, 1-80 nm, 1-70 nm, 1-50 nm, 1-30 nm, or 1-10 nm); the microcarriers have a size ranging from 1 micron to 50 micron (e.g., from 1 micron to about 40, 30, 20, 10, 9, 8, 7, 6, 5, 4, 3, 2, or 1.5 micron) and the pharmaceutical composition has a concentration of MDJ ranging from 1 nM to 1 M (e.g., from 1 nM to 10 nM, 1 nM to 100 nM, 1 nM to 1 μM, 1 nM to 10 μM, 1 nM to 100 μM, 100 μM to 1 mM, 100 μM to 10 mM, 100 μM to 100 mM, or 100 mM to 1 M).

The pharmaceutical composition may have one or more of the following features.

The pharmaceutical composition has a concentration of MDJ ranging from 1 nM to 10-100 μM (e.g., 1 nM to 10 nM, 10 nM to 100 nM, 100 nM to 1 μM, 1 μM to 10 μM, or 10 μM to 100 μM), or 100 μM to 1 mM (e.g., 100 μM to 200 μM, 300 μM, 400 μM, 500 μM, 600 μM, 700 μM, 800 μM, or to 900 μM), or 100 μM to 10 mM (e.g., from 100 μM, 200 μM, 300 μM, 400 μM, 500 μM, 600 μM, 700 μM, 800 μM, or from 900 μM to 1 mM, 2 mM, 3 mM, 4 mM, 5 mM, 6 mM, 7 mM, 8 mM, 9 mM, or to 10 mM), or 100 μM to 100 mM (e.g., from 100 μM, 200 μM, 300 μM, 400 μM, 500 μM, 600 μM, 700 μM, 800 μM, 900 μM, or from 1 mM to 10 mM, 20 mM, 30 mM, 40 mM, 50 mM, 60 mM, 70 mM, 80 mM, 90 mM, or to 100 mM), or 10 μM to 1 mM (e.g., from 10 μM, 20 μM, 30 μM, 40 μM, 50 μM, 60 μM, 70 μM, 80 μM, or from 90 μM to 0.1 mM, 0.2 mM, 0.3 mM, 0.4 mM, 0.5 mM, 0.6 mM, 0.7 mM, 0.8 mM, 0.9 mM, or to 1 mM), or 1-100 mM (e.g., 1-10 mM, 1-20 mM, 1-30 mM, 1-40 mM, 1-50 mM, 1-60 mM, 1-70 mM, 1-80 mM, or 1-90 mM), or 100 mM to 1 M (e.g., from 0.2 M, 0.3 M, 0.4 M, 0.5 M, 0.6 M, 0.7 M, 0.8 M, 0.9 M to 1M).

The nanocarriers are formed of a cyclodextrin and have a size ranging from 3 nm to 100 nm, e.g., 3.5-11 nm, 10-20 nm, 10-30 nm, 10-40 nm, 10-50 nm, 10-60 nm, 10-70 nm, 10-80 nm, 10-90 nm, 20-30 nm, 20-40 nm, 20-50 nm, 20-60 nm, 20-70 nm, 20-80 nm, 20-90 nm, 30-40 nm, 30-50 nm, 30-60 nm, 30-70 nm, 30-80 nm, 30-90 nm, 40-50 nm, 40-60 nm, 40-70 nm, 40-80 nm, 40-90 nm, or 50-60 nm, 50-70 nm, 50-80 nm, 50-90 nm, or 50-100 nm.

The nanocarriers are liposomes or LDEs and have a size ranging from 30 nm to 500 nm, e.g., 50 nm-110 nm, 30 nm to 50 nm, 30 nm to 100 nm, 30 nm to 150 nm, 30 nm to 200 nm, 30 nm to 250 nm 30 nm to 300 nm, 30 nm to 350 nm, 30 nm to 400 nm, or 30 nm to 450 nm.

The microcarriers are liposomes or LDEs and have a size ranging from about 2 μm to 30 μm (e.g., 2-5 μm, 2-10 μm, 2-15 μm, 2-20 μm, or 2-25 μm), about 5 μm to 20 μm (e.g., 5-7.5 μm, 5-10 μm, 5-12.5 μm, 5-15 μm, or 5-17.5 μm), or about 10 μm. Further, the concentration of MDJ ranges from 10-100 μM to 100 mM (e.g., from 50-100 μM or from 100 μM, 200 μM, 300 μM, 400 μM, 500 μM, 600 μM, 700 μM, 800 μM, or from 900 μM to 1 mM, 2 mM, 3 mM, 4 mM, 5 mM, 6 mM, 7 mM, 8 mM, 9 mM, or to 10 mM 10 mM, 20 mM, 30 mM, 40 mM, 50 mM, 60 mM, 70 mM, 80 mM, 90 mM, or to 100 mM) or 100 mM to 1 M (e.g., from 0.2 M, 0.3 M, 0.4 M, 0.5 M, 0.6 M, 0.7 M, 0.8 M, 0.9 M to 1M).

The nanocarriers are formed of a dendrimer and have a size ranging from 1 nm to 500 nm (e.g., 2-10 nm, 2-20 nm, 2-50 nm, 2-100 nm, 2-150 nm, 2-200 nm, 2-250 nm, 2-300 nm, 2-350 nm, 2-400 nm, 2-450 nm, 10-100 nm, 10-200 nm, 10-300 nm, 10-400 nm, 10-500 nm, 50-100 nm, 50-200 nm, 50-300 nm, 50-400 nm, 50-500 nm, 100-300 nm, 100-500 nm, 200-500 nm 300-500 nm, or 400-500 nm).

The dendrimer is polyamidoamine (PAMAM).

The concentration of MDJ ranges from 1 nM to 10-100 µM (e.g., 1 nM to 10 nM, 10 nM to 100 nM, 100 nM to 1 µM, 1 µM to 10 µM, or 10 µM to 100 µM), 10-100 µM to 100 mM (e.g., from 50-100 µM or from 100 µM, 200 µM, 300 µM, 400 µM, 500 µM, 600 µM, 700 µM, 800 µM, or from 900 µM to 1 mM, 2 mM, 3 mM, 4 mM, 5 mM, 6 mM, 7 mM, 8 mM, 9 mM, or to 10 mM 10 mM, 20 mM, 30 mM, 40 mM, 50 mM, 60 mM, 70 mM, 80 mM, 90 mM, or to 100 mM), or 100 mM to 1M (e.g., from 0.2 M, 0.3 M, 0.4 M, 0.5 M, 0.6 M, 0.7 M, 0.8 M, 0.9 M to 1M). For example, the concentration of MDJ is from 100 µM to 1 mM or 50 nM to 70 nM.

The nanocarriers or microcarriers further contain 2-aminoethyl dihydrogen phosphate (or phosphoethanolamine), 3,7-dimethyl-2,6-octadienal (or citral), methyl salicylate, abscisic acid, or derivatives or analogues thereof 3,7-Dimethyl-2,6-octadienal can either be a cis- or trans-isomer.

The pharmaceutically acceptable solvent is water, an alcohol, or a mixture thereof.

In another aspect, the present disclosure provides a pharmaceutical composition including a pharmaceutically acceptable solvent and a plurality of nanocarriers and/or microcarriers that contain a jasmonate compound. The nanocarriers and/or microcarriers are formed of a cyclodextrin or a dendrimer, or a liposome, or the nanocarriers and/or microcarriers are synthetic nanoemulsion particles (LDEs) comprising a cholesteryl ester core surrounded by a phospholipid layer. The nanoparticles have a size ranging from 1 nm to 1000 nm (e.g., 1-900 nm, 1-800 nm, 1-700 nm, 1-600 nm, 1-500 nm, 1-400 nm, 1-300 nm, 1-200 nm, 1-100 nm, 1-90 nm, 1-80 nm, 1-70 nm, 1-50 nm, 1-30 nm, or 1-10 nm); the microcarriers have a size ranging from 1 micron to 50 micron (e.g., from 1 micron to about 40, 30, 20, 10, 9, 8, 7, 6, 5, 4, 3, 2, or 1.5 micron) and the pharmaceutical composition has a concentration of the jasmonate compound ranging from 1 nM to 1 M (e.g., from 1 nM to 10 nM, 1 nM to 100 nM, 1 nM to 1 µM, 1 nM to 10 µM, 1 nM to 100 µM, 100 µM, to 1 mM, 100 µM to 10 mM, 100 µM to 100 mM, or 100 mM to 1 M).

The pharmaceutical composition may have one or more of the following features.

The jasmonate compound is selected from the group consisting of jasmonic acid, 7-iso-jasmonic acid, 9,10-dihydrojasmonic acid, 9,10-dihydro-isojasmonic acid, 2,3-didehydrojasmonic acid, 3,4-didehydrojasmonic acid, 3,7-didehydrojasmonic acid, 4,5-didehydrojasmonic acid, 4,5-didehydro-7-isojasmonic acid, cucurbic acid, 6-epi-cucurbic acid, 6-epi-cucurbic acid-lactone, 12-hydroxy-jasmonic acid, 12-hydroxy-jasmonic acid-lactone, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, tuberonic acid-O-β-glucopyranoside, cucurbic acid-O-β-glucopyranoside, 5,6-didehydro-jasmonic acid, 6,7-didehydro-jasmonic acid, 7,8-didehydro-jasmonic acid, cis-jasmone, dihydrojasmone, and a lower alkyl ester thereof.

The pharmaceutical composition has a concentration of the jasmonate compound ranging from 1 nM to 1 µM (e.g., from 1, 2, 3, 4, 5, 6, 7, 8, or 9 nM to 10, 50, 100, 150, 200, 250, 300, 350, 400, 450, 500, 550, 600, 650, 700, 750, 800, 850, 900, or 950 nM), 1 nM to 100 µM (e.g., 1 nM to 10 nM, 10 nM to 100 nM, 100 nM to 1 µM, 1 µM to 10 µM, or 10 µM to 100 µM), or 1 nM to 1 mM (e.g., from 50 nM, 100 nM, 200 nM, 500 nM, 1000 nM, 50 µM, or from 100 µM to 200 µM, 300 µM, 400 µM, 500 µM, 600 µM, 700 µM, 800 µM, or to 900 µM), or 10 µM to 100 mM (e.g., from 50 µM or from 90 µM to 0.1 mM, 0.2 mM, 0.3 mM, 0.4 mM, 0.5 mM, 0.6 mM, 0.7 mM, 0.8 mM, 0.9 mM, 1 mM, 10 mM, 20 mM, 40 mM, 50 mM, 60 mM, 70 mM, 80 mM, or to 90 mM), or 100 µM to 1 mM (e.g., 100 µM to 200 µM, 300 µM, 400 µM, 500 µM, 600 µM, 700 µM, 800 µM, or to 900 µM), or 100 µM to 10 mM (e.g., from 100 µM, 200 µM, 300 µM, 400 µM, 500 µM, 600 µM, 700 µM, 800 µM, or from 900 µM to 1 mM, 2 mM, 3 mM, 4 mM, 5 mM, 6 mM, 7 mM, 8 mM, 9 mM, or to 10 mM), or 100 µM to 100 mM (e.g., from 100 µM, 200 µM, 300 µM, 400 µM, 500 µM, 600 µM, 700 µM, 800 µM, 900 µM, or from 1 mM to 10 mM, 20 mM, 30 mM, 40 mM, 50 mM, 60 mM, 70 mM, 80 mM, 90 mM, or to 100 mM), or 10 µM to 1 mM (e.g., from 10 µM, 20 µM, 30 µM, 40 µM, 50 µM, 60 µM, 70 µM, 80 µM, or from 90 µM to 0.1 mM, 0.2 mM, 0.3 mM, 0.4 mM, 0.5 mM, 0.6 mM, 0.7 mM, 0.8 mM, 0.9 mM, or to 1 mM), or 1-100 mM (e.g., 1-10 mM, 1-20 mM, 1-30 mM, 1-40 mM, 1-50 mM, 1-60 mM, 1-70 mM, 1-80 mM, or 1-90 mM), or 100 mM to 1 M (e.g., from 0.2 M, 0.3 M, 0.4 M, 0.5 M, 0.6 M, 0.7 M, 0.8 M, 0.9 M to 1M).

The nanocarriers are formed of a cyclodextrin and have a size ranging from 3 nm to 100 nm, e.g., 3.5-11 nm, 10-20 nm, 10-30 nm, 10-40 nm, 10-50 nm, 10-60 nm, 10-70 nm, 10-80 nm, 10-90 nm, 20-30 nm, 20-40 nm, 20-50 nm, 20-60 nm, 20-70 nm, 20-80 nm, 20-90 nm, 30-40 nm, 30-50 nm, 30-60 nm, 30-70 nm, 30-80 nm, 30-90 nm, 40-50 nm, 40-60 nm, 40-70 nm, 40-80 nm, 40-90 nm, or 50-60 nm, 50-70 nm, 50-80 nm, 50-90 nm, or 50-100 nm.

The nanocarriers are LDEs and have a size ranging from 30 nm to 500 nm, e.g., 50 nm-110 nm, 30 nm to 50 nm, 30 nm to 100 nm, 30 nm to 150 nm, 30 nm to 200 nm, 30 nm to 250 nm 30 nm to 300 nm, 30 nm to 350 nm, 30 nm to 400 nm, or 30 nm to 450 nm.

The microcarriers are liposomes or LDEs and have a size ranging from about 2 µm to 30 µm (e.g., 2-5 µm, 2-10 µm, 2-15 µm, 2-20 µm, or 2-25 µm), about 5 µm to 20 µm (e.g., 5-7.5 µm, 5-10 µm, 5-12.5 µm, 5-15 µm, or 5-17.5 µm), or about 10 µm. Further, the jasmonate compound is MDJ and the concentration of MDJ ranges from 100 mM to 1 M (e.g., from 0.2 M, 0.3 M, 0.4 M, 0.5 M, 0.6 M, 0.7 M, 0.8 M, 0.9 M to 1M).

The nanocarriers are formed of a dendrimer and have a size ranging from 2 nm to 500 nm (e.g., 2-10 nm, 2-20 nm, 2-50 nm, 2-100 nm, 2-150 nm, 2-200 nm, 2-250 nm, 2-300 nm, 2-350 nm, 2-400 nm, 2-450 nm, 10-100 nm, 10-200 nm, 10-300 nm, 10-400 nm, 10-500 nm, 50-100 nm, 50-200 nm, 50-300 nm, 50-400 nm, 50-500 nm, 100-300 nm, 100-500 nm, 200-500 nm 300-500 nm, or 400-500 nm).

The dendrimer is polyamidoamine (PAMAM).

The jasmonate compound is MDJ and the concentration of MDJ ranges from 1 nM to 10-100 µM, 10-100 µM to 100 mM, or 100 mM to 1M, e.g., 100 µM to 1 mM or 50 nM to 70 nM.

The jasmonate compound is MJ and the concentration of MJ ranges from 1 nM to 1 µM, 10-100 µM to 100 mM, or 100 mM to 1M, e.g., 100 µM to 1 mM or 50 nM to 70 nM.

The nanocarriers or microcarriers further contain 2-aminoethyl dihydrogen phosphate (or phosphoethanolamine), 3,7-dimethyl-2,6-octadienal (or citral), methyl salicylate, abscisic acid, or derivatives or analogues thereof 3,7-Dimethyl-2,6-octadienal can either be a cis- or trans-isomer.

The pharmaceutically acceptable solvent is water, an alcohol, or a mixture thereof. Any of the compounds described herein can additionally include one or more non-jasmonate compounds, such as, for example, 2-aminoethyl dihydrogen phosphate (or phosphoethanolamine), 3,7-dimethyl-2,6-octadienal (or citral), methyl salicylate, abscisic acid, natural amino acids, $Ca^{2+}$, $Zn^{2+}$, or derivatives or analogues thereof.

In yet another aspect, the present disclosure describes the use of the nanocarried and/or microcarried jasmonate compounds or their pharmaceutical compositions described herein for the treatment or prevention of an angiogenesis-related disorder, such as cancer or an inflammatory disorder (e.g., inflammatory bowel disorder, acute dermatitis, pelvic inflammatory disorder, or tonsillitis).

In still another aspect, the present disclosure describes use of the nanocarried and/or microcarried jasmonate compounds or their pharmaceutical compositions described herein for the treatment or prevention of an NF-κB-related disorder, such as a viral, bacterial, or fungal infection.

Further, the invention features use of the nanocarried and/or microcarried jasmonate compounds or their pharmaceutical compositions described herein for inhibiting cancer cell growth in vitro or in vivo. For example, cancer cell lines suitable for use in the methods of this invention include: UACC62—melanoma, MCF7—cancer resistance, NCIADR—multiple drug resistant breast cancer, 7860—kidney cancer, NC1460—lung cancer, PCO3—prostrate cancer resistance, OVCAR03—ovary Cancer, HT29—Colon Cancer, K562—leukemia, TCP-1003 (Triple-Negative Breast Cancer Panel 3), Caco-2—colon cancer, a panel of 18 triple-negative breast tumor cell lines sharing a mesenchymal-like or luminal morphology; breast cancer cell lines HCC38 (ATCC® Number: CRL-2314™) and MCF7 (ATCC® Number: HTB-22™); prostate adenocarcinoma cell line PC-3 (ATCC® Number: CRL-1435™); prostate cancer cell line VCaP (ATCC® Number: CRL-2876™); prostate carcinoma cell line 22Rv1 (ATCC® Number: CRL-2505™); prostate carcinoma cell line DU 145 (ATCC® Number: HTB-81™); prostate carcinoma cell line LNCaP clone FGC (ATCC® Number: CRL-1740™); leukemia cell line MOLT-4 (ATCC® Number: CLR-1582™); leukemia (AML) cell line KG-1 (ATCC® Number: CCL-246™); leukemia (CML) cell line K-562 (ATCC® Number: CCL-243™); leukemia human cell line CCRF-CEM (ATCC® Number: CCL-119™); CLL leukemia cell line Hs 505.T (ATCC® Number: CRL-7306™); Jurkat cell line (leukemia, ATCC® Number: TIB-156™); Molm cell lines (leukemia, e.g., Molm-13, Molm-14, Molm-16, Molm-17, and Molm-18), Nomo cell lines (leukemia, e.g., NOMO-1) and Ras mutant cells.

The nanocarried and/or microcarried jasmonate compounds (e.g., MDJ) or their pharmaceutical compositions described herein have the following advantages. They show in vitro and/or in vivo anticancer activities in a range of cancers such as prostate cancer, breast cancers, melanoma, colon cancer, leukemia while showing little or no toxicity to healthy cells in vivo. Their novel mechanism of action may be complementary to other established drug therapies for prostate cancer. For example, for advanced diseases, the composition of the invention can reduce use of aggressive therapies that have side effects, and for localized diseases, the composition of the invention can prolong effectiveness of sensitivity to hormone therapy and delay progression to metastatic diseases.

The present disclosure also describes methods of synthesizing the nanocarried and/or microcarried jasmonate compounds or their pharmaceutical compositions described herein.

BRIEF DESCRIPTION OF THE DRAWINGS

The terms "A-14" and "A14" are used interchangeable in the figures to refer to the MDJ-nanocarrier complex used for the measurement.

FIGS. 6A-6E: Schematic view of the microarray data. In FIG. 6A, a scatter plot of data set shows the gene distribution of both groups, along the central axes (eigenvectors). The analyzed genes are distributed according to the minimum until the maximum range, including their fold change values, revealed by color defaults. In FIG. 6B, clustering algorithms (K-Means) like hierarchical clustering, revealed the most similar entities merged together based on the similarity of their expression profiles. The Interactions of Proteins Representing the Gene Classifier of the proteins are present in the Ingenuity database. These are represented by colored symbols (green symbols indicate proteins that have smaller induction after cyclodextrin-carried MDJ and red symbols indicate proteins that have higher induction. The intensity of the colors indicates the difference between the groups in the magnitude of induction. The connecting proteins are represented by empty symbols. Only a few of the colored proteins are not directly or indirectly linked through a connecting protein. Some of the factors involved in angiogenesis, in FIG. 6C amd a general picture may be seen in FIG. 6D. In FIG. 6E, concordant results can be observed between the methods of microarray data and qRP-PCR, for some sampled genes.

FIGS. 7A-7C show a marked reduction of both subunities of NFkB (P105 and P50) by western-blotting in group GT, when compared to group GC. Furthermore, southwestern histochemistry analysis confirmed that NFkB transcription to nucleus was virtually abolished in group GT (FIG. 7E), when compared to group GB (FIG. 7D). The only exception was a marked and highly NFkB staining in vessels (FIG. 7F) only in group GT in areas with vascular damage, viewed in H&E staining. Note—as the number of vessels was small, this may not have affected the overall quantification of NFkB, by WB analysis. TGFβ immuno-staining was much more intense in group GC, mainly in PN areas, as delimited by black arrows (FIG. 7H), when compared to GT (FIG. 7I), what was confirmed by morphometry (FIG. 7J). Also, HIF-1 immuno-staining was much more intense in group GC, mainly in PN areas (FIGS. 7K and 7L), when compared to GT (FIGS. 7M and 7N), what was confirmed by morphometry (FIG. 7O) and westernblotting analysis (FIGS. 7P and 7Q). COX-2 staining has shown a higher concentration of marked cells in the invasion front of the GC tumors, with many cells organized in cords (FIG. 7R), what was abolished in group GT, in which it was also found a marked disorganization of the tissue (FIG. 7S). Morphometry (FIG. 7T) confirmed the fall in IHC expression of COX-2 in group GT, with the exception of the central core of the tumors. Mann-Whitney test (*p<0.01).

FIGS. 8A-8S: Stem cell markers (CD133, Oct4 and MT) and apoptosis markers (Tunel and CASPASE3). FIGS. 8A-8F show similar pattern of IHC staining for both stem cell markers Oct4 and CD133. Immuno-staining was much more intense in group GC, mainly in PN areas (FIGS. 8A, 8D, and 8E, respectively), when compared to GT (FIGS. 8B and 8F/8G, respectively), what was confirmed by morphometry (FIGS. 8C and 8H, respectively). MT immuno-staining was much more intense in group GC, mainly in IF areas (FIGS. 8I and 8J), when compared to GT (FIGS. 8K and 8L), what was confirmed by morphometry (FIG. 8M). MT staining also showed an important disorganization of the cell cords and vessels in group GT. Both TUNEL and Caspase-3 staining have shown higher apoptosis levels in GT group in all the three areas that were evaluated (FIGS. 8O and 8R, respectively), when compared to the group GC (FIGS. 8N and 8Q, respectively), what was confirmed by morphometric analysis (FIGS. 8P and 8S). Mann-Whitney test (*p<0.01)

FIGS. 12A-12D: Representative image of endothelial cells (FIGS. 12A and 12B) or murine melanoma B16F10 (FIGS. 12C and 12D) grown to confluence on glass slides in RPMI medium in the control condition (FIGS. 12A and 12C) or after 60 h exposure to 1 mM MDJ (FIGS. 12B and 12D).

FIG. 13: Effect of MDJ on the cell cycle in HUVEC after 18 h of exposure in vitro. The concentrations used in each test are shown in graphics measures cell cycle were performed on a BD FACScalibur equipment, after labeling with propidium iodide simple. The staining with acridine orange served as a control of the process of apoptosis.

FIG. 14: Effect of MDJ on the viability of endothelial cells in 24 low-density plating (HUVEC, $1\times10^4$ cells/well), as measured by MTT reduction assay in 96 wells plates. Each point represents the average of eight readings performed in four independent experiments, the continuous line represents the measure of the unexposed controls for comparison. The effect on the mitochondria was confirmed by staining with Mitotracker Red and confocal microscopic observation and can be observed already at 4 h of exposure (See FIGS. 15A-15F).

FIGS. 15A-15F each show effect of MDJ on the mitochondrial activity of endothelial cells after 4 h of exposure in low-density plating on glass coverslips 25 mm in 24-well plates, as measured by Mitotracker red fluorescence confocal microscopy, increased 80× (40×+2× digital zoom). The calibration parameters were maintained for all measures. The measure of brightness corresponding to the fluorescent staining of mitochondria was quantified in relation to the marked area, suggesting that there is an increase in the number or mitochondrial activity in cells exposed to low concentrations of MDJ, also at 24 hours. Concentrations equal to or greater than 1 mM lead to a decrease in the intensity/area of marking.

FIG. 19: Toxicity of MDJ in vivo study of survival in eggs inoculated with B16F10 murine melanoma, $1 \times 10^4$ cells/well. The fertilized eggs were exposed to MDJ in doses of 100, 50, 10, 5 μL per egg (n=5) in a volume of 5 ml of albumin removed from the egg itself. The controls were exposed to vehicle without MDJ. The concentrations indicated in the legend were calculated assuming the volume of 60 mL/egg.

FIGS. 20A-20D: Effect of MDJ administered albumin on the growth of melanoma in the area of CAM. All samples were inoculated with B16F10 murine melanoma, $1 \times 10^4$ cells/well. FIGS. 20A and 20B, with increased image 5×, FIGS. 20C and 20D, the same region imaged in increased 10×. FIGS. 20A and 20C, untreated control, FIGS. 20B and 20D, treatment with single dose of 5 uL MDJ. Tumor growth is closely related to the vessels. Melanoma induced angiogenesis and grew close to the major vessels of the CAM.

FIG. 21A: digitized image estereroscópica the magnifying glass in bright field and FIG. 21B: the same region, image taken in dark field. 10× magnification.

FIGS. 24A-24D: Effect of cyclodextrin-carried MDJ on the growth of blood vessels in the CAM model of angiogenesis. FIGS. 24A and 24B: photomicrographs made on fresh material without staining. Jena microscope, illumination with parallel capacitor. 8× increase. FIGS. 24C and 24D: photomicrographs made on fresh material without staining, microscope Jena, lighting capacitor parallel increase 32×. Samples obtained in independent trials. FIGS. 24A and 24C: untreated controls. FIGS. 24B and 24D: Dose applied to the CAM equivalent to 1 μM MDJ.

FIG. 25: Effect of cyclodextrin-carried MDJ on vessel growth in the model of angiogenesis in CAM inoculated with B16F10 murine melanoma, $1 \times 10^4$ cells/well on the 8th day of incubation. Photomicrographs taken in the fresh material without staining, microscope Jena, lighting capacitor parallel increase 32×. A: untreated control. B: sample treated with cyclodextrin-carried MDJ applied on the CAM at day 11 of incubation, the equivalent of 1 μM MDJ.

FIG. 34A: microscopic picture of cancer cells (bright) engulfed by macrophages (dim); FIG. 34B: microscopic picture of cancer cells being digested inside a macrophage.

FIG. 36B: treated with lipid carrier only; FIG. 36C: treated with 30 μM MDJ; FIG. 36C: treated with 30 μM MDJ in lipid carrier).

FIGS. 38A-38C: Inverted microscope images of Jurkat cell line (leukemia, ATCC® Number: TIB-156™) after 24 hrs of treatment with: FIG. 38A: water (control); FIG. 38B: empty nanoparticles; and FIG. 38C: nanoparticles carrying MDJ. In FIG. 38C, nearly all cells died after 24 hrs of treatment.

FIGS. 39A-39C: Inverted microscope images of prostate cancer cell line VCaP (ATCC® Number: CRL-2876™) after 24 hrs of treatment with: FIG. 39A: water (control); FIG. 39B: empty nanoparticles; and FIG. 39C: nanoparticles carrying MDJ. In FIG. 39C, nearly all cells died after 24 hrs of treatment.

FIGS. 40A-40C: Inverted microscope images of breast cancer cell lines HCC38 (ATCC® Number: CRL-2314™) after 24 hrs of treatment with: FIG. 40A: water (control); FIG. 40B: empty nanoparticles; and FIG. 40C: nanoparticles carrying MDJ. In FIG. 40C, nearly all cells died after 24 hrs of treatment.

FIGS. 41A-41C: Inverted microscope images of prostate carcinoma cell line 22Rv1 (ATCC® Number: CRL-2505™) after 24 hrs of treatment with: FIG. 41A: water (control); FIG. 41B: empty nanoparticles; and FIG. 41C: nanoparticles carrying MDJ. In FIG. 41C, 60%-70% cells died after 24 hrs of treatment.

FIGS. 42A-42C: Inverted microscope images of macrophage cells after 24 hrs of treatment with: FIG. 42A: water (control); FIG. 42B: empty nanoparticles; and FIG. 42C: nanoparticles carrying MDJ.

FIG. 44A: an enormous amount of vessels, angiogenesis were formed around the tumor cells. In order to grow, the tumor needs to receive a larger amount of nutrients and oxygen. Due to such a need, the vessel complex is formed inside/into the tumor after the VEGF (Vascular Endothelial Grow Factor) is released by the tumor. FIG. 44B: After being treated with A-14 conjugated with amino acids, most of the vessel complex disappeared. The phenomenon named anti-angiogenesis, the destruction of those vessels, prevents the tumor from receiving the nutrients and oxygen required for its growth. The carrier is liposome.

DETAILED DESCRIPTION

Figure 37:
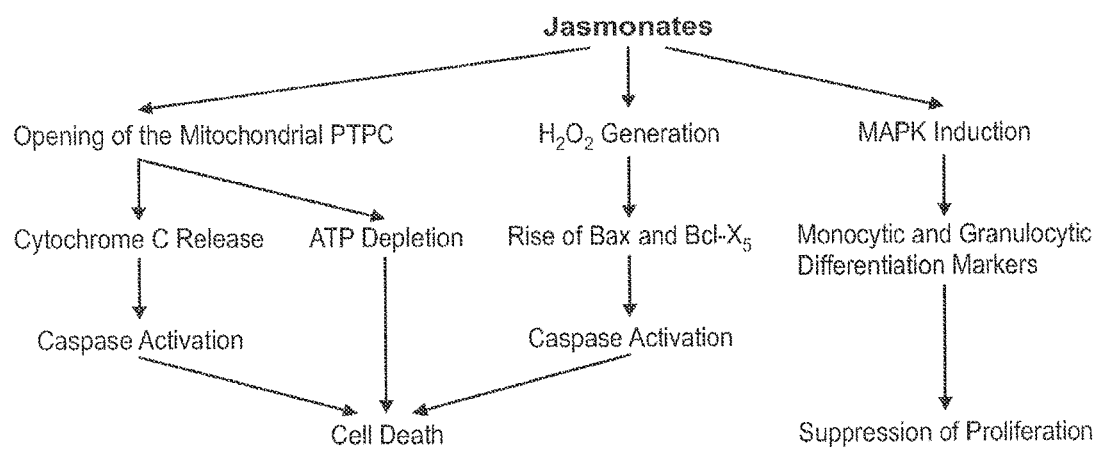
FIG. 37: Pathways of jasmonate action against cancer cells (See Flescher, Cancer Lett. 2007; 245(1-2):1-10.)

Jasmonates have been found to be potential anticancer agents acting directly and selectively on human cancer cell mitochondria (see, e.g., Rotem et al., *Cancer Res* 2005; 65:1984-1993; Costantini et al., JNCI 2000; 90:1042-1053) It has been reported that members of jasmonates, and some of their synthetic derivatives, exhibit anti-cancer activity in vitro and in vivo. For example, jasmonates increased the life span of EL-4 lymphoma-bearing mice, MJ is active in chemo-resistant B-lymphoma cells, and preliminary data has suggested that MJ exhibits cytotoxicity via apoptotic pathway (see, e.g., Flescher, *Cancer Lett.* 2007; 245(1-2):1-10; Fingrut et al., *Br J Pharmacol.* 2005; 146(6): 800-808; Fingrut et al., *Leukemia,* 2002; 16:608-616.) Mechanisms of action have been proposed to explain the anti-cancer activity of jasmonates (See id., and FIG. 37). However, the major problem facing this new family of anti-cancer agents is the difficulty to administer the compounds in vivo. Being an ester, when administered in vivo, jasmonates are usually metabolized by, e.g., esterases, before they reach target cancer cells, rending them less attractive as anti-cancer agents.

The invention provides pharmaceutical compositions of nanocarried and/or microcarried jasmonates. It is intended that the composition of the invention are "pharmaceutical" compositions, meaning that they are suitable for pharmaceutical use. Accordingly, the term "composition" as used herein is meant to encompass pharmaceutical compositions even if "pharmaceutical" is not expressly stated. The compositions of the invention preferably provide stability against degradation of the jasmonates before they reach target cells in vivo. The invention is based in part upon the unexpected discovery that nanocarried and/or microcarried jasmonates, in particular, nanocarried and/or microcarried MDJ, show anti-angiogenesis activities. The invention is also based in part on the unexpected discovery that nanocarried and/or microcarried MDJ is much more effective against tumor cells than nanocarried MJ, e.g., at least $10^3$ more effective, with less toxicity to normal cells and blood vessels. The invention is also based in part upon the unexpected discovery that nanocarried and/or microcarried jasmonates, in particular, nanocarried and/or microcarried MDJ or MJ, show either anti-angiogenesis activities or angiogenesis activities based on different doses or concentrations. For example, at a low concentration of 1 nM to about 10-100 µM, the nanocarried and/or microcarried MDJ exhibit angiogenesis effect, while at a concentration of greater than 100 µM, the nanocarried and/or microcarried MDJ exhibit anti-angiogenesis effect. As to MJ, at a low concentration of 1 nM to about 1 µM, the nanocarried and/or microcarried MJ exhibit angiogenesis effect, while at a concentration of greater than 1 µM (e.g., greater than 2 µM or greater than 5 µM) the nanocarried and/or microcarried MDJ exhibit anti-angiogenesis effect.

The above unexpected discoveries suggest that nanocarried/microcarried jasmonate be used as a new and promising targeted anti-cancer therapy.

As used in the specification and the appended claims, the singular forms "a," "an," and "the" include plural referents unless the context clearly dictates otherwise. Thus, for example, reference to "a jasmonate compound" may include not only a single jasmonate but also a combination or mixture of two or more different jasmonates including prodrugs, esters, salts, metabolites thereof.

As used herein, the phrases "for example," "for instance," "such as," or "including" are meant to introduce examples that further clarify more general subject matter. These examples are provided only as an aid for understanding the disclosure, and are not meant to be limiting in any fashion.

In describing and claiming the present invention, the following terminology will be used in accordance with the definitions set out below.

As used herein, the phrase "containing," "being formed/composed of," "including," "having the formula," or "having the structure" is not intended to be limiting and is used in the same way that the term "comprising" is commonly used unless the context clearly dictates otherwise.

The term "nanocarrier" as used herein refers to a carrier or vehicle suitable for carrying and delivering an active ingredient (e.g., a drug) to a target cell, tissue, or organ and the vehicle has a size in the range of about 1 nanometer (nm) to about 1000 nm. The term "microcarrier" as used herein refers to a carrier or vehicle suitable for carrying and delivering an active ingredient (e.g., a drug) to a target cell, tissue, or organ and the vehicle has a size in the range of about 1 micron to about 100 micron. In one embodiment, a microcarrier is formed of a cluster of nanocarriers, e.g, an LDE microcarrier formed of a cluster of LDE nanocarriers. Preferably, the nanocarrier or microcarrier is a pharmaceutically acceptable carrier.

The term "nanocarried/microcarried compound" or the term "nanocarrier/microcarrier containing a compound" as used herein refers to a complex of a nanocarrier/microcarrier associated or coupled with a compound. The association or coupling can be created via a chemical bond (e.g., a covalent bond), a hydrogen bond, a van der Waals force, a Coulomb interaction, or the like. In one embodiment, the compound is encapsulated in the nanocarrier/microcarrier. In another embodiment, the compound is partially encapsulated in the nanocarrier/microcarrier or at the surface of the nanocarrier/microcarrier (e.g., either as a part of the nanocarrier/microcarrier surface or outside yet attached to the surface).

The term "emulsion" refers to a suspension of small globules or particles of a first liquid (the dispersed phase) dispersed in a second liquid (the continuous phase), with which the first is normally immiscible.

The term "nanoemulsion" as used herein refers to an emulsion having the dispersed particles with a size ranging from about 1 nm to about 50 μm (e.g., 1 nm-50 μm, 1 nm-40 μm, 1 nm-30 μm, 1 nm-20 μm, 1 nm-10 μm, 1-5000 nm, 1-4000 nm, 1-3000 nm, 1-2000 nm, 1-1000 nm, 1-900 nm, 1-800 nm, 1-700 nm, 1-600 nm, 1-500 nm, 1-400 nm, 1-300 nm, 1-200 nm, 1-150 nm, 1-100 nm, 1-90 nm, 1-80 nm, 1-70 nm, 1-60 nm, 1-50 nm, 1-40 nm, 1-30 nm, 1-20 nm, 1-10 nm, 1-5 nm, 50-100 nm, 3-150 nm, or 3-20 nm). Nanoemulsions tend to appear clear due to the small size of the dispersed phase.

The term "LDE" refers to a nanoemulsion particle that resembles low-density lipoprotein (LDL) in composition and behavior. For example, once introduced into the circulation system, various plasma proteins (e.g., apoE) become absorbed onto the surface of LDE particles and subsequently direct the LDE to cells expressing LDL receptors (LDLR). LDE is protein free and is typically composed of a cholesteryl ester core surrounded by a phospholipid monolayer. For more detailed descriptions of LDEs and their preparations, see, e.g., Ginsburg et al. (1982), *J Biol Chem* 257: 8216-8227; Maranhao et al. (1993), *Lipids* 28: 691-696; and Favero et al. (2010), *Biol Res* 43: 439-444. The term "LDE" is used herein to refer to one example of a liposome-like nanocarrier or microcarrier that can be used in accordance with the instant invention. Determination of other suitable liposome-like nanocarriers and/or microcarriers is within the routine level of skill in the art.

The term "cholesteryl ester" refers to an ester of cholesterol. For example, the ester bond is formed between the carboxylate group of a fatty acid and the hydroxyl group of cholesterol. Examples of cholesteryl esters include but are not limited to cholesteryl oleate, cholesteryl nervonate, etc.

The term "phospholipid" refers to a class of lipids which are a major component of all cell membranes as they can form lipid bilayers. Most phospholipids contain a diglyceride, a phosphate group, and a simple organic molecule such as choline. One exception to this rule is sphingomyelin, which is derived from sphingosine instead of glycerol. Examples of phospholipids include but are not limited to glycerophospholipid such as phosphatidic acid, phosphatidylethanolamine, phosphatidylcholine, phosphatidylserine, and phosphoinositides (e.g., phosphatidylinositol, phosphatidylinositol phosphate, phosphatidylinositol bisphosphate and phosphatidylinositol triphosphate).

The compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated. For example, the jasmonate compound described herein includes all of any optical isomer that is based on the asymmetric carbon and is optically pure, any mixture of various optical isomers, or racemic form. Examples of stereoisomers of MDJ include, for example, (1R,2R)-dihydromethyljasmonate, (1R,2S)-dihydromethyljasmonate, (1S,2R)-dihydromethyljasmonate, and (1S,2S)-dihydromethyljasmonate. Examples of isomers of methyl jasmonate include cis- or trans-(1R,2R)-methyl jasmonate, cis- or trans-(1R,2S)-methyl jasmonate, cis- or trans-(1S,2R)-methyl jasmonate, and cis- or trans-(1S,2S)-methyl jasmonate.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms, for example, 1, 2, 3, 4, 5, or 6 carbon atoms.

Pharmaceutical Compositions

The present invention also provides pharmaceutical compositions comprising a jasmonate compound and at least one pharmaceutically acceptable excipient or carrier, e.g., a nanocarrier/microcarrier described herein.

In one embodiment, the nanocarriers used for the composition of the invention are formed of cyclodextrins. Cyclodextrins (CDs) are cyclic oligosaccharides formed by D-L (+)-Glucose units linked by a-1,4-C—O—C chains. CDs are produced from starch by means of enzymatic conversion. The native CDs are defined by the number of glucose units, for example, α-, β- and γ-CDs consist of 6, 7, and 8 glucose units, respectively. More examples of CDs suitable for this invention are described in e.g., WO 2010/006392, US 2008/044364, and EP 392608.

In another embodiment, the nanocarriers/microcarriers used for the composition of the invention are LDEs. In particular, the LDE used for this invention comprises phosphatidylcholine, oleic acid, cholesterol, and triolein. Other liposome-like carriers can also be used.

In another embodiment, the nanocarriers used for the composition of the invention are formed of a dendrimer such as PAMAM. The table below demonstrates the size of a PAMAM dendrimer as a function of generations. More examples of dendrimers are described in, e.g., WO 2010/006392.

| Generation | Molecular Weight | Measured Diameter (Å) | Surface Groups |
| --- | --- | --- | --- |
| 0 | 517 | 15 | 4 |
| 1 | 1,430 | 22 | 8 |
| 2 | 3,256 | 29 | 16 |
| 3 | 6,909 | 36 | 32 |
| 4 | 14,215 | 45 | 64 |
| 5 | 28,826 | 54 | 128 |
| 6 | 58,048 | 67 | 256 |
| 7 | 116,493 | 81 | 512 |
| 8 | 233,383 | 97 | 1024 |
| 9 | 467,162 | 114 | 2048 |
| 10 | 934,720 | 135 | 4096 |

In yet another embodiment, the nanocarriers/microcarrier are liposomes (including liposomes targeted to infected cells with monoclonal antibodies to viral antigens). The liposome formulation for the compound of the present invention comprises at least one polymer, oil, at least one tensoactive and a solvent. Those skilled in the art will recognize that any suitable polymer(s), oil(s), tensoactive(s) and/or solvent(s) can be used for the liposome formulation. Determination of suitable liposome formulations for use in to present invention is within the routine skill in the art. Exemplary polymers for liposome formulation include, for example, polycaprolactone, PHB—Polyhydroxybutyrate, PMMA—Poly (methyl methacrylate), chitosane and β-Cyclodextrine. Exemplary oil used for oil phase includes, for example, isodecyl oleate, mineral oil and EMU oil. Exemplary tensoactives include, for example, sorbitan monostearate, lecithin (such as soy lecithin) and polysorbate 80. Lecithin can be any natural and/or synthetic lecithin and/or a mixture thereof. Solvents used for liposome formulation include, but are not limited to, acetone, ethanol and ultra pure water. One non-limiting example of the liposome used for the invention is liposome formed of soy or egg phosphatidylcholine (or lecithin). These can be prepared according to methods known to those skilled in the art, for example, as described in U.S. Pat. No. 4,522,811. Thus, the choices of the exact liposome formulation employed will be influenced by the cancer being treated. Certain liposome formulations will work better for some caners than for others.

In one embodiment, the size of the nanocarriers range from 1 nm to 1000 nm, e.g., 900-1000 nm, 1-900 nm, 1-800 nm, 1-700 nm, 1-600 nm, 1-500 nm, 1-400 nm, 1-300 nm, 1-200 nm, 1-150 nm, 1-100 nm, 1-90 nm, 1-80 nm, 1-70 nm, 1-60 nm, 1-50 nm, 1-40 nm, 1-30 nm, 1-20 nm, 1-10 nm, 1-5 nm, 2-300 nm, 20-200 nm, 50-150 nm, or 3.5-11 nm.

In one embodiment, the size of the microcarriers range from 2 μm to 50 μm, e.g., 2-5 μm, 2-10 μm, 2-15 μm, 2-20 μm, 2-25 μm, 2-30 μm, 2-40 μm, 2-50 μm, 5-20 μm, 5-10 μm, or 7.5-10 μm.

In one embodiment, the jasmonate compound in the pharmaceutical composition is selected from the group consisting of jasmonic acid, 7-iso-jasmonic acid, 9,10-dihydrojasmonic acid, 9,10-dihydro-isojasmonic acid, 2,3-didehydrojasmonic acid, 3,4-didehydrojasmonic acid, 3,7-didehydrojasmonic acid, 4,5-didehydrojasmonic acid, 4,5-didehydro-7-isojasmonic acid, cucurbic acid, 6-epi-cucurbic acid, 6-epi-cucurbic acid-lactone, 12-hydroxy-jasmonic acid, 12-hydroxy-jasmonic acid-lactone, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, tuberonic acid-O-β-glucopyranoside, cucurbic acid-O-β-glucopyranoside, 5,6-didehydro-jasmonic acid, 6,7-didehydro-jasmonic acid, 7,8-didehydro-jasmonic acid, cis-jasmone, dihydrojasmone, and a lower alkyl ester thereof. Preferably, the composition of the invention includes methyl dihydrojasmonate. Other examples of the jasmonate compound suitable for the invention can be found in, e.g., WO 02/080890 and Gfeller et al. *Sci. Signal.* 2010, Vol. 3, Issue 109, pp. cm3.

In one embodiment, the composition of the invention has a concentration of a jasmonate compound (e.g., MDJ) ranging from 1 nM to 100 mM, e.g., 1 nM to 99 mM, 1 nM to 90 mM, 1 nM to 80 mM, 1 nM to 70 mM, 1 nM to 60 mM, 1 nM to 50 mM, 1 nM to 40 mM, 1 nM to 30 mM, 1 nM to 20 mM, 1 nM to 10 mM, 1 nM to 5 mM, 1 nM to 1 mM, 1 nM to 900 μM, 1 nM to 800 μM, 1 nM to 700 μM, 1 nM to 600 μM, 1 nM to 500 μM, 1 nM to 400 μM, 1 nM to 300 μM, 1 nM to 200 μM, 1 nM to 100 μM, 1 nM to 90 μM, 1 nM to 80 μM, 1 nM to 70 μM, 1 nM to 60 μM, 1 nM to 50 μM, 1 nM to 40 μM, 1 nM to 30 μM, 1 nM to 20 μM, 1 nM to 10 μM, 1 nM to 5 μM, 1 nM to 1 μM, 1 nM to 900 nM, 1 nM to 800 nM, 1 nM to 700 nM, 1 nM to 600 nM, 1 nM to 500 nM, 1 nM to 400 nM, 1 nM to 300 nM, 1 nM to 200 nM, 1 nM to 100 nM, 1 nM to 90 nM, 1 nM to 80 nM, 1 nM to 70 nM, 1 nM to 60 nM, 1 nM to 50 nM, 1 nM to 40 nM, 1 nM to 30 nM, 1 nM to 20 nM, 1 nM to 10 nM, 1 nM to 5 nM, 1 nM to 1 mM, 100 nM to 1 mM, 100 nM to 100 μM, 1-100 μM, 10-50 μM, 20-30 μM, 100 μM to 10 mM, 100 μM to 100 mM, 1-100 mM, 1-100 nM, and 59-64 nM.

In one embodiment, the composition of the invention has a concentration of a jasmonate compound (e.g., MDJ) ranging from 100 mM to 1 M, e.g., from 0.2 M, 0.3 M, 0.4 M, 0.5 M, 0.6 M, 0.7 M, 0.8 M, 0.9 M to 1M, 100 mM to 1 M, 200 mM to 750 mM, or about 0.8-1 M.

In one embodiment, when the composition is used for treating leukemia, the concentration of a jasmonate compound (e.g., MDJ) included therein ranges from 100 μM to 5 mM, 100 μM to 4 mM, 100 μM to 3 mM, 100 μM to 2 mM, 100 μM to 1 mM, 100 μM to 0.5 mM, 0.01 mM to about 2 mM, or about 1 mM, 10 μM to 5 mM, 10 μM to 4 mM, 10 μM to 3 mM, or 10 μM to 2 mM. In another embodiment, when the composition is used for treating a solid tumor, the concentration of a jasmonate compound (e.g., MDJ) included therein ranges from 1 nM to 1 M (e.g., 1 nM to 0.5M, 1 nM to 0.1M, 1 nM to 50 mM, 1 nM to 10 mM, 1 nM to 5 mM, 10 nM to 1M, or 1 nM to about 1 mM, or 1 μM to 1M, or 1-1000 nM, 1-500 nM, 1-250 nM, about 1-100 nM, 1-50 nM, 1-10 nM, or 1-5 nM).

The nanocarriers or microcarriers may further contain non-jasmonate molecules or ions in addition to jasmonate compounds. For example, 2-aminoethyl dihydrogen phosphate (or phosphoethanolamine), 3,7-dimethyl-2,6-octadienal (or citral), methyl salicylate, abscisic acid, natural amino acids, $Ca^{2+}$, $Zn^{2+}$, or derivatives or analogues thereof. 3,7-Dimethyl-2,6-octadienal can either be a cis- or trans-isomer. These non-jasmonate molecules or ions can either be associated or coupled with the jasmonate compounds or with the nano/microcarriers. In some embodiments, non-jasmonate compounds can be contained in the same nano/microcarrier as the jasmonate compounds. However, in other embodiments, the non-jasmonate compounds are contained in different nano/microcarriers than the jasmonate compounds, and both these carriers can be administered concurrently. The association or coupling can be created via a chemical bond (e.g., a covalent bond), a hydrogen bond, a van der Waals force, a Coulomb interaction, or the like. In one embodiment, the non-jasmonate compound is encapsulated in the nanocarrier/microcarrier. In another embodiment, the compound is partially encapsulated in the nanocarrier/microcarrier or at the surface of the nanocarrier/microcarrier (e.g., either as a part of the nanocarrier/microcarrier surface or outside yet attached to the surface).

In one embodiment, the nanocarried or microcarried jasmonate compound (e.g., MJ or MDJ) can be synthetically modified, for example, covalently bonded with citral and/or phosphorylethanolamine molecules. Specifically, the reactions can be carried out with any of the carbonyl groups of the jasmonate compound, e.g., the ketone (E1) on the cyclopentyl ring of a jasmonate compound (e.g., MJ or MDJ) or the carbonyl of the ester (E2) of the jasmonate compound. The reaction between the ketone (or ester group) of jasmonate and the amine group (R1) of phosphorylethanolamine can result in the formation of an imine or a hemiaminal (or amide). The yield of the reaction between jasmonate and citral can be improved by first reducing the aldehyde group of citral to form a reduced citral compound ("R2") or hydrating (C-6) double bond to form R3. These preliminary steps result in hydroxyl groups in R2 or R3, which can react with the ketone (E1) of the jasmonate compound to form a ketal or ester, or react with the ester (E2) group of the jasmonate compound to form a new ester.

The reaction among these compounds, i.e., jasmonate (e.g., MJ or MDJ), phosphorylethanolamine R1, citral, R2, and R3, can generate products including, but not limited to: R1-(E1)MJ; R1-(E2)MJ; R1-(E1)MJ(E2)-R1; R2-(E1)MJ; R2-(E2)MJ; R2-(E1)MJ(E2)-R2; R3-(E1)MJ; R3-(E2)MJ; R3-(E1)MJ(E2)-R3 as well as mixture of them such as R1-(E1)MJ(E2)-R2; R2-(E1)MJ(E2)-R1; R1-(E1)MJ(E2)-R3; R3-(E1)MJ(E2)-R1; R2-(E1)MJ(E2)-R3; R3-(E1)MJ(E2)-R2. In one embodiment, fifteen derivative molecules of methyl jasmonate were synthesized by the methods described above.

A "pharmaceutical composition" is a formulation containing a nanocarried and/or microcarried compound of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed nanocarried and/or microcarried compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the nanocarried and/or microcarried active compound is mixed under sterile conditions with a pharmaceutically acceptable carrier (e.g., nanocarriers/microcarriers), and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient or carrier or solvent" means an excipient, carrier, or solvent that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used herein includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is viral infection.

For any compound (e.g., nanocarried and/or microcarried compound disclosed herein), the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing nanocarried and/or microcarried active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the nanocarried and/or microcarried active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™

(BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the nanocarried and/or microcarried active compound in the required amount in an appropriate solvent with one or a combination of ingredients enumerated above, as required, followed by filtered sterilization. Generally, dispersions are prepared by incorporating the nanocarried and/or microcarried active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the nanocarried and/or microcarried active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the nanocarried and/or microcarried compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the nanocarried and/or microcarried active compounds are formulated into ointments, salves, gels, or creams as generally known in the art.

Pharmaceutical compositions of the nanocarried and/or microcarried active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of nanocarried and/or microcarried active compound calculated to produce the desired therapeutic effect in association with the required pharmaceutical carrier. The specification for the dosage unit forms of the invention are dictated by and directly dependent on the unique characteristics of the nanocarried and/or microcarried active compound and the particular therapeutic effect to be achieved.

The pharmaceutical compositions can be included in a container, pack, or dispenser together with instructions for administration.

The jasmonate compounds used for the composition of the present invention include their salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, diethylamine, diethylaminoethanol, ethylenediamine, imidazole, lysine, arginine, morpholine, 2-hydroxyethylmorpholine, dibenzylethylenediamine, trimethylamine, piperidine, pyrrolidine, benzylamine, tetramethylammonium hydroxide and the like.

It should be understood that all references to pharmaceutically acceptable salts include solvent addition forms (solvates) or crystal forms (polymorphs) as defined herein, of the same salt.

The jasmonate compounds used in the pharmaceutical composition of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The jasmonate compounds used in the pharmaceutical composition of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the nanocarried and/or microcarried compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p1-92, Elesevier, New York-Oxford (1985).

The jasmonate compounds used in the pharmaceutical composition of the present invention can also be their metabolites, such as metabolites obtained from acid and/or basic catalysis, e.g., cis-jasmonic acid, trans-jasmonic acid, hydroxymethyl cis-jasmonates, hydroxymethyl trans-jasmonates, hydroxyl cis-jasmonic acids, hydroxyl trans-jasmonic acids, lactones obtained from transesterification, and the like; metabolites obtained from oxidative reactions, e.g., ketomethyl cis-jasmonates, keto-methyl trans-jasmonates, hydroxymethyl cis-jasmonates, hydroxymethyl transjasmonates, diols obtained from oxidative reactions, stereoisomers (e.g., enantiomers or diastereoisomers) obtained from oxidative reactions, epoxides obtained from oxidative reactions, and lactones obtained from oxidative reactions; dehydration products of methyl jasmonate, jasmonic acid, and dihydromethyljasmonate; and metabolites formed through intra-cellular processes, such as phosphorylation (e.g., via kinase) or any other reaction with receptors (such as AKR2 receptor and G-protein coupled receptors), and interactions with cell organelles. Examples of MDJ metabolites include but are not limited to methyl jasmonate, methyl cucurbate, methyl 7-iso-jasmonate, 2,3-didehydro-MDJ, 3,4-didehydro-MDJ, 3,7-didehydro-MDJ, 4,5-didehydro-MDJ, 12-hydroxy-MDJ, 11-hydroxy-MDJ, 8-hydroxy-MDJ, methyl tuberonate, 12-O-glucosyl-MDJ, 11-O-glucosyl-MDJ, 12-O-glucosyl-MJ, 11-O-glucosyl-MJ, 7,8-didehydro-MDJ, cis-jasmone, dihydrojasmone, methyl salicylate, and abscisic acid.

Additionally or alternatively, other jasmonate-related compounds can be used in the pharmaceutical composition of the present invention, such as those formed from linolenic acid (LA)-derived cyclopentanone- or cyclopentenone based compounds. See, e.g., *Annals of Botany* 100: 681-697, 2007; and *Annu. Rev. Plant Physiol. Plant Mol. Biol.* 1997. 48:355-81.

The pharmaceutical composition including the nanocarried and/or microcarried jasmonate compounds, or pharmaceutically acceptable salts, esters, prodrugs or metabolites thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the composition is an injectable composition. One skilled in the art will recognize the advantages of certain routes of administration.

The dosage regimen is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition. The dosing regimen that can be used in the methods of the invention includes, but is not limited to, daily, three times weekly (intermittent), two times weekly, weekly, or every 14 days. In certain embodiments, dosing regimen includes, but is not limited to, monthly dosing or dosing every 6-8 weeks. In certain embodiments, dosage varies during the treating period. For example, a high concentration of a jasmonate compound (e.g., MDJ) in nano/micro-carriers, ranging from 1 mM to 1 M (e.g., 1-1000 mM, 1-900 mM, 1-800 mM, 1-700 mM, 1-600 mM, 1-500 mM, 1-400 mM, 1-300 mM, 1-200 mM, 1-100 mM, 1-50 mM, 1-40 mM, 1-30 mM, 1-20 mM, 1-10 mM, 100 mM to 1 M) can be administered in the first 3 to 7 days before a lower concentration of the nano/micro-carried compound is administered (e.g., from 100 µM to 5 mM, 100 µM to 4 mM, 100 µM to 3 mM, 100 µM to 2 mM, 100 µM to 1 mM, 0.01 mM to about 2 mM, or about 1 mM, 10 µM to 5 mM, 10 µM to 4 mM, 10 µM to 3 mM, or 10 µM to 2 mM). In another embodiment, when the composition is used for treating a solid tumor, the concentration of a jasmonate compound (e.g., MDJ) included therein ranges from 1 nM to 1 M (e.g., 1 nM to 0.5M, 1 nM to 0.1M, 1 nM to 50 mM, 1 nM to 10 mM, 1 nM to 5 mM, 10 nM to 1M, or 1 nM to about 1 mM, or 1 µM to 1M, or 1-1000 nM, 1-500 nM, 1-250 nM, about 1-100 nM, 1-50 nM, 1-10 nM, or 1-5 nM) for treating cancer. This dosing regimen may be more effective in treating certain type of cancer (e.g., leukemia) than the others. Alternatively, a low dose can be administered first followed by a high dose of the nano/micro-carried jasmonates.

Techniques for formulation and administration of the disclosed nanocarried and/or microcarried compounds of the invention can be found in *Remington: the Science and Practice of Pharmacy*, 19$^{th}$ edition, Mack Publishing Co., Easton, Pa. (1995). In an embodiment, the nanocarried and/or microcarried compounds described herein, and the pharmaceutically acceptable salts, prodrugs, metabolites, or esters thereof, are used in pharmaceutical preparations in combination with a pharmaceutically acceptable excipient, solvent or diluent. Suitable pharmaceutically acceptable excipients include inert solid fillers or diluents and sterile aqueous or organic solutions. The nanocarried and/or microcarried compounds will be present in such pharmaceutical compositions in amounts sufficient to provide the desired dosage amount in the range described herein.

Methods of Synthesizing Nanocarried or Microcarried Jasmonates

The nanocarried or microcarried jasmonate compounds and composition thereof described herein can be prepared with the techniques known in the art or the methods described herein.

For example, when cyclodextrin is used as the nanocarrier, the nanocarried compounds of the invention can be prepared by mixing a jasmonate compound of interest with cyclodextrins in a suitable solution (e.g., an aqueous solution), preferably at elevated temperature. In embodiments of the present invention, the as-formed nanocarriers or microcarriers contain about 1-100 moles (e.g., 1-90 moles, 1-80 moles, 1-70 moles, 1-60 moles, 1-50 moles, 1-40 moles, 1-30 moles, 1-20 moles, 1-10 moles, or 1-5 moles) of the jasmonate compound per mole of the cyclodextrin. More detailed descriptions can be found in e.g., US 2008/044364, EP392608, and WO2007/145663. Cyclodextrin microcarriers can be formed of clusters of cyclodextrin nanocarriers.

As for another example, when LDE (or a liposome) is used as nanocarriers or microcarriers, the nanocarried or microcarried compounds of the invention can be prepared by incubating a jasmonate compound of interest in pre-formed LDEs (or liposomes) in a suitable solution (e.g., an aqueous solution) at a temperature below room temperature (e.g., about 4° C.) and then dialyzing the resulting emulsion with a suitable buffer to obtain the desired LDE-carried (or liposome-carried) jasmonate compound. In embodiments of the present invention, the as-formed nanocarriers or microcarriers contain about 1-100 moles (e.g., 1-90 moles, 1-80 moles, 1-70 moles, 1-60 moles, 1-50 moles, 1-40 moles, 1-30 moles, 1-20 moles, 1-10 moles, or 1-5 moles) of the jasmonate compound per mole of LDE (or liposome).

In one embodiment, the LDE nanocarriers are prepared as follows. A lipid mixture consisting of phosphatidylcholine (e.g., 40 mg), cholesteryl oleate (e.g., 20 mg), triolein (e.g., 1 mg), and cholesterol (e.g., 0.5 mg) is first vacuum dried for 16 h at 4° C. An emulsion of the lipids is then prepared in Tris-HCl 0.01 M, pH 8.0 by ultrasonic irradiation, e.g., using a Branson equipment, model 450A (Ultrasound Arruda, Sao Paulo, Brazil) 125 watts power for 3 hours, under a nitrogen atmosphere, with temperatures ranging between 51 to 55° C. To obtain the LDE in the diameter range or size range desired for encapsulating MDJ, the emulsion is purified in two steps of centrifugation (e.g., ultracentrifuge, Beckman rotor SW-41). In the first step, the fraction of the upper tube, resulting from centrifugation at 200,000 g for 30 min at 4° C., is removed by aspiration (1 mL) and discarded. Into the remaining suspension is then added potassium bromide (KBr) to adjust the density to 1.21 g/mL. After the second centrifugation (200,000×g for 2 hours at 4° C.), the LDE will be recovered at the top of the tube through aspiration. The excess KBr is removed by dialysis against two changes of 1000 volumes 0.01 M Tris HCl, pH 8. Finally, the emulsion is sterilized by Millipore membrane filtration porosity of 0.22 mm in laminar flow and stored at 4° C. for up to thirty days. The size of the LDE particles in suspension can be determined via light scattering and microscopy measurements. The surface potential of the LDE particles in suspension can be measured in a Zeta Potential Analyzer ZetaPALS equipment (Brookhaven Instruments Corporation) (Lima & Maranhao, 2004).

In one embodiment, incorporation of a jasmonate compound (e.g., MDJ) into LDE carriers is carried out as follows. A 50 mL ethanol solution of MDJ is added into a 500 mL LDE emulsion (such as the one prepared above) to make a mixture having a concentration of 3 mg MDJ per 1 mL. The mixture is stirred at room temperature for 15 minutes, and then incubated at 4° C. for 72 h. The incubated mixture is then dialyzed twice against a 200 mL sterile buffer (e.g., Tris-HCl, 0.01M). The dialyzed emulsion can then be analyzed using GC-MS to determine the quantity of MDJ encapsulated in or coupled with the LDE carriers.

In certain embodiments, the nanoemulsion of the invention is formed of, in addition to the jasmonate compound, one or more ingredient selected from a polymer, such as polymer poly(c-caprolactone) or PCL with an average Mw 65.000, citral, phosphorylethanolamine, sorbitan monostearate (Span® 60), and polysorbate 80 (Tween® 80). The emulsion can be prepared via a method similar to that described by Fessi et al. Drug Des Deliv 4(4): 295-302 (1989). Briefly, an oil/water (O/W) emulsion is made by vigorous stirring of the oil (e.g., 10.0 g) and the active compounds (e.g., MDJ) alone or in a mixture ranging from 0.05 to 0.50 g (internal constituents contained within the carrier) in water (e.g., 400 mL) by using a Ultra-Turrax homogenizer (IKA T10 basic Ultra-Turrax®, Ika-Werke, Staufen, Germany) at, e.g., 15,000 rpm for, e.g., 1 min. Then an organic solution which is prepared by, e.g., dissolving a polymer (e.g., PCL, between 0.2 and 2.0 g) in acetone (400 mL) is poured under moderate magnetic stirring, into the O/W emulsion using a peristaltic pump at 10% (PumpPro TPM 600 55 RPM, Waton-Marlow, Wilmington, UK). After 10 min of stirring, an aqueous solution prepared by, e.g., dissolving 1.0 g of Tween® 80 in water (200 mL) is also poured under moderate magnetic stirring into emulsion phase. Again, a peristaltic pump at e.g., 10% is used. After completing addition, the reaction mixture can be further stirred for, e.g., 10 min. In the last step, the organic solvent is removed and the volume of the nanoemulsion is concentrated to, e.g., 500 mL under reduced pressure (e.g., using a rotavapor such as R-21, Büchi, Switzerland). The second step, i.e., adding polymer solution to the emulsion is optional.

The methods to characterize the nanocarried and/or microcarried compounds include theoretical Qualitative Structure Analyses Relationship (QSAR) applied with HYPERCHEM software using semi-emprical approach. In this sense QSAR is used to estimate the stability of the nanocarried compounds formed of jasmonic acid or methyl dihydrojasmonate and natives cyclodextrins (CDs). In one embodiment, the calculation is performed with AM1 semi-empiric method using Polak-Rabiere conjugated gradient with rms of 0.1 kcal·(angstrom·mol)$^{-1}$.

Qualitatively the measurement of ΔH (=$E_{binding}$) reflexes the lowest of the total energy of the system when formation of nanocarried and/or microcarried compound (i.e., association or coupling between nano/micro-carriers and a jasmonate compounds) occurs.

Therefore, the stability of the reaction represented by $E_{binding}$ can be estimated from the difference between the energy of the nanocarried and/or microcarried compound as formed and the total energy of the nano/micro-carriers and compounds.

Table 1 below shows the results of the $E_{binding}$ calculation for the association between jasmonic acid or methyl dihydrojasmonate and the natives CDs.

TABLE 1

The result of the ΔH of stabilization.

| | Ebinding (Kcal · mol−1) |
|---|---|
| Jasmonic acid-α-CD | −9.63 |
| Jasmonic acid-β-CD | −19.64 |
| Jasmonic acid-γ-CD | −2.02 |
| Methyl dihydrojasmonate-α-CD | 8.44 |
| Methyl dihydrojasmonate-β-CD | −31.35 |
| Methyl dihydrojasmonate-γ-CD | −18.23 |

As demonstrated in Table 1, with exception of the complex between α-CD and methyl dihydrojasmonate, all the other nanocarried compounds are stables. Also, the association between the jasmonate compound and β-CD produce the most stable nanocarried compounds.

Methods of Treatment

The present invention provides methods for the treatment of a disorder the course of which is influenced by abnormal angiogenesis (or an "angiogenesis-related disorder"). The method includes administering to a subject in need of such treatment, a therapeutically effective amount of a nanocarried and/or microcarried compound of the present invention, or a pharmaceutically acceptable salt, prodrug, metabolite, solvate, or stereoisomeror thereof.

As used herein, a "subject in need thereof" is a subject having a disorder in which abnormal angiogenesis plays a part, or a subject having an increased risk of developing such disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

One example of angiogenesis-related disorder is cancer. As used herein, the term "cancer" includes solid tumors as well as hematologic tumors and/or malignancies. Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer (prostate carcinoma or prostate adenocarcinoma, including multiple drug resistant prostate cancer), rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

Other examples of angiogenesis-related disorders include ocular diseases (e.g., age-related macular degeneration or angiogenesis-related disorders of the posterior segment of the eye), cardiovascular diseases (e.g., atherosclerosis), chronic inflammation (e.g., rheutatoid arthritis or Crohn's disease), diabetes (e.g., diabetic retinopathy), psoriasis, endometriosis, and adiposity. See, e.g., *Pharmacological Reviews* 52: 237 268, 2001.

The present invention provides methods for the treatment of an NF-κB-related disorder, such as a viral, bacterial, or fungal infection. The method includes administering to a subject in need of such treatment, a therapeutically effective amount of a nanocarried and/or microcarried compound of the present invention, or a pharmaceutically acceptable salt, prodrug, metabolite, solvate, or stereoisomeror thereof.

As used herein, "treating" or "treat" describes the management and care of a patient for the purpose of combating a disease, condition, or disorder and includes the administration of a nanocarried and/or microcarried compound of the present invention, or a pharmaceutically acceptable salt, prodrug, metabolite, or solvate thereof, to alleviate the symptoms or complications of a disease, condition or disorder, or to eliminate the disease, condition or disorder.

A nanocarried and/or microcarried compound of the present invention, or a pharmaceutically acceptable salt, prodrug, metabolite, or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

All percentages and ratios used herein, unless otherwise indicated, are by weight. Other features and advantages of the present invention are apparent from the different examples. The provided examples illustrate different components and methodology useful in practicing the claimed invention. The examples do not limit the claimed invention. Based on the present disclosure the skilled artisan can identify and employ other components and methodology useful for practicing the present invention.

EXAMPLES

Example 1: Synthesizing LDE-Carried MDJ

A lipid mixture consisting of 40 mg of phosphatidylcholine, 20 mg cholesterol oleate, 1 mg triolein, and 0.5 mg cholesterol was first vacuum dried for 16 h at 4° C. An emulsion of the lipids was then prepared in Tris-HCl 0.01 M, pH 8.0 by ultrasonic irradiation, using a Branson equipment, model 450A (Ultrasound Arruda, Sao Paulo, Brazil) 125 watts power for 3 hours, under a nitrogen atmosphere, with temperatures ranging between 51 to 55° C. To obtain the LDE in the diameter range or size range desired for encapsulating MDJ, the emulsion was purified in two steps of centrifugation (e.g., ultracentrifuge, Beckman rotor SW-41). In the first step, the fraction of the upper tube, resulting from centrifugation at 200,000 g for 30 min at 4° C., was removed by aspiration (1 mL) and discarded. Into the remaining suspension was then added potassium bromide (KBr) to adjust the density to 1.21 g/mL. After the second centrifugation (200,000×g for 2 hours at 4° C.), the LDE was collected from the top fraction of the tube through aspiration. The excess KBr was removed by dialysis against two changes of 1000 volumes 0.01 M Tris HCl, pH 8. Finally, the emulsion was sterilized by Millipore membrane filtration porosity of 0.22 mm in laminar flow and stored at 4° C. for up to thirty days. The size of the LDE particles in suspension was determined via light scattering and microscopy measurements to be 29-400 nm. The surface potential of the LDE particles in suspension was measured in a Zeta Potential Analyzer ZetaPALS equipment (Brookhaven Instruments Corporation) (Lima & Maranhao, 2004) to be between −5.43 mV and −7.42 mV approximately.

A 50 mL ethanol solution of MDJ was added into 500 mL of LDE emulsion prepared above to make a mixture having a concentration of 3 mg MDJ per 1 mL. The mixture was stirred at room temperature for 15 minutes, and then incubated at 4° C. for 72 h. The incubated mixture was then dialyzed twice against a 200 mL sterile 0.01M Tris-HCl buffer. The dialyzed emulsion was analyzed using GC-MS to determine the quantity of MDJ encapsulated in or coupled with the LDE carriers. It was determined that the molar ratio of LDE to MDJ is between 1/10 and 1/5.

Example 2: Synthesizing Soy Phosphatidylcholine Liposome-Carried MDJ and Polymer-Carried MDJ Liposome-Carried MDJ Into a transparent bottle with a lid, adequate amounts of nonionic surfactant castor oil polyoxyethylene-40-Hydrogenated (ORPH) (EUMULGIN® HRE 40) and soy phosphatidylcholine (FS) (Epikuron® 200) with a molar ratio of 1:1 ORPH/FS were added. Sodium oleate and cholesterol were then added with a molar ratio of 1:1 based on a molar ratio of 1:5 sodium oleate/ORPH. The resulting mixture was filtered through a 0.22 μm membrane. The filtered solution was added into a sterile bottle, then MDJ (96%, purchased from Sigma-Aldrich) was added to reach a concentration of 10 mg per 1 mL of the resulting nanoemulsion (this amount could vary from 7 mg to 21 mg of MDJ per 1 mL of the nanoemulsion). The homogenized nanoemulsion was generated via vortex agitation alternating with a resting period. In particular, the mixture in the sterile bottle was sonicated by using Sonic® Ultrasonic Liquid Processor, (model XL2020™ 220 watts), operated in a discontinuous manner, for 20 minutes at room temperature. After sonication, the nanoemulsion was centrifuged at 10,000 rpm for 15 minutes to dispose of the waste released from the titanium rod sonicator. The resulting mixture was dialyzed against a Tris-HCl buffer, pH 7, 2 (aqueous phase). The size of the liposomes of the nanoemulsion was measured to be 50-500 nm. It was also determined that the molar ratio of liposome to MDJ is between 1/10 and 1/5.

Polymer-Carried MDJ/Citral/Phosphorylethanolamine

Poly(ε-caprolactone) having average Mw 65,000, Sorbitan monostearate (Span® 60), and Polysorbate 80 (Tween® 80) were obtained from Sigma-Aldrich (St. Louis, USA). All organic solvents used for were HPLC grade purchased from J. T. Baker (Ecatepec, Mexico). Ultrapure water was produced in-house by Milli-Q System (18MΩ) (Millipore Corporation, Bedford, Mass., USA). Nanoparticles containing citral (3,7-dimethyl-2,6-octadienal), phosphorylethanolamine and/or methyl jasmonate were obtained as follows. First, an oil/water (O/W) emulsion was made by vigorous stirring of oil (10.0 g) and the active compounds, alone or in mixture ranging from 0.05 to 0.50 g, (internal constituents) in water (400 mL) by using a Ultra-Turrax homogenizer (IKA T10 basic Ultra-Turrax®, Ika-Werke, Staufen, Germany) at 15,000 rpm by 1 min. In a second step, an organic solution which was prepared by dissolving a polymer (between 0.2 and 2.0 g) in acetone (400 mL) was poured under moderate magnetic stirring, into emulsion phase using a peristaltic pump at 10% (PumpPro TPM 600 55 RPM, Waton-Marlow, Wilmington, UK). After 10 min of stirring, an aqueous solution prepared by dissolving 1.0 g of Tween® 80 in water (200 mL) was also poured under moderate magnetic stirring into the emulsion. Again, a peristaltic pump at 10% was used. After complete addition, the reaction mixture was further stirred for 10 min. In the last step, the organic solvent was removed and the volume of nanoparticle dispersion was concentrated to 500 mL under reduced pressure (R-21, Büchi, Switzerland). The O/W emulsion made in the first step was stable even without the polymer. Several different nanoemulsions were prepared and analyzed.

Nanoemulsion without polymers containing only one of citral, phosphorylethanolamine, and a jasmonate compound;

Nanoemulsion without polymers containing a mixture of any two of citral, phosphorylethanolamine, and a jasmonate compound;

Nanoemulsion without polymers containing all three compounds, i.e., citral, phosphorylethanolamine, and a jasmonate compound;

Polymeric nanoparticles containing only one of citral, phosphorylethanolamine, and a jasmonate compound;

Polymeric nanoparticles containing a mixture of any two of citral, phosphorylethanolamine, and a jasmonate compound;

Polymeric nanoparticles containing all three compounds, i.e., citral, phosphorylethanolamine, and a jasmonate compound;

All of the nanoemulations showed a high absolute recovery rate (>90%), entrapment efficiency (>85%) and colloidal stability for all active compounds (citral, phosphorylethanolamine and the jasmonate compound such as MJ or MDJ) applied.

Example 3: Synthesizing Cyclodextrin-Carried MDJ

MDJ-cyclodextrin nanoemulsion was prepared by mixing an aqueous or alcohol solution of methyl dihydro jasmonate ($1\times10^{-3}$ Molar to $1\times10^{-2}$ Molar) with a cyclodextrin solution with equivalent amount of cyclodextrin. The resulting mixture was stirred until a homogenous emulsion was obtained.

Example 4: Toxicity Study and a Preclinical Evaluation of Cyclodextrin-Carried MDJ for Treatment of Chemically Induced Colon Tumors in Mice The effect of cyclodextrin-carried MDJ made in Example 3 above was studied in an experimental model of colonic cancer in mice. Apoptosis and cell proliferation, the two most important events related to tumor growth were investigated. The apoptosis and proliferation indexes of colon tumor, adjacent non-cancer tissues and normal colonic tissues were determined. Apoptosis was quantified by apoptotic nuclei counting and CASPASE-3 immunostaining, whereas proliferation was determined by PCNA immunostaining.

Material and Methods

The animals were maintained in agreement with the guidelines of Committee on Care and Uses of Laboratory Animals of the National Research Council of the National Institutes of Health (USA). The mice were fed with food and water ad libitum and maintained on hardwood bedding under a 12-h light/dark cycle. Animals were weighed weekly during the experiments. All experiments were approved by the USP Animal Ethics Committee.

Briefly, Balb/c mice were treated by intrarectal instillations of the carcinogen N-methyl-N'-nitro-N-nitrosoguanidine (MNNG), twice a week for 2 weeks (××), and were sacrificed 24 weeks after the beginning of the treatment. Ten days before the end of the experiment, the animals of group A (n=10) were treated with daily i.p. injections of cyclodextrin-carried MDJ (10 μL of saline solution with 1 millimolar MDJ) for every 60 grams of body weight. The animals of group B (n=10) were treated by daily intrarectal instillations of cyclodextrin-carried MDJ, at the same dosage. The group C (n=10) was treated with MNNG and with daily i.p. injections of MDJ (diluted at 10% in 100 μL of saline). The animals of the group D were treated with MNNG and by daily intrarectal instillations of MDJ, at the same dosage. The control group E was treated with MNNG alone. The control groups F and G were treated with saline and cyclodextrin-carried MDJ, i.p. and i.r, respectively. The control groups H and I received saline and MDJ, i.p. and i.r, respectively. The dosages of cyclodextrin-carried MDJ and MDJ were based on previous animal pilot studies.

The colons were collected and histologically processed for H&E in order to study the histopathological features of the chemically induced tumors and to score the apoptotic index. Colon tumor (T), adjacent non-tumor site (NT), macroscopically normal colonic mucosa from non-tumor rats (N) in the same treatment group were obtained. Immunohistochemistry was performed to study cell proliferation by the Proliferating cellular antigen (PCNA) staining and to analyze cell apoptosis by both the apoptotic bodies counting and by the CASPASE-3 staining. Results were expressed and PCNA labeling index (PCNA-Li), Apoptotic Index (AI) and CASPASE-3 Labeling Index (CASPASE-3-Li). Standard hematology and clinical chemistry parameters were also monitored.

Determination of apoptotic index—Apoptosis was determined by apoptotic nuclei counting. Sections were stained with hematoxylin and eosin to evaluate the number of apoptotic cells per section. The criteria used to recognize apoptotic cells were: shrunk size, loss of contact with surrounding tissues (at times forming the classically described halo) and nuclear condensation as previously described (Yu et al., *Gut* 2002, 51:480-484). At least 1 000 cells were counted in five random fields and the percentage of cells with apoptotic features was then calculated (apoptotic index or AI). The apoptotic nuclei counts were compared with findings obtained by CASPASE-3 immunostaining in 30 randomly selected areas. A strong correlation between apoptotic nuclei count and CASPASE-3 results was found (r=0.83, P<0.001).

Determination of proliferation index—Proliferation was assayed by immunoperoxidase staining for Proliferating Cell Nuclear Antigen (PCNA) as described previously. Briefly, paraffin-embedded sections from each specimen were labeled with PCNA antibody, after microwave antigen retrieval in citrate buffer. Negative controls were run by replacing the primary antibody with non-immune serum. The slides were developed in 3,3-diaminobenzidine tetrahydrochloride (DAB, Dako, Denmark) and counter-stained with Mayer haematoxylin. The proliferation index (PI) was expressed as a percentage of the ratio of PCNA-positive nuclei to the total nuclei counted.

Statistical analysis—Results were expressed as mean±SE. Comparisons among different treatment groups were made by (analysis of variance) ANOVA with Bonferroni's multiple comparison tests. P<0.05 was considered statistically significant. All statistical calculations were carried out using the SPSS statistical software package (version 11.0, SPSS Inc.).

Results

Antitumor Effects of Cyclodextrin-Carried MDJ

Figure 1A:
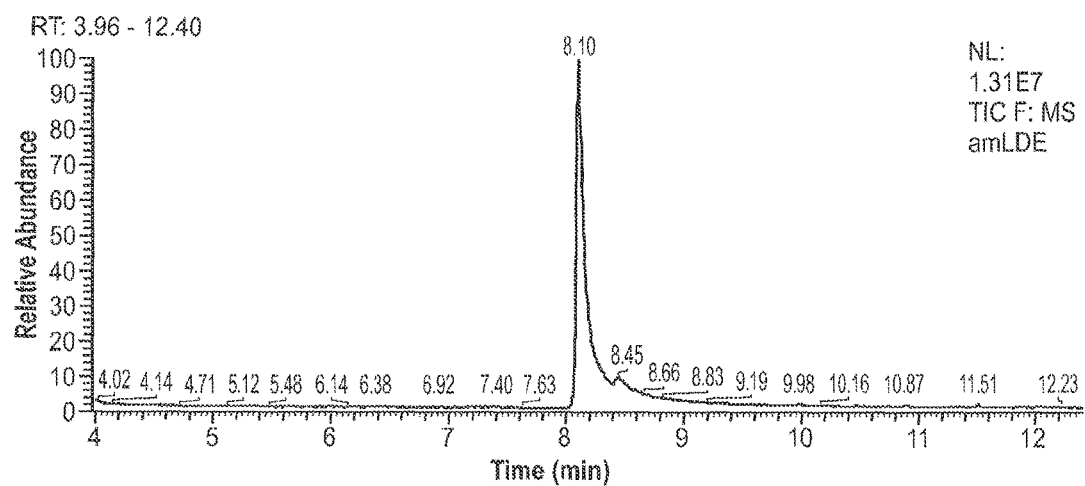
FIGS. 1A-1C: (A) Chromatogram of the MDJ in an LDE; (B) a scanning electron microscopy image of LDE-carried MDJ (an exemplary liposome-carried MDJ); (C) a scanning electron microscopy image of LDE-carried MDJ and amino acids.
Figure 1B:
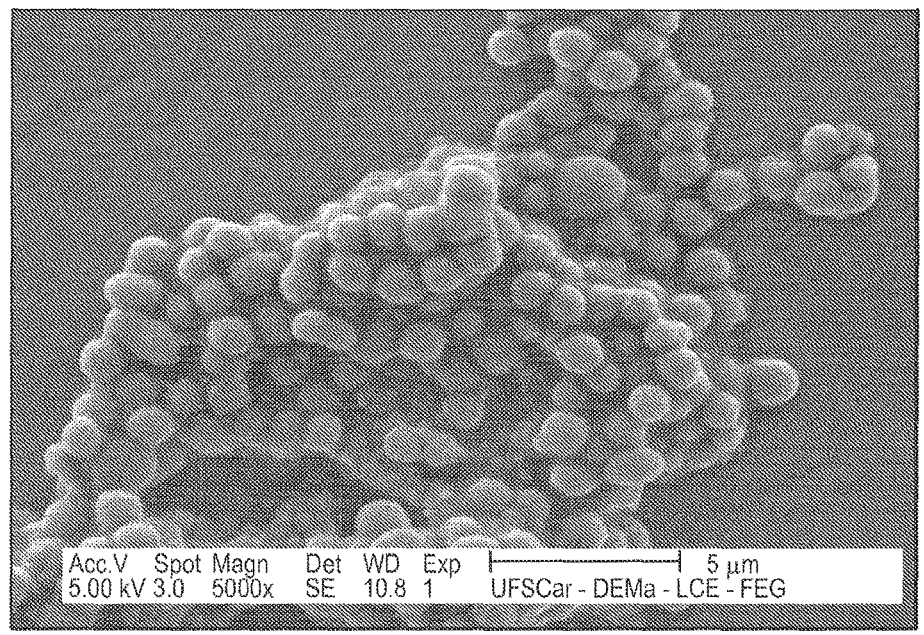
Figure 1C:
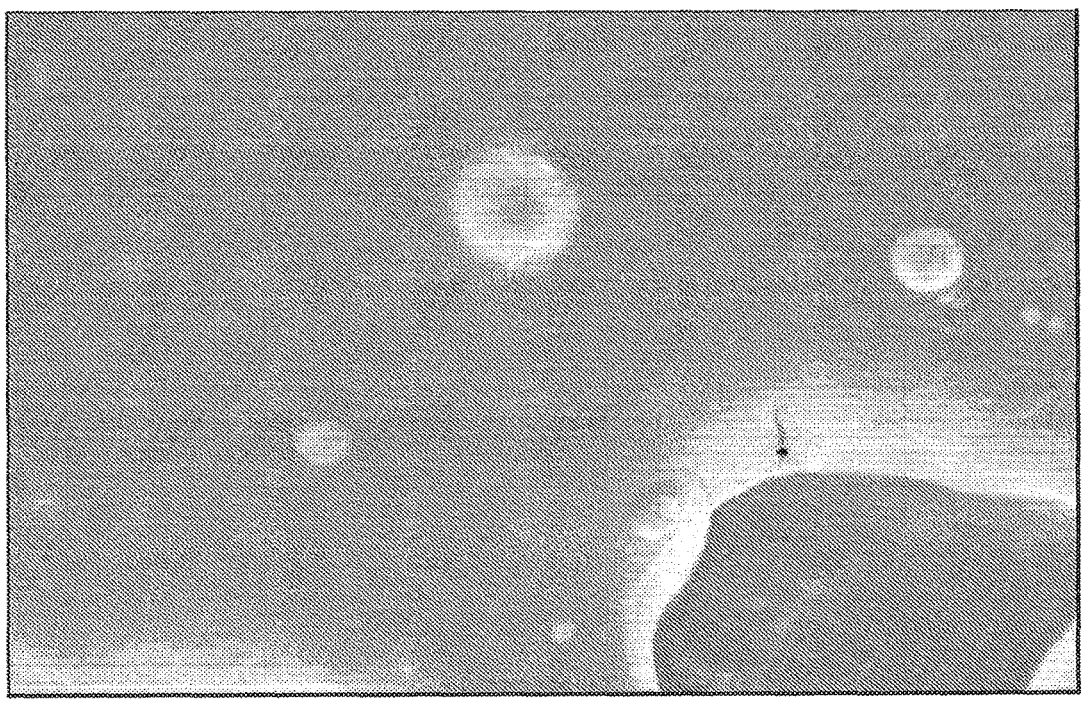
Figure 2:
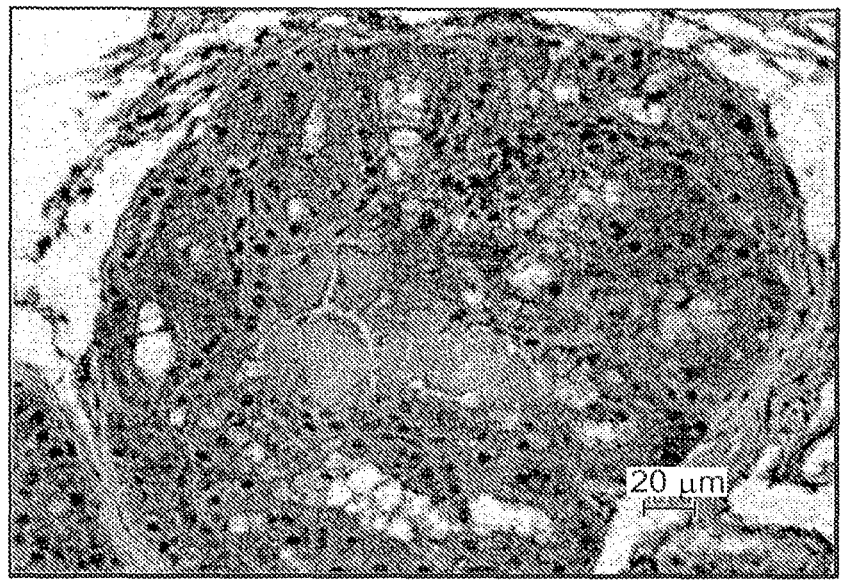
FIG. 2: Intense and homogeneously distributed CASPASE-3 expression in colonic tumor of mouse treated with cyclodextrin-carried MDJ (i.p.)
Figure 3:
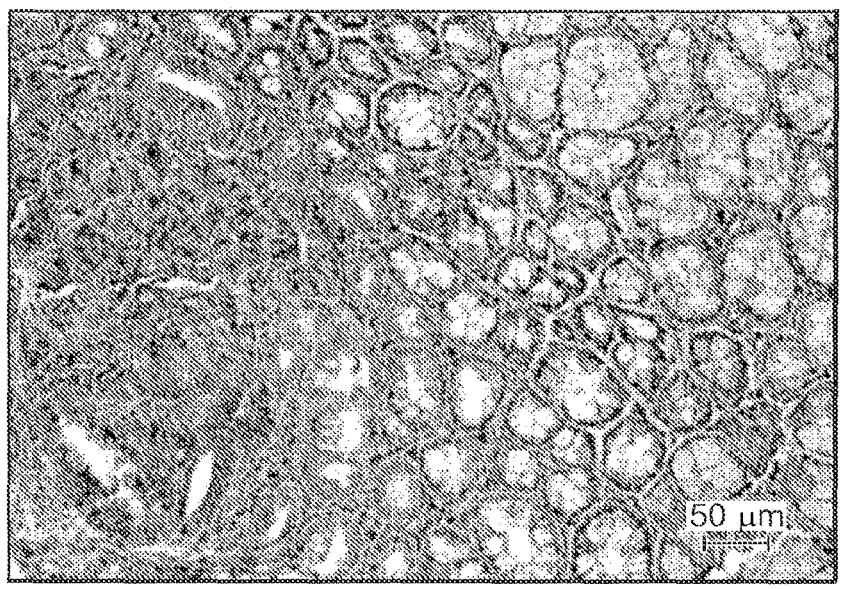
FIG. 3: Heterogeneous CASPASE-3 expression, confined superficially to the epithelium of colonic carcinoma in MDJ-treated (i.r.) mouse.

The experimental groups C and H (that received MDJ i.p.) were discharged due to early signs or peritonitis. All the mice treated with MNNG developed colonic tumors, whilst none of the mice in the control groups developed colonic cancer. There were no statistically significant differences among the groups with regards to the mean number of tumors per mice (4.6) that developed colonic cancer. The apoptotic index was generally higher in colonic tumors than in their adjacent non-tumor and normal colonic tissues (P<0.005, ANOVA). The mean size of the tumors, as well as, the Ai, CAPASE-Li and PCNA-Li in each treatment group is summarized in Table 2 below.

remarkable three fold increase in apoptosis index (accessed by apoptotic bodies counting and CASPASE-3 expression). In this group, the CASPASE-3 expression was intense and homogeneously distributed in the tumors (FIG. 2). However, administration of cyclodextrin-carried MDJ i.r. and MDJ i.r. were associated to a mild, but significant reduction in the above tumor markers, but the histopathological analysis showed that CASPASE-3 expression was confined superficially to the mucosal epithelium (FIG. 3).

Other histological characteristics indicate an increase in immune defenses against the tumors (due to a remarkable increase in number of peri-tumoral lymphocytes, not counted) in the groups A and B.

Both in MNNG-treated animals and in the animals that did not receive the carcinogen MNNG the treatment with MDJ and cyclodextrin-carried MDJ was not associated to any significant changes in cell proliferation and apoptosis in the normal colonic mucosa and in the mucosa adjacent to the tumors.

Absence of Toxic Effects of Cyclodextrin-Carried MDJ

Despite the strong effects of cyclodextrin-carried MDJ in tumors and apart from some signal of behavioral anxiety, there was no observation of any signs of brain, liver, spleen, kidney, gastrointestinal and bone marrow toxicity both in histopathological analysis and in standard hematology and clinical chemistry parameters.

The study evaluated the use of morphological detection of caspase-3 activity as a simple and quantitative technique to measure apoptosis in tissue samples. The proapoptotic enzyme caspase-3 is activated at a point of convergence for the intrinsic and extrinsic apoptosis induction pathways (Nakopoulou et al., *Pathobiology* 2001, 69:266-273). This study aimed to characterize the cell kinetic and apoptotic changes in the colonic tumors and normal mucosa of mice after treatment with cyclodextrin-carried MDJ and MDJ in order to gain more insights into the mechanisms underlying their antineoplastic effects. It has been demonstrated in this study that treatment with cyclodextrin-carried MDJ, but not MDJ was associated to a smaller mean colon tumor size induced by MNNG in mice. It was found that treatment with cyclodextrin-carried MDJ (i.p.) caused a mild inhibition of

TABLE 2

Mean colonic tumors size, PCNA-Li, Apoptotic Index and CASPASE3-Li in the colonic tumors of different treatment groups

| Group | Treatment | Tumor Size ($mm^2$) | PCNA-Li | Apoptotic Index (Tumor) | Caspase-3-Li (tumor) |
|---|---|---|---|---|---|
| A | MNNG + cyclodextrin-carried MDJ (i.p) | 0.41* | 0.22 ± 0.03* | 0.52 ± 1.3** | 0.78 ± 0.19# |
| B | MNNG + cyclodextrin-carried MDJ (i.r) | 0.51 | 0.31 ± 0.05 | 0.21 ± 0.04 | 0.39 ± 0.11 |
| C | MNNG + MDJ (i.r) | 0.56 | 0.41 ± 0.06 | 0.29 ± 0.04 | 0.39 ± 0.11 |
| D | MNNG alone | 0.54 | 0.36 ± 0.06 | 0.18 ± 0.04 | 0.34 ± 0.10 |

*P = 0.03 (groups A vs E) and P = 0.002 (groups A vs D, P = 0.02) - (ANOVA)
**P = 0.03 (groups A vs B, D and E) - (ANOVA)
P = 0.002 (groups C vs B, P = 0.002; groups C vs D, P = 0.004) - (ANOVA)

In summary, the colonic carcinomas in the cyclodextrin-carried MDJ treated animals presented a significant reduction (43%) in the mitotic index accessed by PCNA staining when compared to the E group. Furthermore, the intraperitoneally (i.p.) injected cyclodextrin-carried MDJ caused a proliferation in colonic tumors but not in their adjacent or distant normal tissues. Furthermore, it was noted that only this treatment was associated to a marked induction of apoptosis, also only in tumors but not in normal adjacent of distant colonic mucosa. Intriguingly, a higher proliferation index was found in tumors of the MDJ-treated animals, suggesting that the MDJ may be an irritating stimulus to the mucosa, possibly due to a cytotoxic effect on epithelial cells.

Together, cyclodextrin-carried MDJ treatment resulted in both marked induction of apoptosis and inhibition of proliferation. In contrast, MDJ was found not to inhibit cell proliferation and to induce a mild increase of apoptosis in colonic tumors. These findings suggest that the mechanisms underlying the antineoplastic effect of cyclodextrin-carried MDJ may be more related to its ability to reach all the parts of one given tumor which was not found in the MDJ-treated group and also in the cyclodextrin-carried MDJ (i.r.) group. Importantly, it has been confirmed that the cyclodextrin-carried MDJ inhibitory effects were cancer-specific in the sense that they induced apoptosis in the tumor cells while leaving non-tumor cells unaffected.

The results obtained in this study show that systemically injected cyclodextrin-carried MDJ were able to reach colonic tumors and to reduce the growth of chemically induced colonic tumors without any significant side effect, at least in the experimental conditions performed.

Example 5: Switching Off Cancer by the Cyclodextrin-Carried MDJ

The study described in this Example showed that cyclodextrin-carried MDJ made in Example 3 above induced remarkable shrinking in xenograft human Caco2 tumors in NOD-SCID mice. Furthermore, cyclodextrin-carried MDJ induced vascular disruption, inhibited angiogenesis and cancer stem cells. The microarray analysis showed that the cyclodextrin-carried MDJ influenced simultaneously various important signaling pathways, with major inhibition of NFkB, HIF-1 and metallothioneins. Results were validated by quantitative real-time PCR, western blotting, southwestern histochemistry and immuno-histochemistry.

Male NOD-SCID mice (6-8 weeks old) were injected subcutaneously with Caco2 human colon cancer cells ($1.5 \times 10^6$, in 100 μL of PBS). One week after, the mice were randomly divided into two groups. After 4 weeks, when palpable tumors (20-25 mm$^2$) were established, the group GT was intraperitoneally injected with 100 μL of cyclodextrin-carried MDJ, once a day, for four days and control group was administrated PBS (group GC). Tumor volume was calculated according to the following formula: Length$^2 \times$ Width/2 and tumors were removed at Day 5 after the beginning of the cyclodextrin-carried MDJ treatment. Total RNA from tumors was obtained, quantified and RNA quality was assessed, as described. Gene expression analysis was performed with microarray experiments protocol (Amersham Biosciences, Piscataway, N.J., USA, containing approximately 40,000 probes) (Rizzatti et al., 2005). Quantitative real-time PCR (q-PCR) was performed for the target genes cyclin D1, HIF-1, Metallothionein D3 and VEGFA. The fold change was calculated using 2-ΔCt method. Western blot analysis (WB) was performed for HIF-1 a (Novus biologicals) and NF-KB p-50 (Santa Cruz Biotechnology, Calif.). β-tubulin (clone KMX-1 1:3000, Millipore) was used as a loading control. Southwestern histochemistry analysis (SW) was performed for in situ detection of NF-kB in tumor tissue preparations. H&E sections were used for the histopathological analysis. Immunohistochemistry (IHC) was performed PCNA, cyclin D1; CASPASE-3, CD31, VEGF, CD34, COX-2, TGFβ, HIF-1, CD133, Oct4 and MT. TUNEL assay was also performed. Two investigators, blind to group identification, independently evaluated the samples. Stained cells and microvessel density were scored. Data were analyzed using the statistical program GraphPad Prism 5 (Graph Pad Software Inc., San Diego, Calif., USA) and the analysis was performed by Mann-Whitney test. Probability of $P<0.05$ was considered to be statistically significant.

In addition, it was aimed to verify if it could influence tumor microenvironment, angiogenesis and cancer stem cells (CSCs), which are closely related and currently are considered, respectively, to drive tumor growth and to possess the main resistance system against conventional cancer treatment. Statistical analysis was performed by Mann-Whitney test.

The most notable finding of the study presented here was a remarkable effect of tumor shrinking induced by cyclodextrin-carried MDJ, while the tumors from control animals (GC) presented a significant growth in the experimental period ($P<0.01$) (FIG. 4A). Macroscopically, in comparison to the control tumors, the tumors from the cyclodextrin-carried MDJ-treated animals presented a pale and hard external layer and a softer core, (FIGS. 4B and 4C), suggesting that cyclodextrin-carried MDJ treatment lead to a reduction in tumor blood perfusion.

Figure 4J:
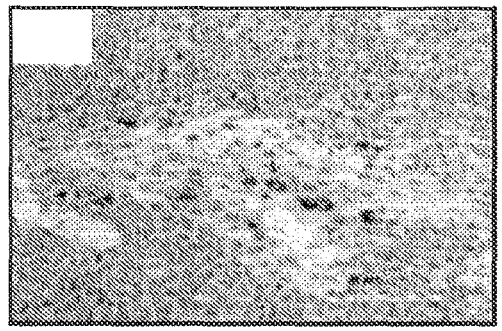
FIGS. 4A-4O: (A) Schematic view of variation of tumor volume, in cyclodextrin-carried MDJ-treated mice (GT) and controls (GC). Note that all treated animals presented a marked fall in tumor volume. (B and C) Macroscopic view of representative tumors at the end of the experiment. The tumors from the cyclodextrin-carried MDJ-treated animals (B) were smaller and presented a pale and hard external layer and a softer core, in comparison to the control tumors (C). Histopathology showed the presence of areas of necrosis (N), which were much larger in tumors from cyclodextrin-carried MDJ-treated animals (E) than in controls (D). Note that necrosis foci were surrounded by concentration of hyper chromatic neoplastic pseudopalisades, which is called "poi-necrotic areas" (PN). The control tumor cells were organized as networking cords of cells (in well delimited lines) closely accompanied by small vessels (black arrows) (F and H). This spatial organization was severely disrupted in cyclodextrin-carried MDJ treated animals, as shown in FIG. 4G, with the presence of blood cells leakage (white arrows) and micro-haemorragic foci (FIG. 4I). CD34 positively immuno-stained cells were present in high number in stroma of the control tumors (FIG. 4J), while the GT tumors presented a marked and statistically significant reduction in the number of CD34 stained cells (FIGS. 4K and 4L). VEGF immuno-staining showed an organized network of vessels in the tumor invasion front area (IF) in control tumors (FIG. 4M). In GT tumors the IF area presented a marked disruption of the spatial organization and a smaller number of positive cells (FIG. 4N). Quantitative analyses has shown a dramatic fall in number of VEGF positive cells in the IF and PN areas in group GT (FIG. 4O). Mann-Whitney test (*p<0.01)

Haematoxylin and eosin (H&E) analysis of xenograft tumors showed prominent vascularity and a division in five types of tissues: (1) Tumor core, with population of round to oval cells that appeared poorly differentiated, hyperchromatic, with a basophilic and scanty cytoplasm; (2) focis of coagulative hemorrhagic necrosis; (3) neoplastic pseudopalisades surrounding necrotic foci, whose were called "peri-necrotic areas" (PN), (4) invasive front at the boundaries of the tumors, and (5) stromal elements usually composed of spindle-shaped cells, grouped in beams and spread both in tumor core and in periphery (FIG. 4J).

Figure 6A:
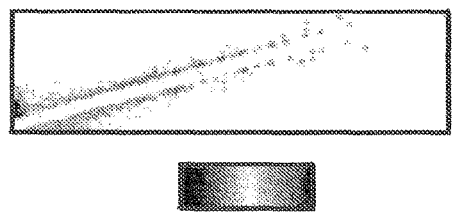
Figure 6B:
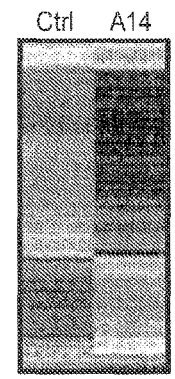
Figure 6C:
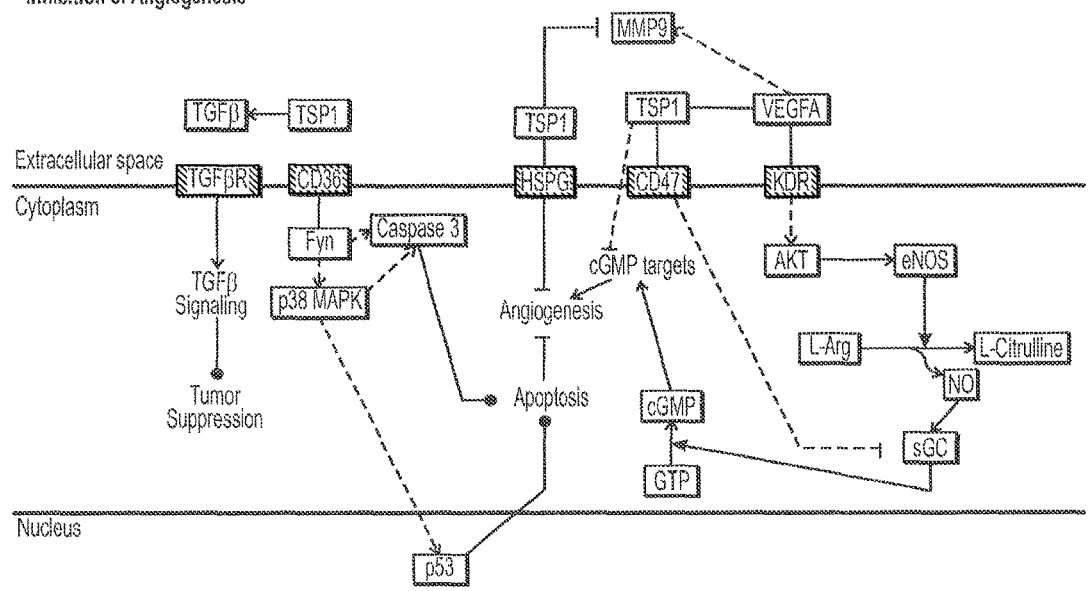
Figure 6D:
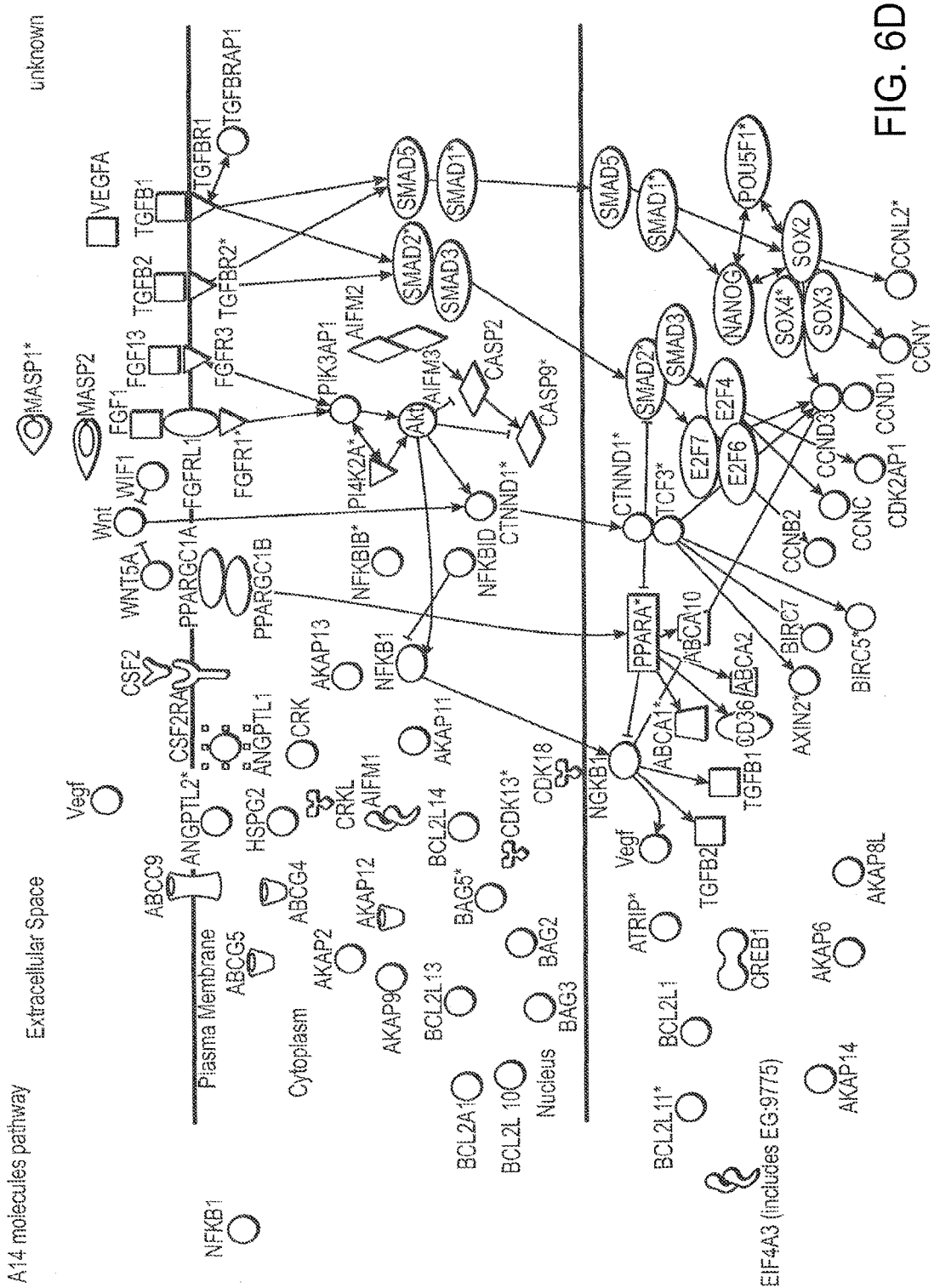

The microarray analysis showed that the cyclodextrin-carried MDJ influenced simultaneously various important signaling pathways (FIGS. 6A and 6B). Of the 40,000 genes in the array, cyclodextrin-carried MDJ treatment caused up-regulation of 2016 genes and down-regulation of 1305 genes (2-26.3 fold). Master transcription factors were altered as well as novel genes of yet unknown function. Summarized in FIG. 2 are the main genes that were up or down-regulated twofold or more in tumors from cyclodextrin-carried MDJ-treated animals, in comparison to the untreated ones. When correlating the most important genes with altered expression and classifying them by the interactions of their gene products, using the Ingenuity Pathways Analysis system, a highly connected network emerged (FIGS. 6C and 6D). No discrepancy was found between the microarray findings and the qPCR (FIG. 6E).

Interestingly, various genes that are known to be associated to anti-cancer effects were found to be up-regulated in cyclodextrin-carried MDJ-treated tumors, as for example, the PPAR. On the contrary, some important genes that are associated with tumor growth were found to be downregulated, like NFkB, VEGF, AKT, HIF-1 and Hox. The gene expression alterations included many pathways linked to angiogenesis, inflammation, apoptosis, matrix metalloproteases, cell proliferation, metabolism and resistance to drugs. The whole range of changes in tumor gene expression by cyclodextrin-carried MDJ can not be described here, but highlights of some of the most important findings related to the mechanisms involved in angiogenesis and cancer stem cells regulation may be presented in conjunction to the morphological data.

Anti-angiogenesis effects of cyclodextrin-carried MDJ—The cyclodextrin-carried MDJ-treated group presented areas of hemorrhagic tumor necrosis, which were 284% larger than those present in the control group GC ($p<0.01$) (FIGS.

4D and 4E, respectively). Furthermore, tumor necrosis apparently occurred mainly from the center of the tumor, rather than from the outside of the tumor on the periphery (FIG. 4E), indicating that not only angiogenesis was inhibited but also that a vascular disrupting phenomenon may have occurred. Indeed, cyclodextrin-carried MDJ impaired endothelial cell (EC) assembly into lumenized and organized blood vessels (FIGS. 4F and 4H), which resulted in the formation of disordered vascular growth, forming lots of apparently dysfunctional vessels with many capillaries ending in a cul de sac (FIGS. 4G and 4I). These observations are in accordance with previous findings of reduction of the vessel density by cyclodextrin-carried MDJ in Chicken Embryo and the budding of new vessels that were leakier and less organized than normal ones (*Braz J Biol.* 2010; 70:443-449).

Figure 7A:
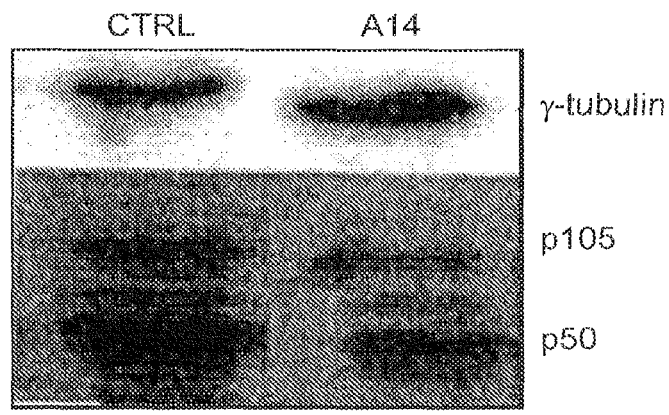
FIGS. 7A-7T: NFkB, TGFβ, HIF-1 and COX-2 expression.
Figure 7B:
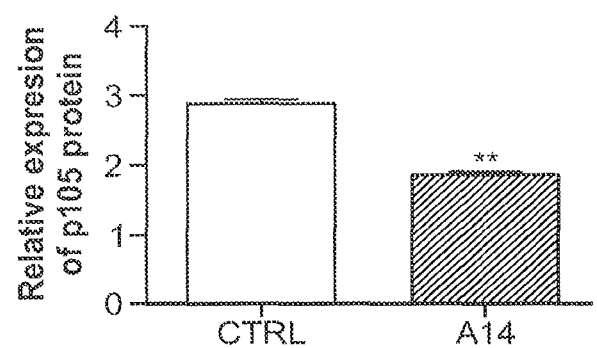
Figure 7C:
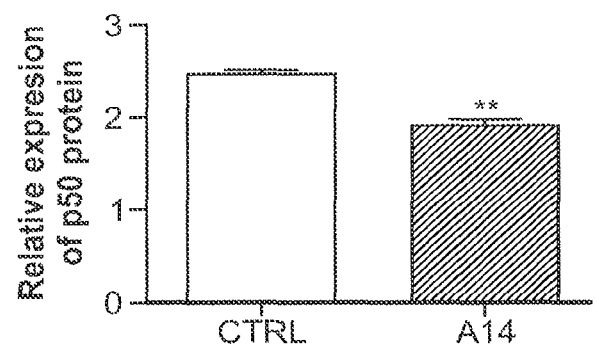
Figures 7D, 7E, 7F:
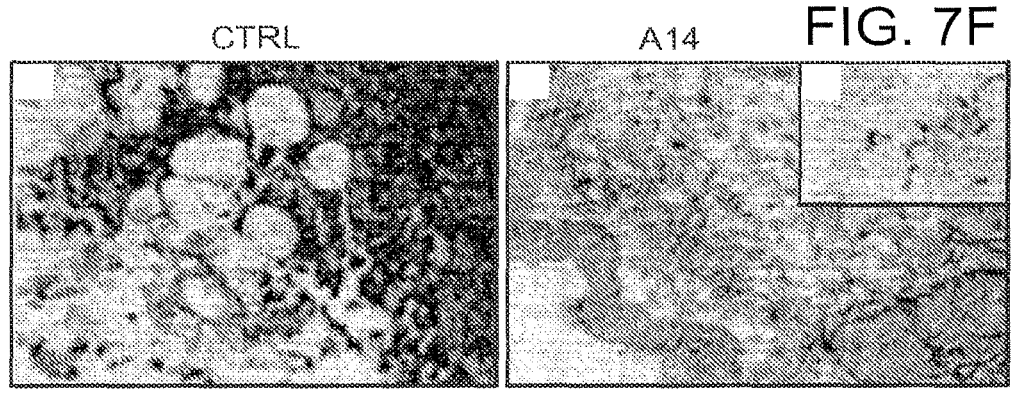
Figure 7G:
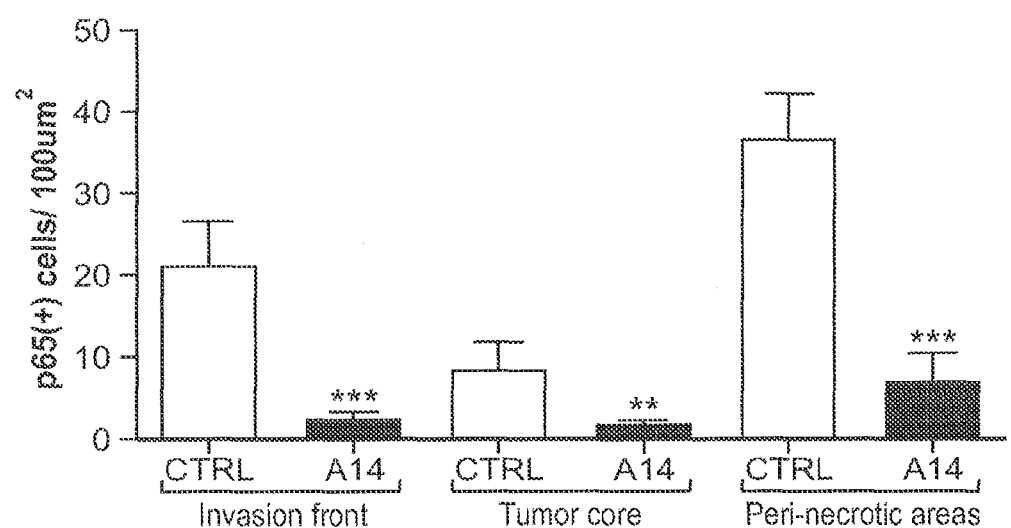

SW showed an impressive and specific increase in the number of blood vessels with specific staining for NFkB in GT tumors (485%; p<0.01), what may represent a mere reactive signaling to cell damage (FIG. 7F). This is also coherent with the observation of a large number of microvessels positively stained for the apoptosis marker CASPASE-3 in GT group. Furthermore, tumors from cyclodextrin-carried MDJ-treated mice contained fewer VEGF and CD31-positive stained microvessels than those from control mice, consistent with the notion that cyclodextrin-carried MDJ can suppress tumor angiogenesis (FIGS. 4N, 4M and 4O).

Figure 4K:
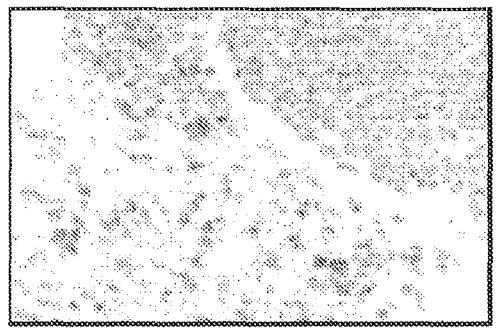
Figure 4L:
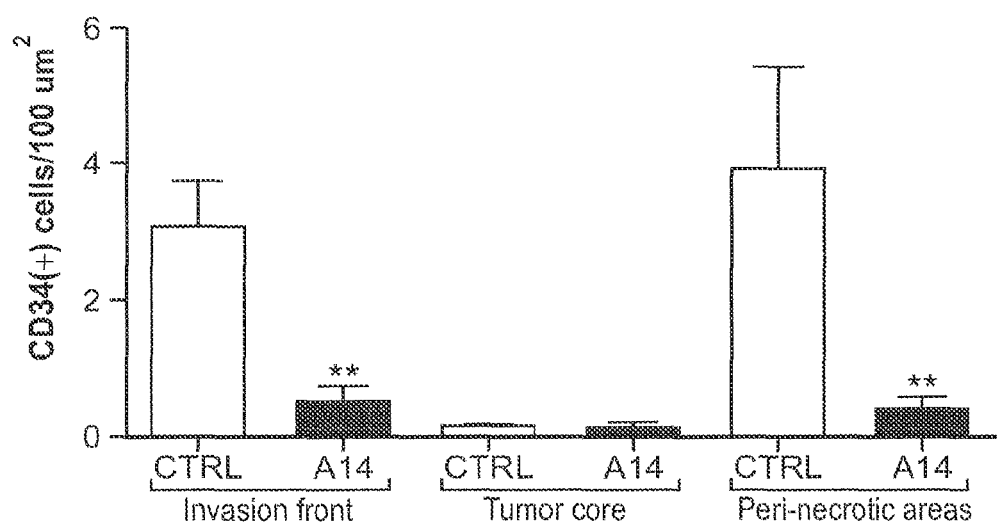
Figure 4M:
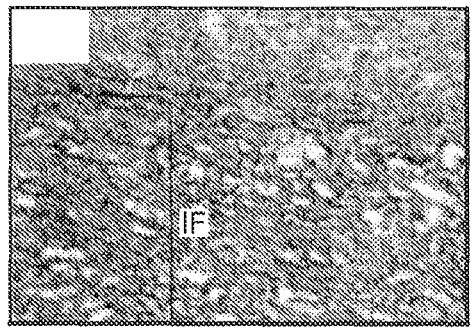
Figure 4N:
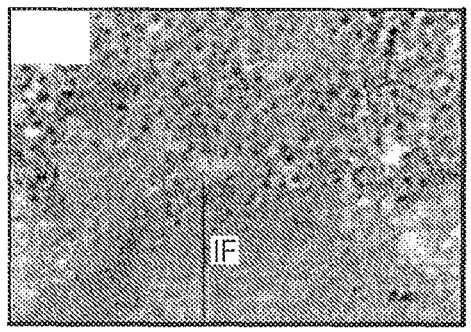
Figure 4O:
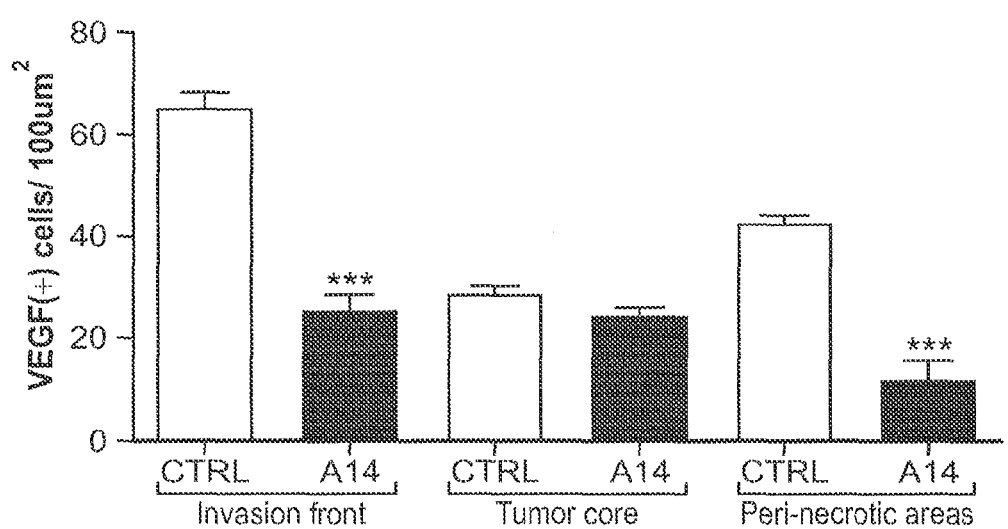
Figure 5A:
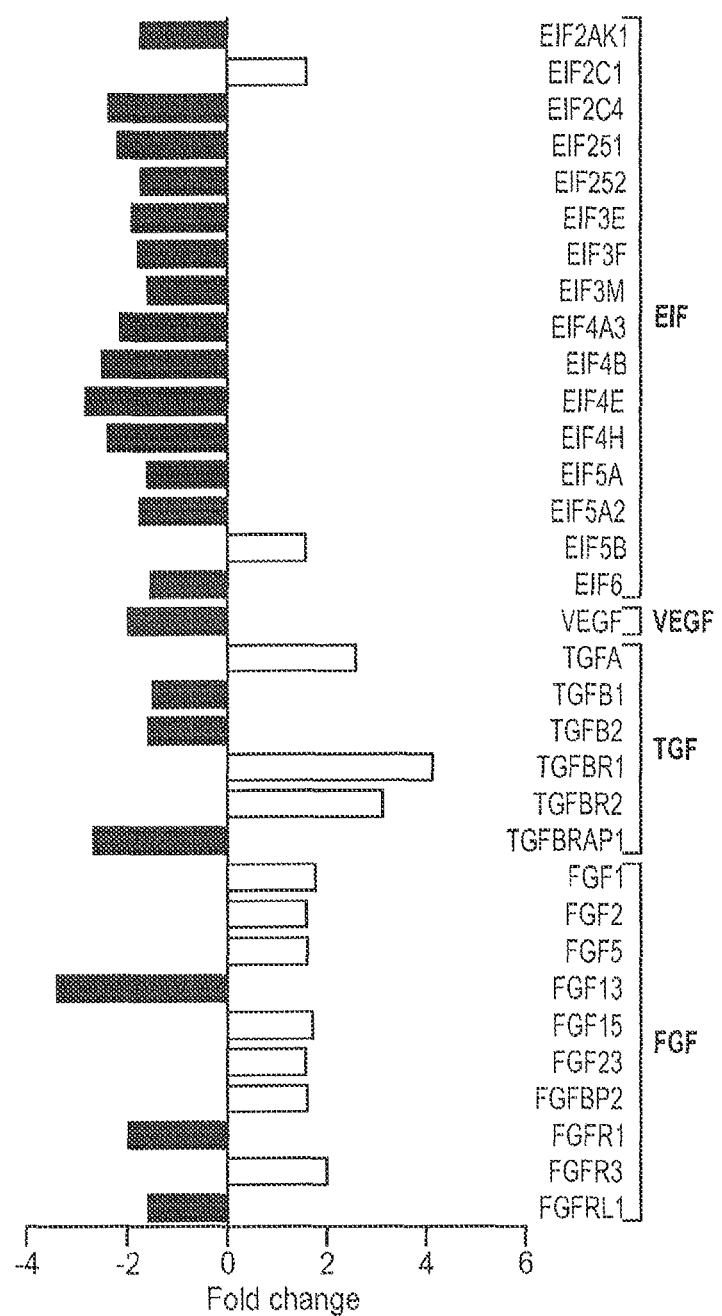
FIGS. 5A-5D: Variation of gene expression in GT and CG tumors. List of the first genes up and down-regulated in cyclodextrin-carried MDJ tumors in comparison to control tumors, as found by microarray analysis. Also shown are the expression patterns of genes that showed at least a twofold variation between the two groups.
Figure 5B:
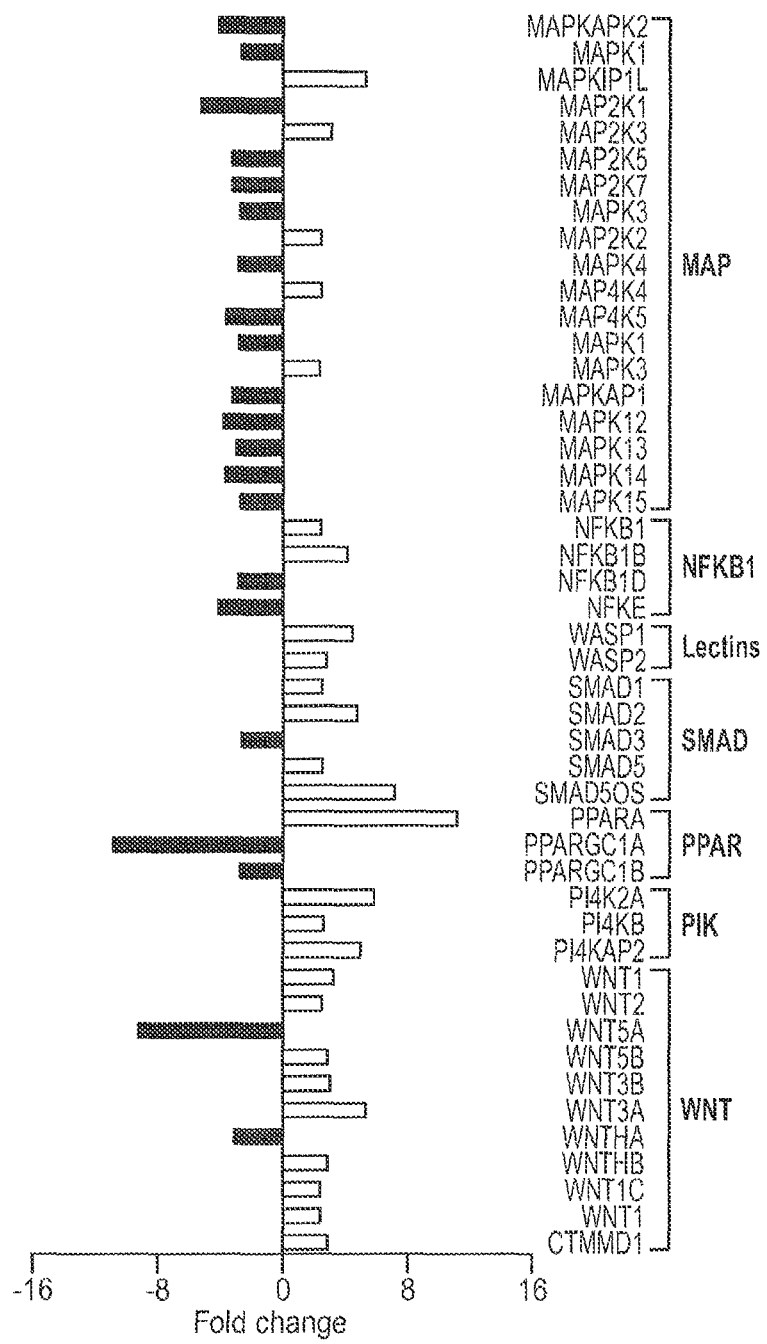
Figures 5C, 5D:
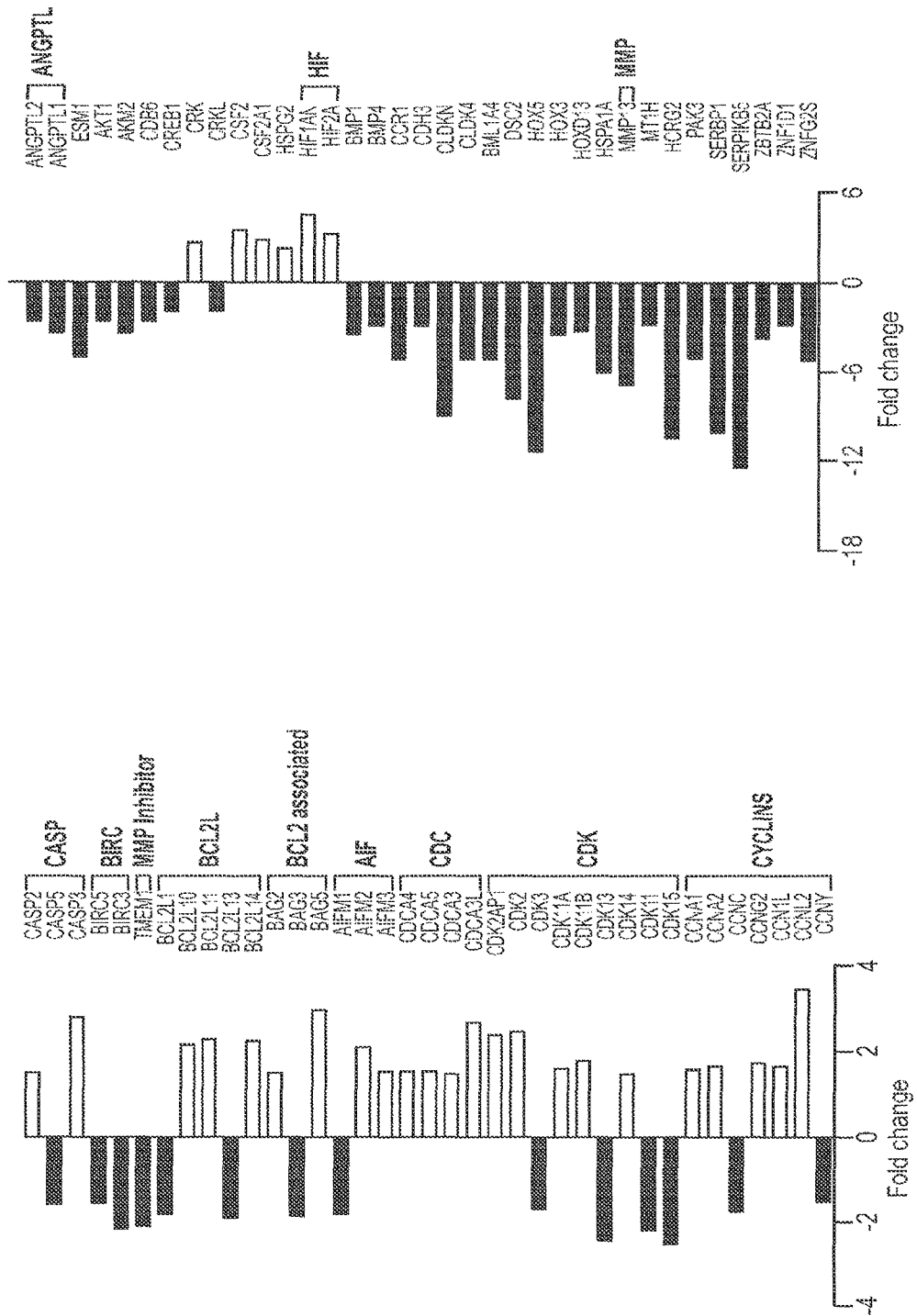

Furthermore, GT presented a significant reduction in the number of cells positive for CD34, a marker of endothelial precursor cells from bone marrow origin (FIGS. 4J, 4K and 4L). This finding validates the MA observation of an downregulation of CCRI (CCL9/15 receptor), that is related to the recruiting of CD34(+) immature myeloid cells (iMCs). A lack of Ccr1 dramatically suppresses outgrowths of tumors in the liver of mice (*Proc Natl Acad Sci U.S.A.* 2010; 13063-13068).

Microarray showed that cyclodextrin-carried MDJ treatment downregulated SAT3 and NF-kB pathway acting upon p65/RelA (Fc −2,524) in accordance with the upregulation of mRNA IkB (2,599), potentiated by a high expression of mRNA TKB1 (NAK) at the nucleus. Both, the WB and SW analysis validated the microarray results by confirming that the levels of NFkB were significantly reduced (FIG. 8). Both NFkB and Stat3 are considered major transcription factors that orchestrate the relationship between inflammation and angiogenesis in cancer progression, by increasing VEGF and other pro-angiogenic factors (*Curr Mol Med.* 2010; 10:369-373).

Figures 7H, 7I:
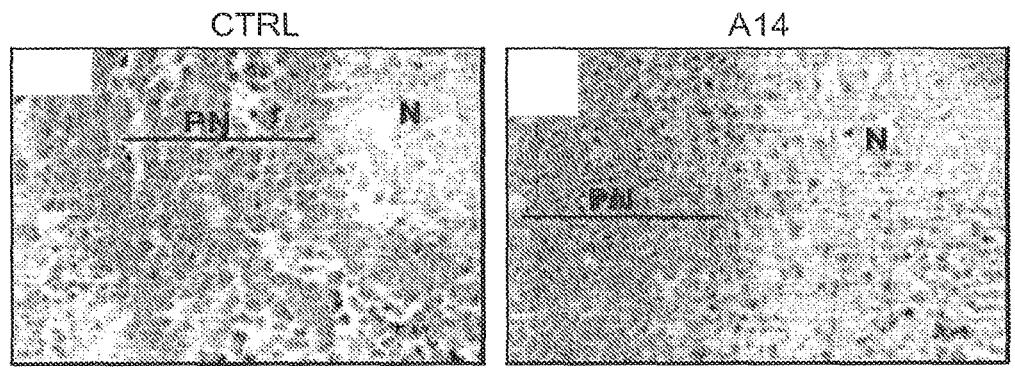
Figure 7J:
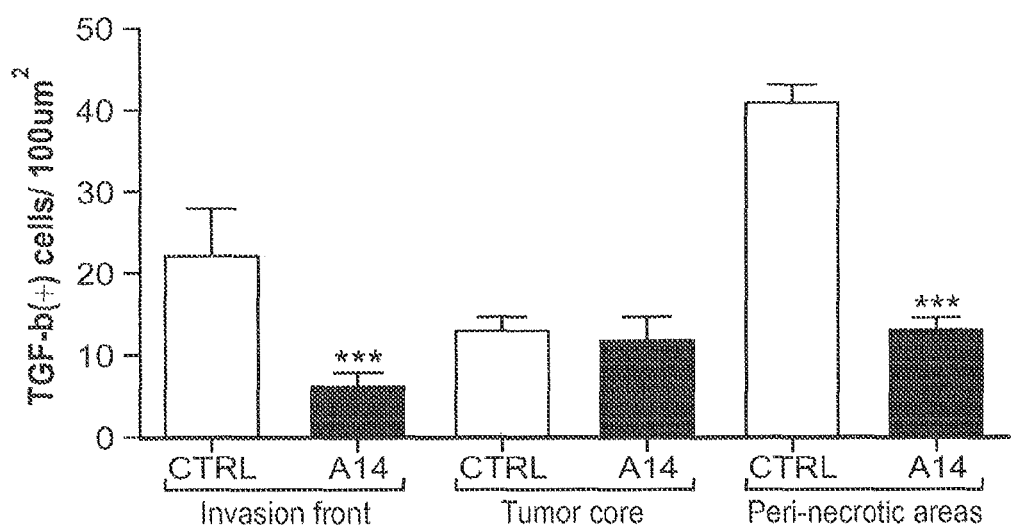

TGFβ was found to be down-regulated in this assay, with an upregulation of TGFBR1 and TGFBR2. TGFβ down regulation in MA analysis was corroborated by qPCR and IHC (FIGS. 7H, 7I and 7J). The regulation of TGFR may be related to the partial changes in regulation of the SMAD complex (activation of SMAD2 and suppression of SMAD3), and activation of E2F7 and suppression of E2F6 and E2F4. This is associated with up-regulation of cyclin-B2 and CDK2AP1, as well as with down-regulation of cyclin-C. TGFβ causes cancer progression through stimulation of angiogenesis, among other mechanisms (Tian et al. Transforming growth factor-f3 and the hallmarks of cancer. *Cell Signal.* 2010).

A marked downregulation of the mRNA HIF1a subunit inhibitor (HIF1AN, FC 3.713) was observed, as well as a downregulation (Fc −2.464) of the Hypoxia Inducible Factor 1 (HIF-1), the key mediator of hypoxia signaling pathways. A downregulation of APEX1 (Fc −2.387) was possibly related to the lower presence of HIF1a and also possibly related to a decreased transcription of the matrix metallopeptidase complex as MMP2 (Fc −3.108) and MMP14 (Fc 3.890). The inhibition of HIF1 may be related to the undetectable mRNA VEGF expression and lower angiogenesis induction (*FEBS J.* 2009: 509-518). It was observed that WB and IHC analysis (FIGS. 7K, 7L, 7N, 7M, 7O) confirmed the microarray and qPCR findings.

Figure 7P:
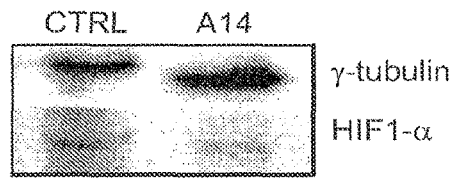
Figure 7Q:
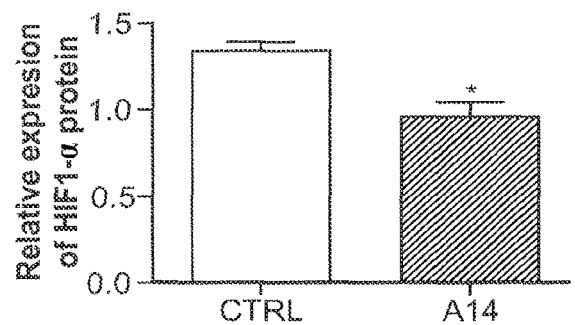
Figure 7R:
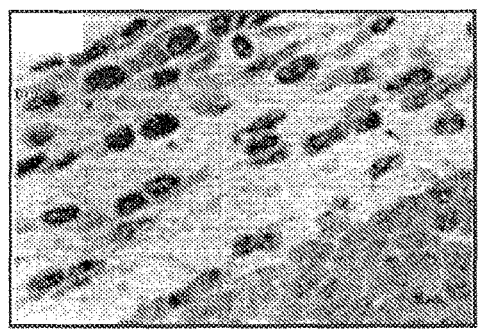
Figure 7S:
Figure 7T:
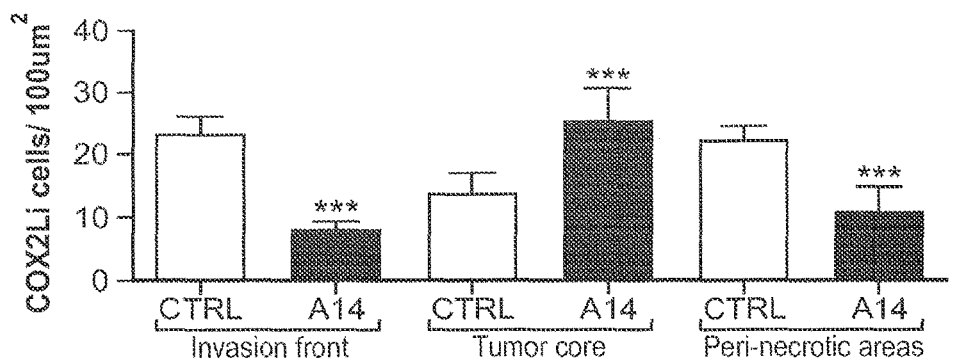

An important increase in PPARa expression (Fc 7.007), possibly related to the undetectable mRNA STATS presence at the nucleus was found. A lack in the mRNA PPAR-gama expression possibly was associated with the absence of transcription factors as c-Fos and c-Jun and this may be responsible for the undetectable COX-2 mRNA presence and what is in accordance with a sharp decrease of COX-2 expression by IHC (FIGS. 7P, 7Q and 7R). An activation of PPARα may be connected with up regulation of CD36 e ABCA1, ABCA2 and ABCA 10. This signaling pathway supports one more mechanism for the cyclodextrin-carried MDJ inhibition of angiogenesis, because PPARs agonists are potent mediators of anti-angiogenesis responses, and PPAR agonists are currently in study as logical options in the treatment of cancer (*PPAR Res.* 2010; 81:4609).

Thus, the vascular disrupting and anti-angiogenesis effects of cyclodextrin-carried MDJ are in accordance with the proposal that targeting multiple pathways is a tendency in anti-angiogenesis therapy, because blocking a single pathway may not be highly effective and tumor cells may either develop resistance against anti-angiogenesis drugs and/or use other angiogenesis mechanisms (*CA Cancer J Clin.* 2010; 60:222-243).

Cyclodextrin-carried MDJ and Cancer Stem Cells—The cancer stem cell (CSM) are the main source of tumor origin (*J Pathol.* 1999; 187:61-81), cell renewal and display increased resistance to the induction of apoptosis by cytotoxic agents and radiation therapy, as compared with the more differentiated cells that comprise the mass of tumors (*Curr Med Chem.* 2008; 3171-3184). Therefore, CSC-directed therapeutic approaches are currently thought to represent relevant strategies to improve clinical cancer therapy (*Curr Med Chem.* 2008; 3171-3184; *J Clin Invest.* 2010; 120:41-50).

Three classical markers of tumor stem cells, correlated with low survival in patients were used in this study: CD133, Oct4 and Metallothionein (*J Pathol.* 2000; 191:306-312; *Ann Surg Oncol.* 2009; 16:3488-3498; *World J Surg.* 2002; 26:726-731; *Mutat Res.* 2003; 533:201-209). In control tumors, it has been observed that the three stem cell markers used were mainly found in the PN areas and in the invasion front of tumors (FIGS. 8A to 8N). The PN areas are also where HIF-1 staining was more intense. Possibly the PN areas are more prone to contain a hypoxic environment and hypoxia activates HIF-1 alpha to enhance the self-renewal activity of CD133-positive cells, driving their transformation to cancer stem cells and inhibiting their differentiation (*Oncogene* 2009; 45, 3949-3959). Interestingly, it was observed that cyclodextrin-carried MDJ was associated with a marked fall in the number CSCs, nevertheless the mechanisms that underlie this finding remain to be fully elucidated. It is less plausible that direct cell necrosis due to vascular alterations could be a major mechanism for it, because CSCs are quite resistant to hypoxic conditions.

Figure 8M:
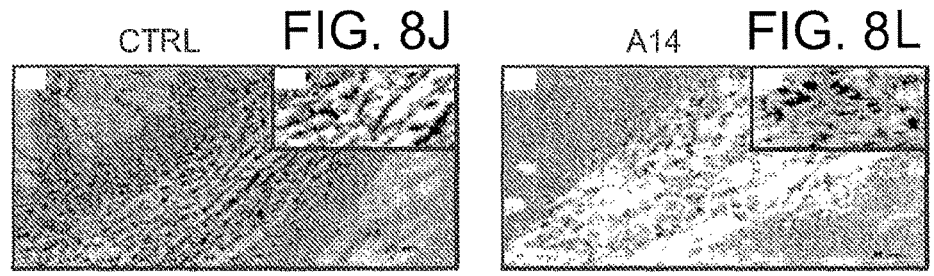
Figure 8M:
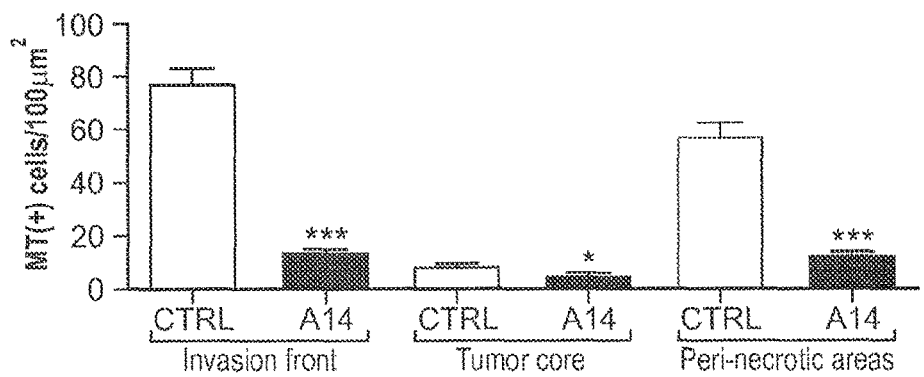
Figure 8P:
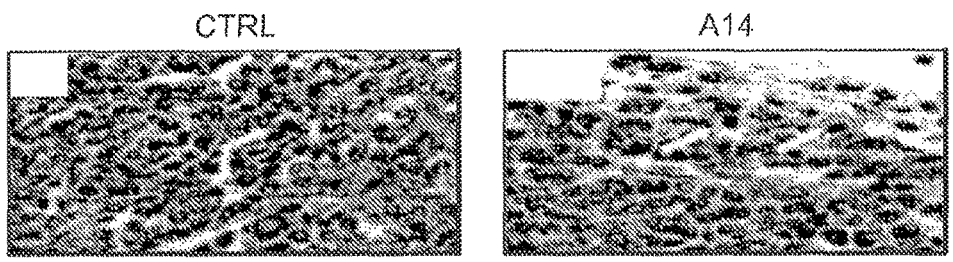
Figure 8P:
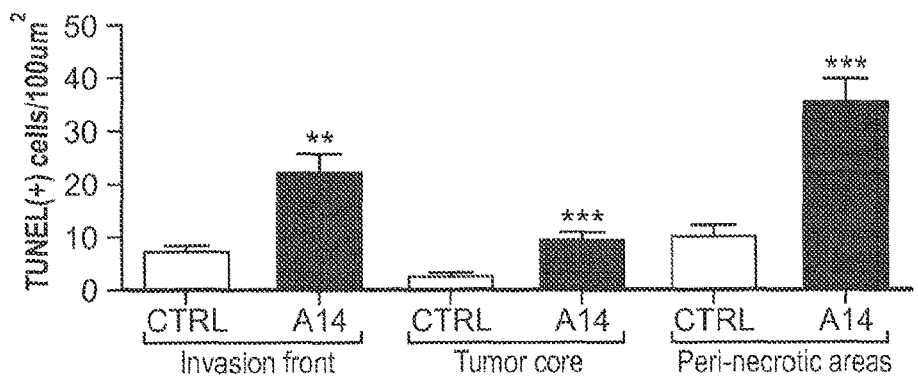

Control tumors showed high number of round metallothionein-over-expressing-cells (MTOEC) in peri-necrotic areas (PN) and spindle-shaped MTOEC lined with the tumor boundaries, organized in cords that interconnect and are closely correlated with the new blood vessels (FIGS. 8I, J, L, N and M). In the present study, the microarray analysis has shown an cyclodextrin-carried MDJ-related fall in MT expression, which was validated by qPCR and IHC. Furthermore, cyclodextrin-carried MDJ also strongly inhibited the appearance and spatial organization of the MTOECs (FIGS. 8I to 8N). This may importantly and negatively influence angiogenesis, because MT has major regulatory functions in the angiogenesis process (*J Cereb Blood Flow Metab.* 2000; 20:1174-1189).

There is a major exchange of signaling between CSCs and endothelial cells (*Nat Rev Cancer* 2007; 7:733-736) and in some tumors CSCs preferentially reside in specific zones adjacent to tumor blood vessels (CSCs niches), or alternatively originate from poorly perfused and hypoxic areas, to which they have adapted (*Nature* 2006; 441:1075-1079). CSCs themselves may produce angiogenic factors and are themselves dependent on factors produced by the vasculature to maintain self-renewal and long-term growth (*Nat Rev Cancer* 2010; 2:138-146). For this reason, novel cancer therapies to target CSCs and their microenvironment have been recently proposed, taking into account that CSCs need a hypoxic niche to protect them from oxidative stress because reactive oxygen species induce p38-MAPK-mediated proliferation leading to CSC exhaustion (*Nat Rev Cancer* 2010; 2:138-146; *Curr. Opin. Hematol.* 2008; 522-528). Based on the findings it can be suggested that cyclodextrin-carried MDJ may also fit well this type of therapy, because it was not only associated with a fall in number of CSC associated to vessels, but also disrupted the spatial organization of MTOEC and new blood vessels, disturbing the CSC niche. It was deduced that it is not inconceivable that the phenotype and biological behavior of CSC might be inverted or switched off by the action of a multi-signaling molecule such as cyclodextrin-carried MDJ.

Cyclodextrin-carried MDJ and apoptosis induction—Tumors from cyclodextrin-carried MDJ-treated mice contained many more apoptotic cells than controls, as shown by the two well known markers of apoptosis, i.e., the TUNEL technique and CASPASE-3. (FIGS. 8O to 8T). Possibly this finding is related to NFkB and HIF-1 inhibition in these areas, because both factors are potent inhibitors of apoptosis. This also may be related to the fall in number of CSCs in these regions. The proliferation index, as reflected by PCNA staining, was not significantly influenced by the cyclodextrin-carried MDJ treatment (P=0.14), despite of an increase in CyclinD1 expression.

Activation of survival/antiapoptotic pathways is a common feature of cancer cells and is related with resistance to cytotoxic agents. The survival pathways implicated in cellular response to drug treatment are primarily PI3K/Akt and Ras/MAPK, which also mediate the signalling activated by growth factors and play a role in the regulation of critical processes including cell proliferation, metabolism, apoptosis and angiogenesis. In our study mRNA AKT1 was downregulated (Fc −2,021) in parallel to a high downregulation of the AKT complex (Fc −2,021; PKBα, PKBβ, RAC, RACα, PKB/AKT). Please fill out and related to a mild downregulation of PI3K complex (PIK3AP1 −1,856; PIK3C3 1,549), possibly due to the activation of GAB complex (GAB1 1,511 and GAB2 1,569), driving the control upon p65/ReIA activation. Up-regulation of FGFRL1 and FGFR1, suppression of PIK3AP1 and FGF13 were related to activation of FGFR3 and in sequence of PI4K2A. Altogether these regulations are possibly related to a down-regulation in PI3K complex (PIK3AP1 −1,856; PIK3C3 1,549), possibly by the activation of GAB complex (GAB1 1,511 and GAB2 1,569) and a reduction of inhibition of expression of caspases 2 and 9, mainly stimulated by the complex AIFM2 and AIFM3. Wnt was down-regulated by WIF1 with marked suppression of Wnt5A.

Furthermore, an important downregulation of the MAPK complex was also observed, mainly for MAP2K1(Fc −3,155), MAPKAPK2 (Fc −2,501), MAPK12 (Fc −2,245), MAP4K3 (Fc −2,153), MAP4K5 (Fc −2,149) and MAPK14 (Fc −2,082). The cyclin complex presented results that might be dependent on the NF-kB complex modulation. Thus, the cyclin complex as D3, A1, and B2 (Fc 3,775; 1,528 and 1,676) were upregulated despite of the downregulation of cyclin C (Fc −1727). At same time, inhibitor complexes were activated as p19 INK4D (Fc 1,871) and p15 INK4B (1,523) in a direct balance to cyclins activation. This was accompanied by a decreased of 13c1 XL (Fc −1,601) commensurate with the tBID and BIM increase as well as upregulation of mRNA BID (Fc 1,505) and finally the high upregulation of Caspase 9 (2,6343) and Caspase 2 (1,530), despite unchanged mRNA Caspase 3 scores. Since SCID mice are immunodeficient, the induction of apoptosis and suppression of tumor growth by cyclodextrin-carried MDJ does not require host immune function and most likely results from the anti-angiogenic or direct tumor cell killing effect of cyclodextrin-carried MDJ.

As this was a short term experiment, it was not possible to evaluate the tumor defensive systems against therapy. Nevertheless, the down regulation of some of the most notably genes related to resistance against chemotherapy, like MT, ABCB4 and HSP70 (HSPA1A) (*Anticancer Res.* 2005; 2661-2668; *Mol Cell* 2009; 15-27), makes it very likely that cyclodextrin-carried MDJ-treated tumors will not present an important resistance against treatment.

Cyclodextrin-carried MDJ and tumor tissue organization—Tumors tissues are usually thought to be completely disorganized, chaotic. Nevertheless, in recent years the argument has been made that malignant tumors represent complex dynamic and self organizing biosystems, capable of developing multicellular collective patterns that resemble evolved adaptive behavior known from other biological systems. This includes collective sensing of environmental conditions and collective decision-making, such as the increasing evidence that collective cell migration is common during invasion of malignant tumors (*BioEssays* 2009; 31:190-197). Thus, another, conceptually new strategy has been proposed, that would be geared toward "interrupting" the cell swarm's information process. That is, if cell-cell communication can be stopped or at least severely hampered therapeutically, arguably the system overall would slow down. It has been observed that in controls, the tumor cells, mainly at the invasion front, usually align themselves into cords (like lines), which communicate with similar structures nearby and around blood vessels, forming anastomosing cords networks (FIGS. 4F and 4H). Interestingly, a tumor tissue "disorganization" was found due to cyclodextrin-carried MDJ's effect. In GT group the tumor cells very frequently lost the cord organization and microvessels were distorted or interrupted and presented leakage of blood red cells, charactering an important loss of tissue cell organization (FIGS. 4G and 4I). It was suggested that cyclodextrin-carried MDJ may also have switched off the organizational tumor signaling system, and this warrants further investigation. Interestingly, microarray analysis has shown downregulation by cyclodextrin-carried MDJ of some important genes that are related to structural organization of tissues, such as Claudin-4 (CLDN4), a transmembrane protein of tight junction structure that is highly expressed in some cancers (*Cancer Sci.* 2009; 1623-1630); EIF4E, that has been considered to be an Achilles' heel for cancer due to the susceptibility of tumor tissues to eIF4E inhibition (*Cancer Res.* 2008; 631-634); DSC2 (desmosomal proteins), recently included in a new set of cell adhesion molecules that might contribute metastasis formation (*Cancer Res.* 2008; 68:6092-6099); MMP13, a matrix metalloproteinase that plays a role in the tumor cell proliferation and invasion (*Oncol Rep.* 2010; 1241-1247); and Wnt-5a, whose increased expression may serve to inhibit activation of the canonical WNT signalling pathway and augment cancer growth (*Br J Cancer.* 2009; 209-214).

Figure 9:
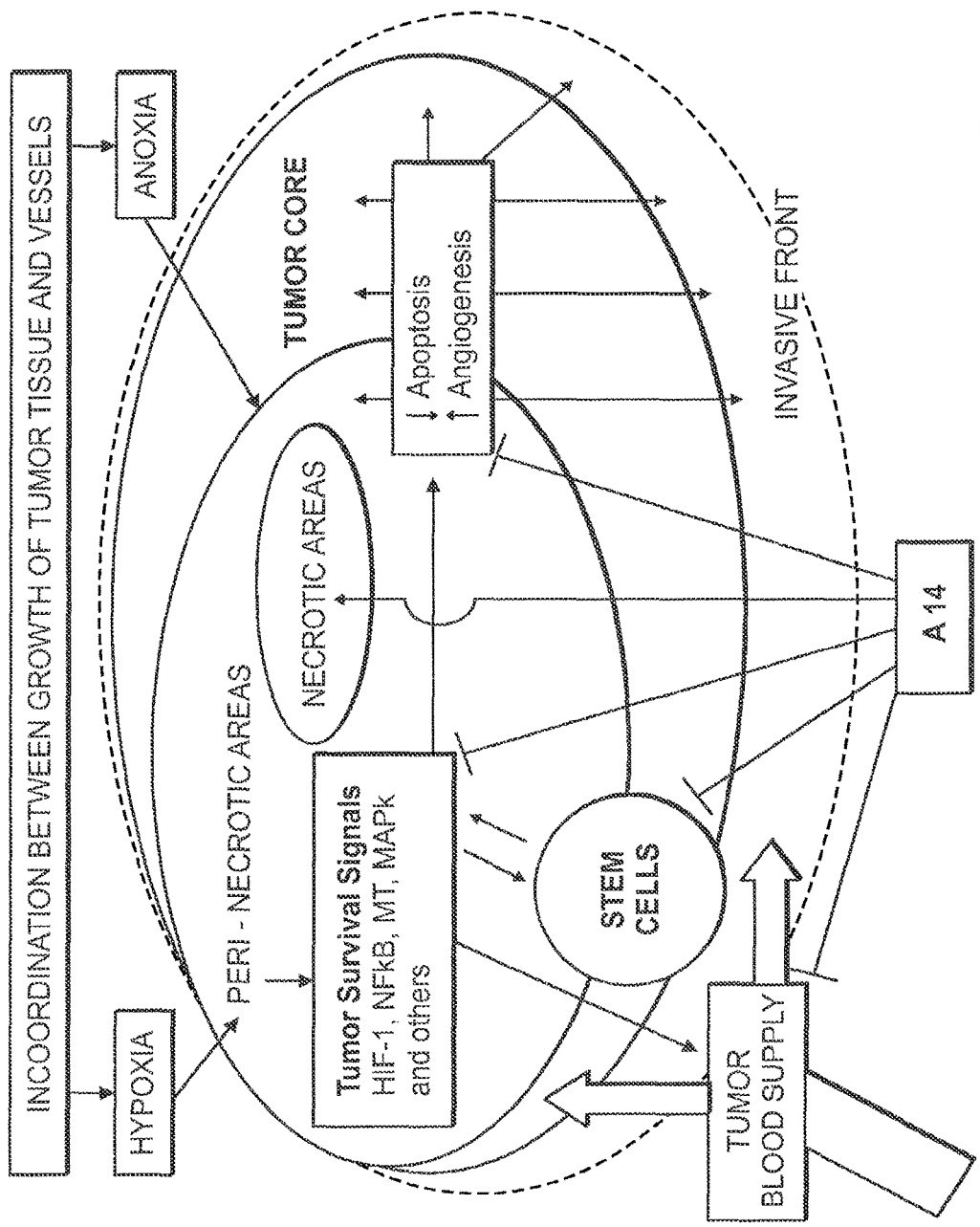
FIG. 9: Proposed model for the role of tumor hypoxia in pumping cancer progression and cyclodextrin-carried MDJ in switching off the tumor signaling systems.

In conclusion, it seems clear that the anti-cancer effects of cyclodextrin-carried MDJ can not be explained by the single target therapy paradigm. To understand the cyclodextrin-carried MDJ effects it is necessary a comprehensive view of tumors as multi-cellular organisms, which adapt their gene responses in a fight for survival, as shown in FIG. 9. The cyclodextrin-carried MDJ effects in this adaptation may shed light on a new paradigm in cancer therapy. JA is genetic regulator. It is extraordinarily conserved in plant evolution species for millions of years and operates in regulating the complex balance between growth and defense responses to an extraordinary range of biotic aggressors, thereby optimizing plant fitness in rapidly changing environments (*Curr Opin Plant Biol.* 2008; 11:428-435).

In FIG. 9, black arrows denote hypoxia driven signals; blue cut lines denote cyclodextrin-carried MDJ blockage of hypoxia driven signals; and blue arrows denote cyclodextrin-carried MDJ induction. During tumor growth, a lack of coordination between the demands of a growing tissue and vascular supply causes insufficiency of oxygen supply in some tumor areas. The most affected ones, which stay in an axonia environment eventually present tissue necrosis. Surrounding these necrosis foci there is the peri-necrotic regions (PNA), with hypoxia, a less intensive lack of oxygen that may permit cells to adapt and survive through intense activation of survival signaling. Thus, we have observed that this region present high expression of NFkB, HIF-1, TGFβ, COX-2. The high levels of these molecules in turn activates Stem Cells phenotypes that also release growth factors that stimulate tissue growth, reduces apoptosis and promotes angiogenesis. For this reason it was fond a high number of positive cells for the classical cancer stem cell (CSC) markers: CD133, Oct4, and MT, with reduced apoptosis indexes (by TUNEL and Caspase-3). So, the PNAs work as signaling factories that stimulates tumor growth and resistance to hypoxia and treatment.

CSCs also accumulate in the Invasive Front (IF) regions and may migrate in close proximity with vessels and support neighbor tissues invasion. The close proximity of CSCs and endothelial cells establishes a paracrine signaling network at the tumor margin, This partnership increases tumor cell invasiveness as the result of stimulation by CSCs and relatively easy blood supply provided by tumor new vessels.

In this theoretical model, the tumor cells in normoxic regions the tumor core stays in a quite moderate metabolism and growth, with a small presence of stem cells and tissue growth factors. These cells provide a type of reserve army. Some of them may switch to CSC phenotype if hypoxia or other aggressions reaches them, but the majority of them may only fulfill spaces by slowly proliferating as tumor advances.

Cyclodextrin-carried MDJ blocks angiogenesis and disrupts existent vessels, what increases hypoxia and this would trigger signals for tumor survival and growth (HIF-1, NFkb, MT, MAPK, stem cells factors). Nevertheless, this is avoided by the fact that cyclodextrin-carried MDJ simultaneously inhibits at least most of these major signaling systems. Thus, the tumor is not able to react to the increased hypoxic conditions and large areas of necrosis replace progressively the tumor tissues, providing optimal conditions for tumor shrinking, until the tumor be virtually eliminated.

When cyclodextrin-carried MDJ is put in contact with tumors, it not only inhibits angiogenesis and induces apoptosis and vascular disruption but also inhibits the major survival signaling systems that are activated by tumors when they present hypoxia and tissue damage. Thus, we have observed that cyclodextrin-carried MDJ caused direct impacts in tumor vasculature, which caused the formation of vast areas of necrosis, and this was combined with inhibition of the tumor defensive signaling systems The reduction in the number of CSCs results in at least two major outcomes. First, the tumor loses possibly its main source of stimulating factors. Second, as CSCs are much more resistant to cancer treatments and hypoxia it is very likely that the tumor may not recover from the first impacts and develop resistance against treatment.

Example 6: In Vitro Angiogenesis Assay and In Vivo Chick Chorioallantoic Membrane (CAM) Assay Cell lines used: non-neoplastic cells derived from human umbilical cord endothelial (HUVEC) and neoplastic cells of melanoma, B16F10 murine tumor. The HUVECs were provided by Dra. Dulcinea Saes Parra Abdalla, Department of Clinical and Toxicological Analyses, FCF-USP's and B16F10 murine melanoma cells, by Prof. Marcia Cominetti Department of Physiology and Molecular Biology of UFSCar. Both strains were grown in RPMI with 10% fetal calf serum. The morphological observation of the two cell types suggested common mechanisms. The preliminary investigation of the effect on angiogenesis was also made in vitro with HUVEC. The measures were undertaken to study the cell cycle by flow cytometry (propidium iodide and acridine orange) the assessment of mitochondrial activity by confocal microscopy (Mitotracker Red), and measurement of VEGF and PGE2 production by HUVEC, we performed cell culture supernatants by ELISA with commercial antibodies.

For the tests with eggs, egg whites were used Gallus gallus incubated in a thermostated incubator at controlled temperature and humidity. The incubation was performed with and without eggs lying giragem. A mark on the upper surface of the bark was used to control this procedure. The eggs were opened on the fourth day of incubation, after careful cleaning of the skin with cotton wool soaked in 70% alcohol. The opening was performed in laminar flow, keeping all your eggs in the same position in which they were hatched, supported on a plastic holder and marked on the upper surface. The experimental procedure was adapted and refined for the project, drawing on the first half of the twentieth century. The description of the method developed The opening was performed with small surgical scissors fine point and curved, forceps micro surgery, transparent tape, a container for disposal, a Pasteur pipette, disposable needles and syringes, a plastic or cardboard for eggs.

The first maneuver performed to open the eggs allowed to obtain an area under the bark. pDesta way, opening a window upper surface can occur without overflowing the contents of the egg remained in the position of observation. A needle BD 25×8 coupled to 3 mL syringe, which was introduced slowly through the air chamber of the egg, an initial angle of 45, was used until approximately the position where, from the suction, is collected only albumin fine. The drilling was done carefully to avoid cracking. Removal of albumin thick, like the yolk or air was avoided, or the withdrawal of the yolk could derail the embryo and remove the air would allow the return of it, jeopardizing the survival of the embryo.

Approximately 5 mL of albumin was removed from each egg into the yolk sac to stay low and be able to open the eggs without the embryo was attached to the bark and visualization of that became possible. Albumin was discarded in the appropriate container, leaving a few milliliters for closing the orifice of the needle insertion. The hole was blocked with its own egg albumin, precipitated with alcohol drip on site. The care and attention to prevent leakage are important to minimize the risk of contamination of the hatchery. If necessary, one more drop of albumin can be put on the hole and drip the alcohol on it until the observation of a membrane on the site.

Using a fine-tipped scissors and curved, the eggshell was punctured carefully next to the brand of graphite, which is the highest part of the face on which the egg was getting heat. After drilling, the bark was cut slowly, avoiding the occurrence of cracks, until the formation of a cut in the shape of the letter "U". At the end, a clamp was used that was introduced in the starting point of the court, complete the withdrawal and the formation of the window. The care in this step was the introduction and manipulation of scissors to avoid damaging the embryo. When the embryo is very young, the shell is harder and observation is more difficult. Moreover, older embryos have the greatest and most CAM adhered to the eggshell, which increases the risk of injury during the procedure. The ideal time for the opening of the eggs was standardized for 4 days of incubation. During this period, the occurrence of loss through injury was avoided and open window in the eggshell allowed easy observation of the embryo and extraembryonic tissues of CAM, with its characteristic arrangement of arteries and veins.

The window was closed with a piece of transparent tape to protect the embryo. The eggs returned to incubation temperature. Time out of the brooder should be minimal, because at this stage of life, embryos do not have the ability to produce heat itself. The proper development depends on environmental conditions of temperature and humidity.

After the opening and closing of windows all eggs were replaced in the incubator, with the same initial conditions and maintained for a further seven days, typically. In this interval procedures were carried out for tests of angiogenesis or for research on tumor growth in vivo. The observation of angiogenesis in eggs inoculated with tumor cells followed virtually the same test model of angiogenesis. Exposure to pure MDJ (cis/trans 96% pure from Sigma) or cyclodextrin-carried MDJ made in Example 3 above was performed on day 8, with the remaining eggs in the incubator until day 14. The inoculation with the melanoma cells was performed on day 4, eggs received MDJ pure or cyclodextrin-carried MDJ on the 8th day and remained incubated up to 14 days. During the development of the protocol, the time of inoculation and treatment were adjusted. Care during the collection and to obtain the images were standardized for all experiments.

By the end of the period stipulated in each test, the eggs were removed from the incubator and cooled in the refrigerator for at least half an hour until the heartbeat of the embryo were no longer observed. After verification of this phenomenon, the tape was withdrawn and dripped CAM with a small volume of 4% formaldehyde. The fixator was maintained for 20 min. Thereafter the membranes were harvested and processed for the fresh. The quality of images obtained depended on the proper preservation of the contents of the vessels were not used or contrast dye injection.

After brief fixation, the hull was breached and the embryo inert placed on a petri dish. The major vessels were tied with cotton thread, with a triple knot, close to the insertion point in the abdomen of the embryo. The CAM was separated then divorced from other tissues, washed quickly with cold saline for removal of waste yolk and spread on a microscope slide, with a minimum of fluid and avoiding the formation of bubbles, cracks or folds in the membrane. The observation was performed after placing a microscope coverslip on the membrane, preventing the formation of bubbles in the liquid film formed. The magnifying glass was adjusted for observation under bright field, no filters and small increase (typically 2× in some instances increases of 5 to 10× were used for observation details). The images were scanned into TIFF files after capture in high definition with the program ACT-2U for a DS-U1 camera attached to a Nikon SMZ1800 stereomicroscopy Magnifier, keeping the same conditions and adjustable lighting, shadow and white balance for each test. In each trial, the image was captured from the fund, kept the lighting and color adjustments in order to standardize the images of the analyzed material. Adjustments were repeated for dark-field images, the same increase.

Each region of the same sample was imaged in bright field and dark field, for better observation of details. The growth of the vascular network was analyzed with the program Image J by processing the images in bright field binary images. The technique allowed the collection of quantitative results did not depend on calculations by combining the images of bright field and dark field, although this possibility has also been studied. This study was important to guide the refinement of one's own collection and preliminary processing of the material. It was then replaced by the analysis algorithm as simple as possible for the construction of binary images. The procedure for processing images of bright field, normalized to the background image in binary images has been refined and standardized. A plugin for Image J was developed, which allows continuous observation of the resulting image during a single adjustment of the threshold of binarization. Each full test was analyzed, according to this common algorithm processing, and the binarization threshold set for each batch of images processed and analyzed in series.

For qualitative analysis and additional documentation, images were obtained with a Canon PowerShot A640 camera coupled to an optical microscope objective Jenamed in increases of 32× 250×.

The typical inoculum was $2 \times 10^4$ cells per egg, in a volume of culture medium less than 10 mL. Melamona growth was accompanied by visual inspection of pigmented mass formation on the CAM, the magnifying glass and microscope. The magnifying glass, the observation of opacities in the dark field image defined the location of the tumor cell growth even when the pigment was still barely visible. Under the microscope, cells were also observed after staining the material not fixed with Thionin or 0.1% toluidine blue. For both dyes, the differentiation with acid alcohol improved the contrast with the normal tissue and allowed the file of the slides. Quantitative analysis of the stained material in this way was not performed, because the dehydration of the material with alcohol changes the vessel diameter and the staining pattern obtained did not show reproducibility and quality of adequate contrast, thus far.

Doses of MDJ and cyclodextrin-carried MDJ, tested in cell cultures, were then incorporated into the model of the eggs, considered the fixed volume of 60 mL per egg.

Eggs used were measured by sampling and the average volume of 60 mL was maintained throughout the period of testing with a standard deviation below 10%. The treatment was done in different ways, according to the interest of the test. For feasibility studies, treatment was carried out at albumin, removed the third day of incubation, before the opening of eggs and maintained at 37° C. until the day of preparation of the solutions and return to the egg, by the same needle hole. The reintroduction of albumin in the egg on the 7th day, was preceded by a new volume withdrawn to avoid an increase in fluid pressure and its extravasation. The tests of viability were monitored for up to 10 days. For studies of antitumor effects, the treatment was done in a single dose on the CAM, the 11th day of incubation. The feasibility of the treatment on the CAM was compared with the viability of treatment by albumin.

The effects on angiogenesis in vivo revealed a new profile in the antitumor action of the cyclodextrin-carried MDJ.

Figure 10:
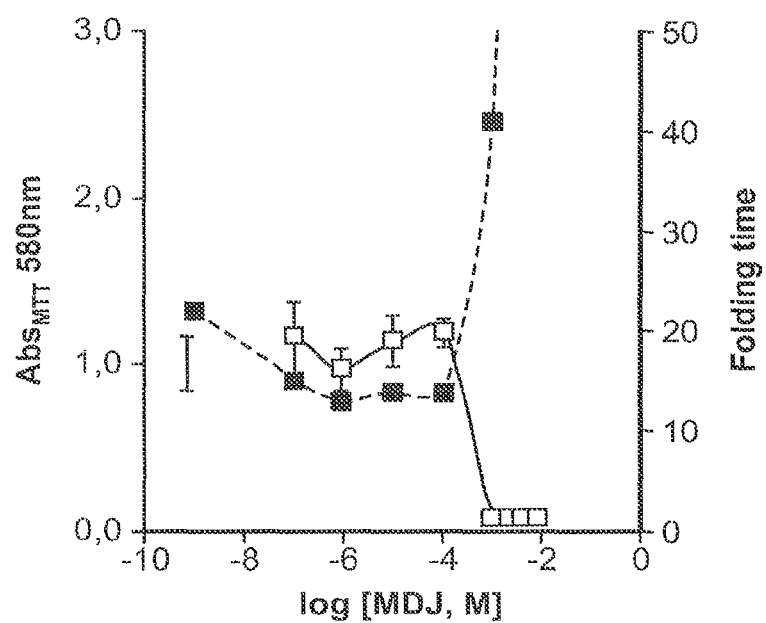
FIG. 10: Effect of MDJ on the growth of endothelial cells (HUVEC, $2\times10^5$ cells/well) in 96-well plates in the presence of serial dilutions of MDJ. Main shaft, hollow symbols: cytotoxicity measured by MTT reduction. Each point represents the average of four readings performed in independent duplicates, except for control, measured in quadruplicate. The measured value for the untreated controls is shown by the corresponding error bar on the graph. Secondary axis, filled symbols: folding time calculated from the cell cultures. Each point represents the mean of three independent experiments.
Figure 11:
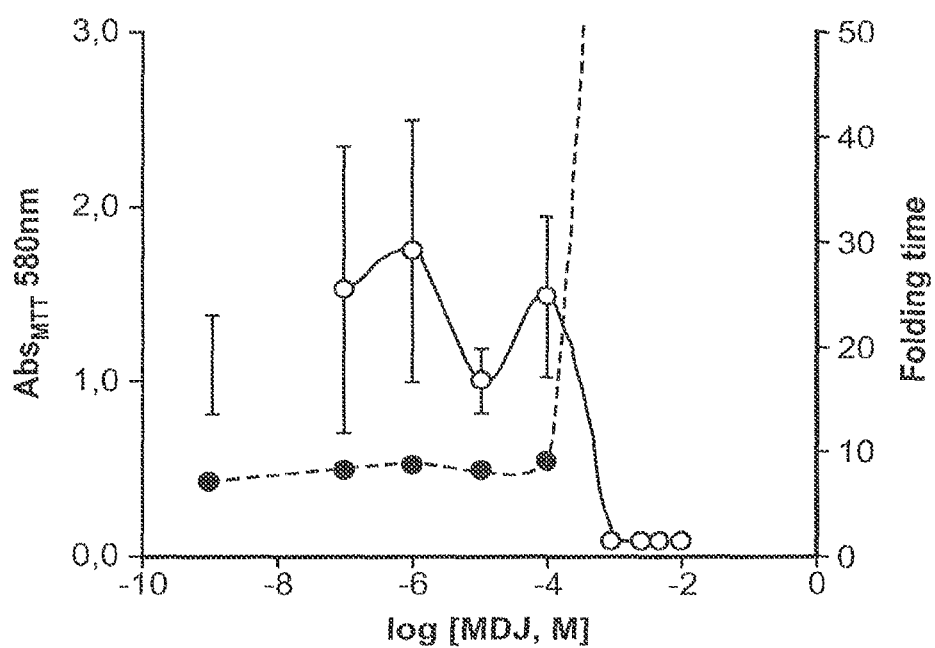
FIG. 11: Effect of MDJ on the growth of murine melanoma cells (B16-F10, $1\times10^4$ cells/well) in 96-well plates in the presence of serial dilutions of MDJ. Main shaft, hollow symbols: cytotoxicity measured by MTT reduction. Each point represents the average of four readings performed in independent duplicates, except for control, measured in quadruplicate. The measured value for the untreated controls is shown by the corresponding error bar on the graph. Secondary axis, filled symbols: folding time calculated from the cell cultures. Each point represents the mean of three independent experiments.
Figure 16:
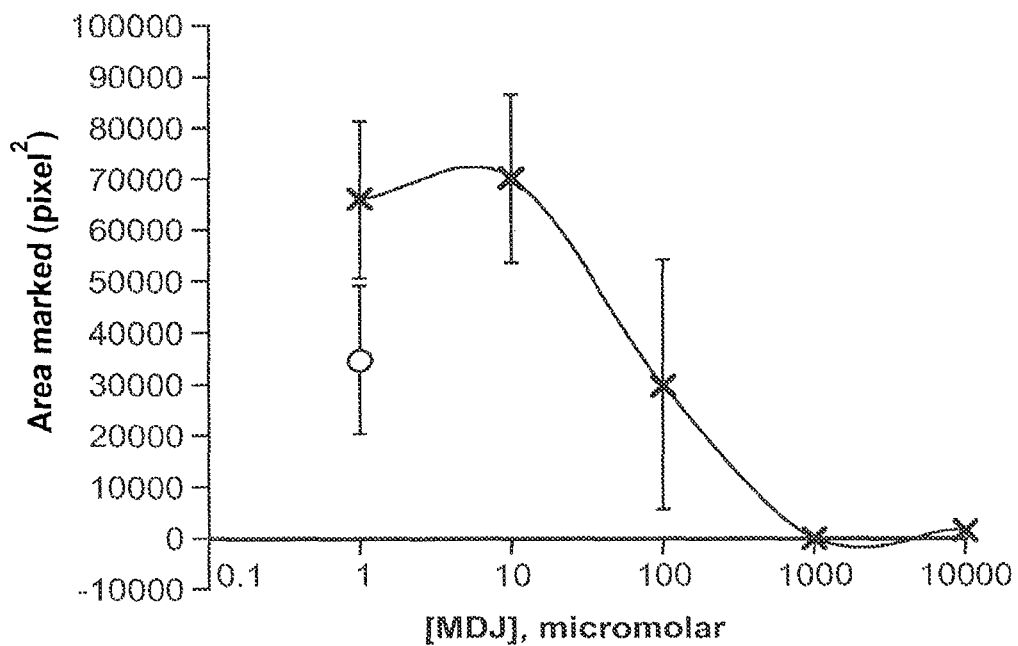
FIG. 16: Effect of MDJ on the mitochondrial activity of endothelial cells after 24 hours exposure in low-density plating on glass coverslips 25 mm in 24-well plates, as measured by Mitotracker Red fluorescence in confocal microscope, 40× magnification. The calibration parameters were maintained for all measurements, each point is the average of six independent measurements. The MDJ was well tolerated by the eggs, when administered in solution in their own egg albumin.
Figure 17:
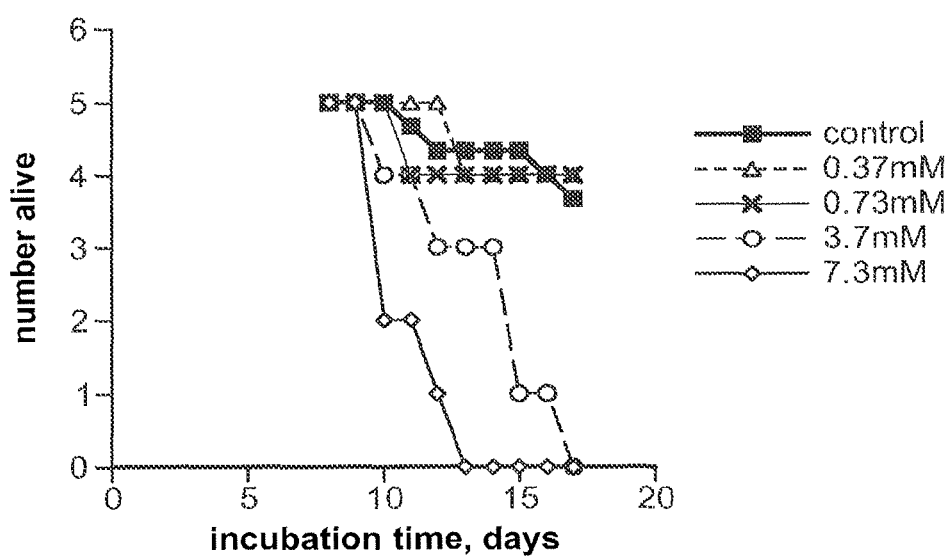
FIG. 17: Toxicity of MDJ in vivo study of survival. The fertilized eggs were exposed to MDJ in doses of 100, 50, 10, 5 μL per egg (n=5) in a volume of 5 mL of albumin removed from the egg itself. The controls were exposed to vehicle without MDJ. The concentrations indicated in the legend were calculated assuming a volume of 60 mL/egg.
Figures 18A, 18B, 18C:
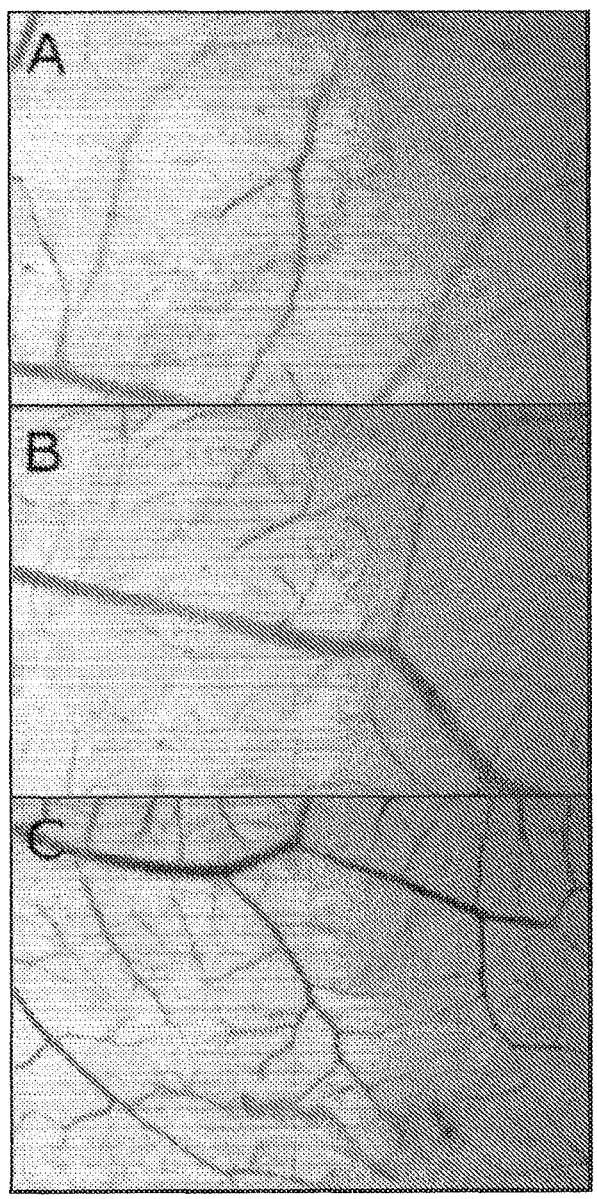
FIGS. 18A-18C: Effect of MDJ added albumin on angiogenesis in CAM model COSES corresponding to the unexposed control (FIG. 18C), 1 uL (FIG. 18B), 5 uL (FIG. 18A) per egg. The presence of melanoma cells decreased the survival of eggs. MDJ partially recovered this survival. The results of CAM in the model confirmed that the bodies of melanoma undergo a dose-dependent involution under the action of the active substance.
Figures 21A, 21B:
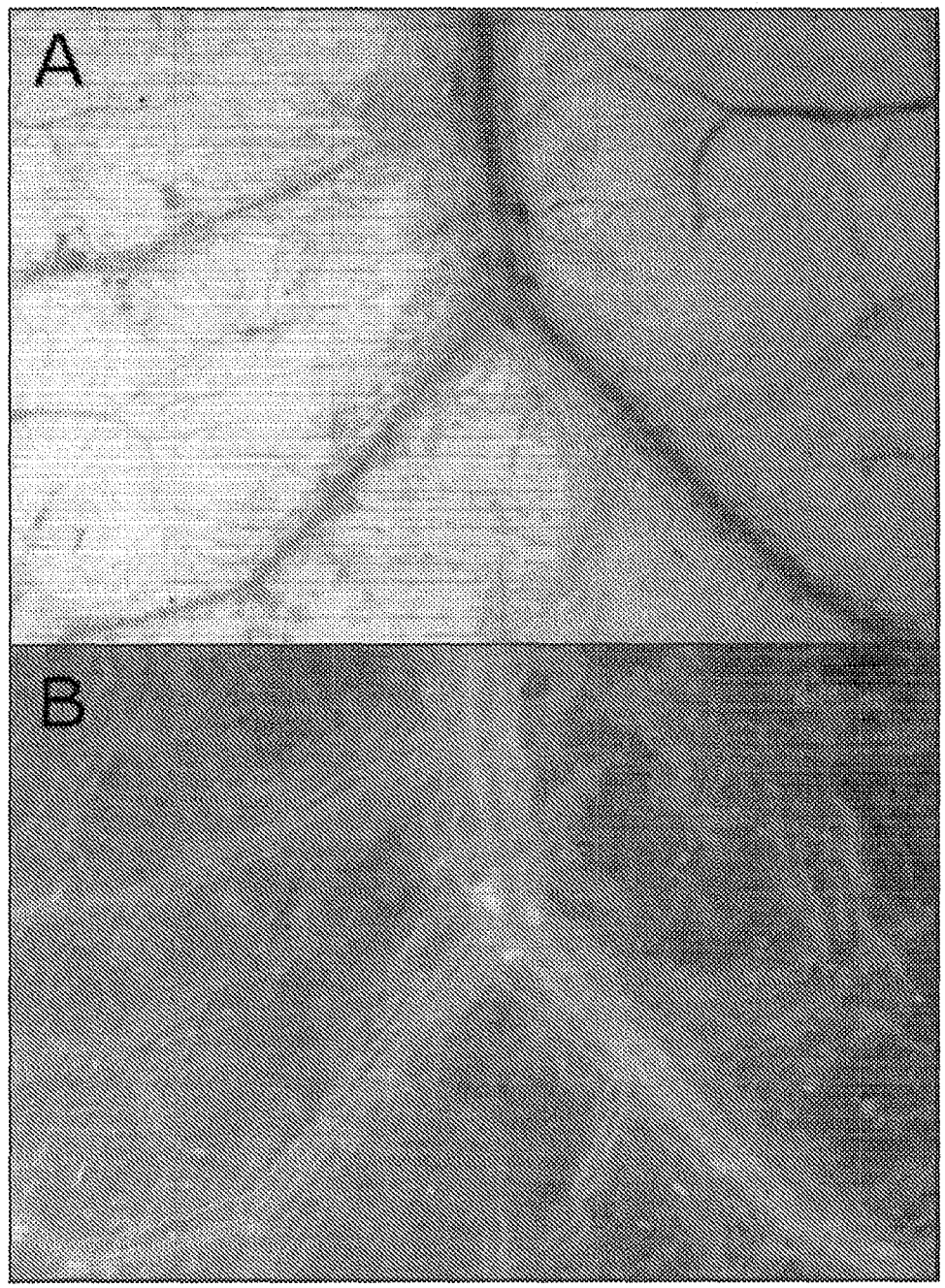
FIGS. 21A and 21B: Effect of MDJ administered albumin on the growth of melanoma in the area of CAM. Sample inoculated with B16F10 murine melanoma, $1 \times 10^4$ cells/well.

The MDJ proved toxic to melanoma cells and HUVEC in the culture. In cell cultures, it was found that the active substance exerted the anti-angiogenic and anticancer effects at concentrations very similar. It was possible to identify very clearly the toxic concentration for each of the cell types (FIGS. 10 and 11). In the toxicity test (MTT), the reduction of the dye, due to the preserved mitochondrial activity was maintained at a constant value at concentrations of less than 1 mM MDJ. This behavior was very reproducible in cell cultures of confluent HUVEC. The growth curves shown, also at concentrations below 1 mM, a folding time constant of about 20 h. At higher concentrations, mitochondrial activity was compromised and the folding time tended to infinity, i.e., the cells stopped dividing and died. In cultures of murine melanoma, the results were very similar, and toxic concentrations were very close.

In toxic concentrations, the MDJ altered cell morphology of the two cell types also leading to the formation of multinucleated giant cells and vacuoles pseudoinclusoes.

These effects on the morphology of MDJ suggested that the induction of apoptosis and autophagy can occur not only in tumor cells but also in the endothelium and led to more detailed study of the cell cycle of HUVEC by flow cytometry (FIG. 13). The new results reaffirmed the hypothesis of a target of toxicity shared between endothelial cells and tumors (FIG. 13 and Table 3).

Additionally, an effect on vascular growth factor, VEGF was demonstrated.

TABLE 3

Effects of MDJ on the cell cycle and the production of VEGF in HUVECs

| MDJ, condition of treatment | Distribution according to the phases of the cell cycle, % (18 h) | | | Marking with Acridine Orange, % (18 h) | VEGF, pg/mL (2 × 10$^6$ cells, 4 h) |
|---|---|---|---|---|---|
| | Dead cells | G0/G1 | G2/S | | |
| Untreated | 6 | 59 | 35 | 6.3 ± 0.1% | 431 ± 67 |
| 10 nM | 93 | 5 | 2 | n.d. | n.d. |
| 1 nM | 13 | 72 | 15 | 6.2 ± 0.1% | 566 ± 31 |
| 100 uM | 8 | 56 | 36 | 6.7 ± 0.3% | 450 ± 30 |
| 10 uM | 7 | 60 | 33 | 9.0 ± 0.5% | 319 ± 12 |
| 1 uM | — | — | — | 12 ± 0.9% | — |

The mitochondria of endothelial cells in culture showed activation in the presence of MDJ. This effect was most evident in the response to MTT in low density plating (FIG. 14). Under these conditions (1×10$^4$ cells/mL) nor at high density plating (2×10$^5$ cells/mL), there was no increase in PGE2 production by HUVEC. The production of PGE2 is normally the confluence of these cells, but could mediate an indirect effect of MDJ.

The toxic effect on endothelial cell proliferation was demonstrated in vitro and in vivo in the CAM model.

The presence of melanoma cells decreased the survival of eggs. MDJ partially recovered this survival. The results of CAM in the model confirmed that the bodies of melanoma undergo a dose-dependent involution under the action of the active substance.

Tests on the Cyclodextrin-Carried MDJ

Figure 22A:
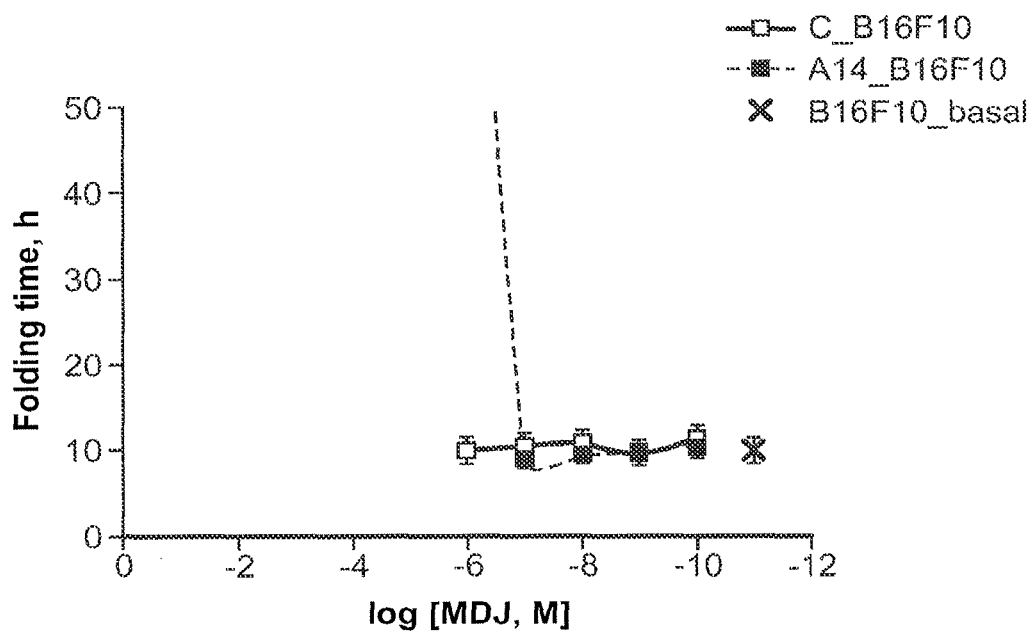
FIGS. 22A and 22B: Effect of cyclodextrin-carried MDJ on the growth of endothelial cells (HUVEC, $1 \times 10^4$ cells/well; see FIG. 22B) or murine melanoma (B16F10, $1 \times 10^4$ cells/well; see FIG. 22A) in culture plates of 96 wells. Each point represents the average of three readings performed in independent duplicates.
Figure 22B:
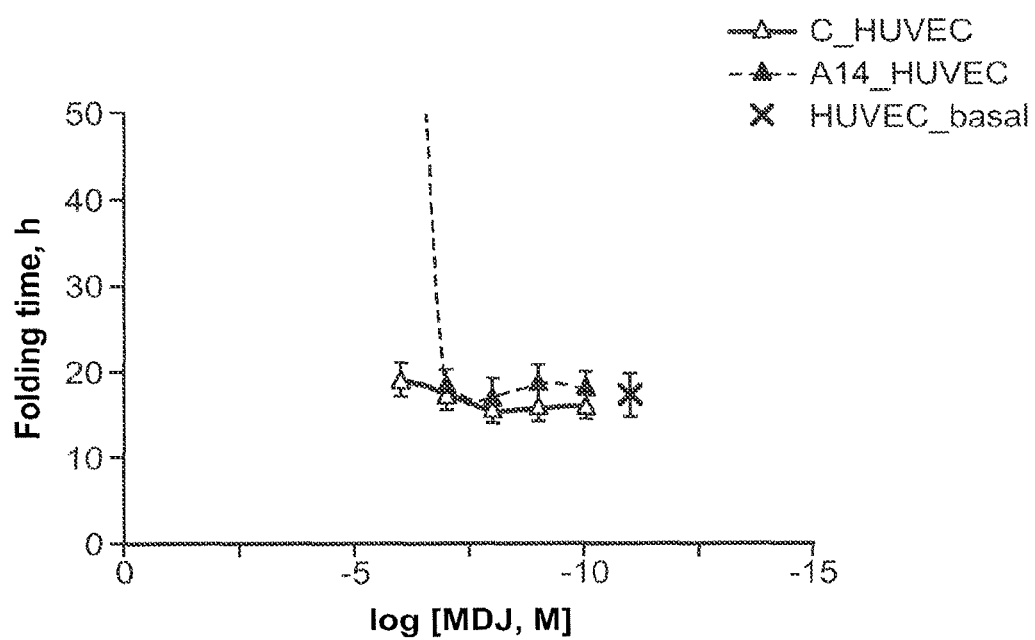
Figure 23A:
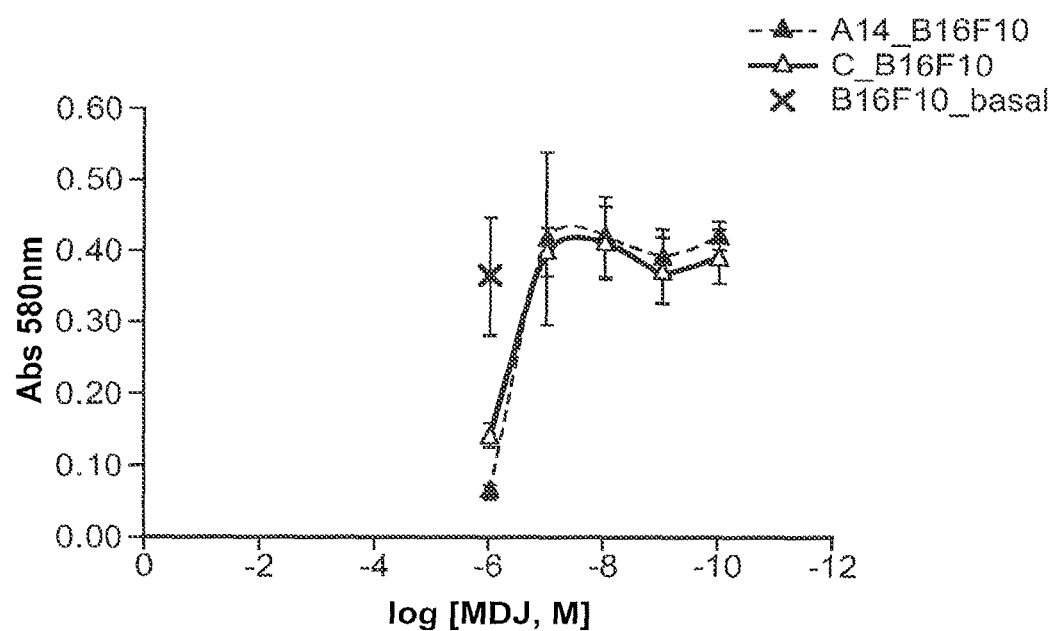
FIGS. 23A and 23B: Effect of cyclodextrin-carried MDJ on the viability of endothelial cells (HUVEC, $1 \times 10^4$ cells/well; see FIG. 23B) or murine melanoma (B16F10, $1 \times 10^4$ cells/well; see FIG. 23A) in culture plates of 96 wells after 24 h exposure, measured by MTT test. Each point represents the average of three readings performed in independent duplicates.
Figure 23B:
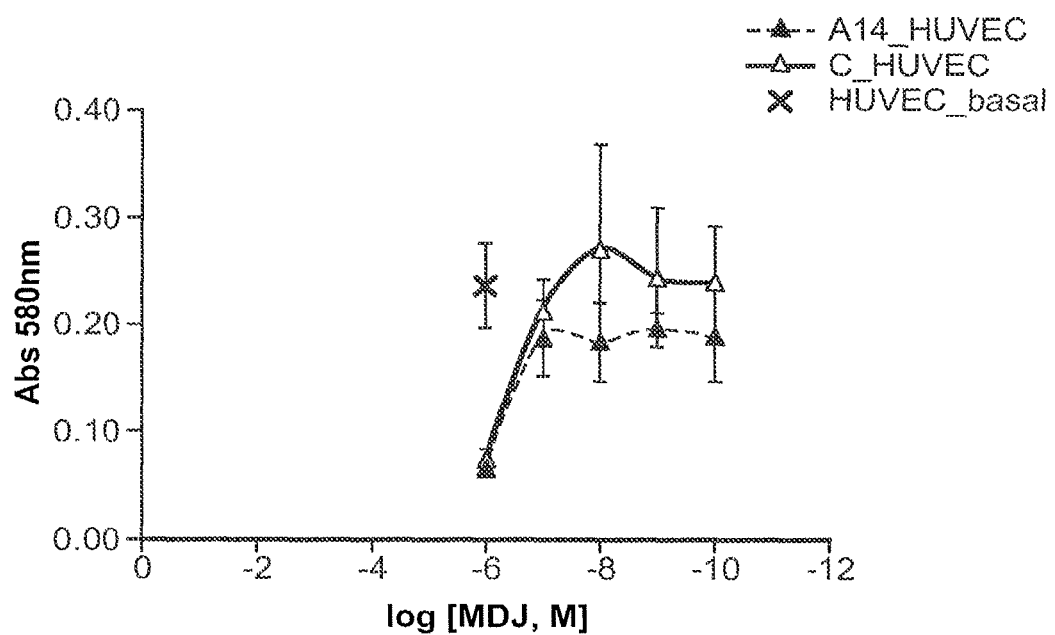

Tests on the cyclodextrin-carried MDJ in vitro demonstrated that the cytotoxicity of the active compound to HUVEC and B16F10 was preserved, occurring in much lower doses (FIG. 22). The vehicle was inert at concentrations equivalent to those used in the formulation. cyclodextrin-carried MDJ was also tested with ME1001 human cancer cell lines and tissues. Similar cytotoxicity was observed.

The cyclodextrin-carried MDJ was then tested in vivo model. The first study confirmed a reduction of doses of the active substance on the vascular structure, and a protective effect in the presence of melanoma.

Example 7: In Vitro Anti-Cell Growth Assay and In Vivo Anti-Angiogenesis Experiment with Liposome-Carried MDJ of Example 2

Figure 26:
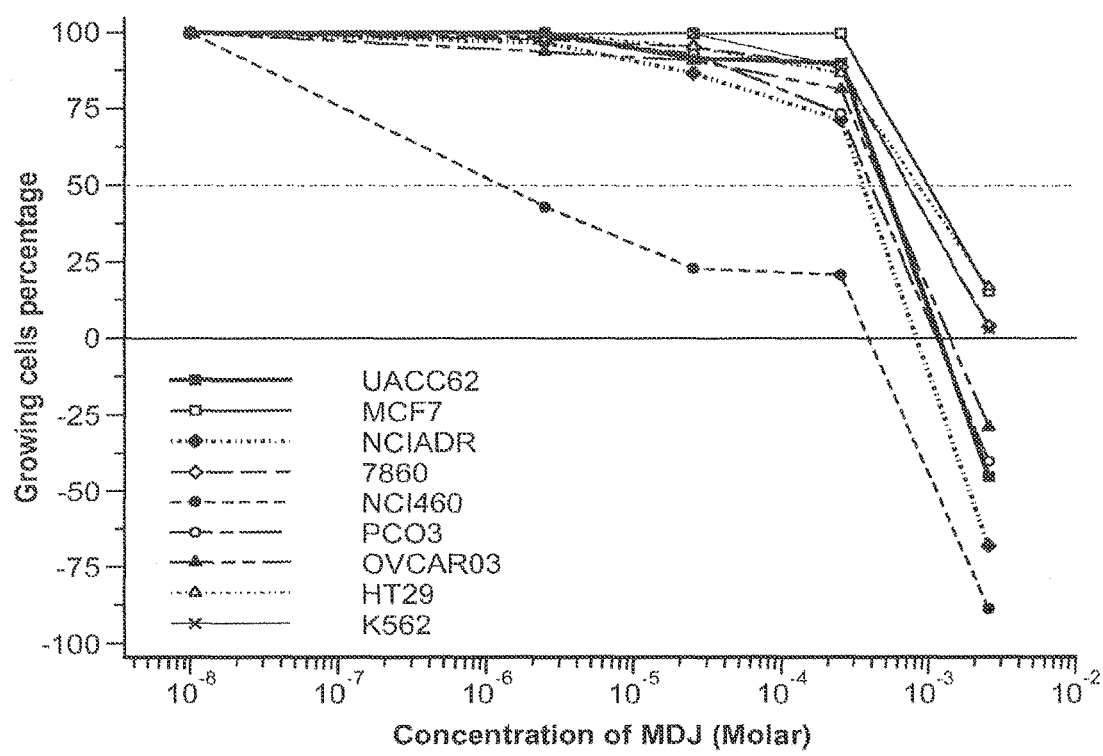
FIG. 26: Effect of the CD-carried MDJ (with size ranging from 3-30 nm) on nine cancer cell lines: UACC62, MCF7, NCIADR, 7860, NC1460, PCO3, OVCAR03, and HT29, K562. X-axis is the concentration of MDJ based on the total volume of the sample; concentration of MDJ in the nanoemulsion used was 1 millimolar.
Figure 27:
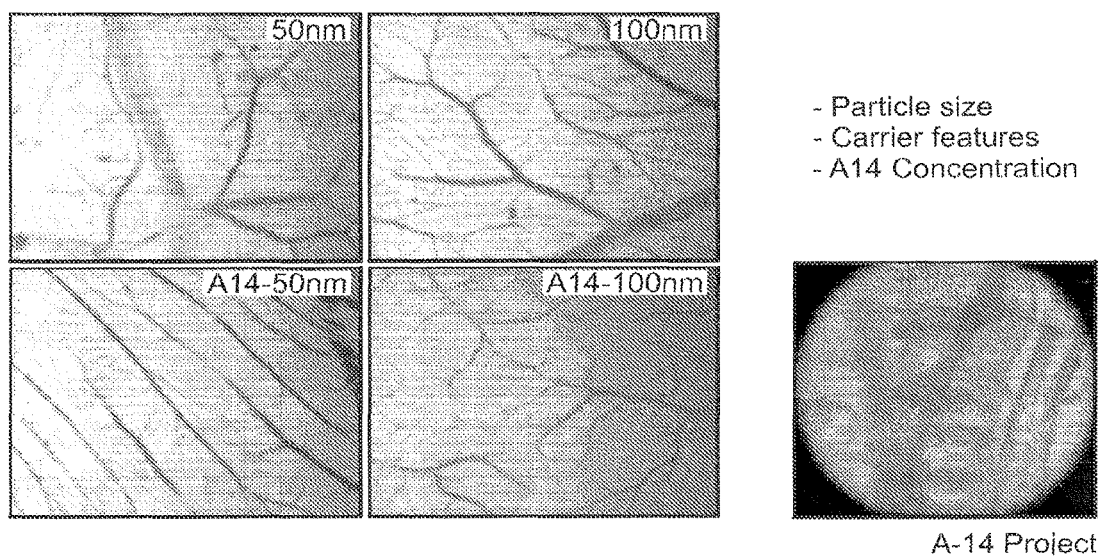
FIG. 27: Size Effect of nanocarriers on angiogenesis activity; concentration of nanocarried-MDJ used being from 1 nM to 10-100 micromolar.

The liposome-carried MDJ prepared in Example 2 were tested in nine cancer cell lines: UACC62—melanoma, MCF7—cancer resistance, NCIADR—multiple drug resistant breast cancer, 7860—kidney cancer, NC1460—lung cancer, PCO3—prostrate cancer resistance, OVCAR03—ovary Cancer, HT29—Colon Cancer, K562—leukemia. These cell lines were treated with the nanoemulsion made in Example 2 with various concentrations of MDJ. As shown in FIG. 26, the CD-carried MDJ inhibited tumor growth in a dose-dependent fashion. FIG. 27 shows the size effect of the nanocarrier on anti-angiogenesis activities in vivo. More specifically, the nanoemulsion with 100-nm nanocarriers exhibited better activity than the nanoemulsion with 50-nm nanocarriers.

Figure 28:
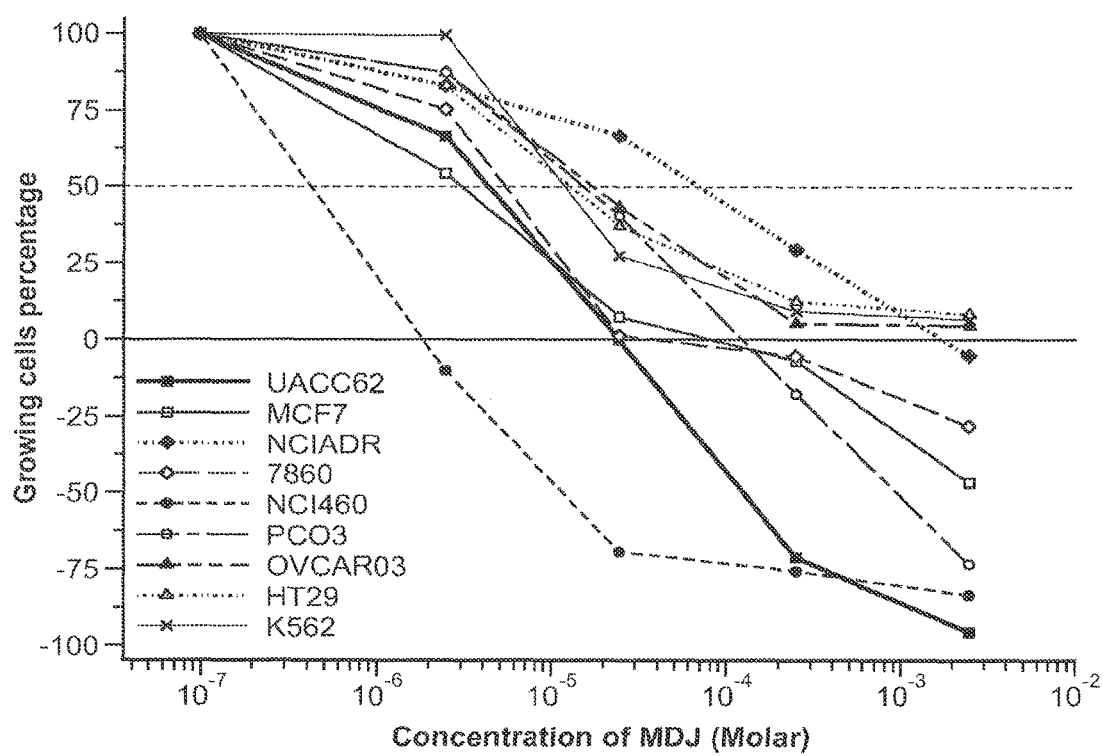
FIG. 28: Effect of the soy phosphatidylcholine liposome-carried MDJ (liposome with 50-120 nm in size) on nine cancer cell lines: UACC62, MCF7, NCIADR, 7860, NC1460, PCO3, OVCAR03, and HT29, K562. X-axis is the concentration of MDJ based on the total volume of the sample; concentration of MDJ in the nanoemulsion used was 1 millimolar.
Figure 29:
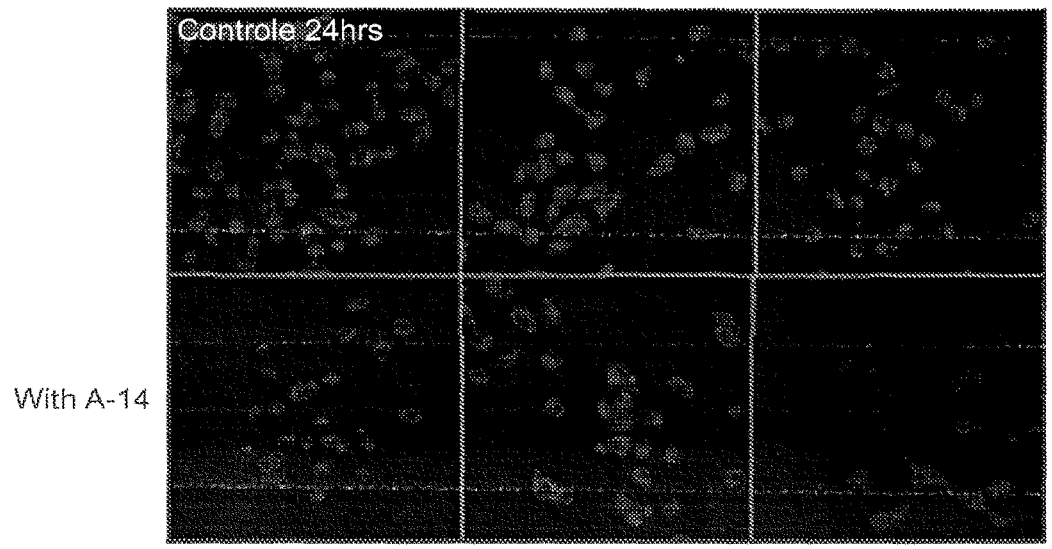
FIG. 29: Effect of MDJ-soy phosphatidyl liposome nanocarrier complex on the mitochondrial activity of UACC-62 cells after 8 h of incubation of those cells with the complex (the three bottom panels), as measured by Mitotracker red fluorescence confocal microscopy). The MDJ concentration was $10^{-3}$ M and the size of the complex ranged from 25 nm to 200 nm.
Figure 30:
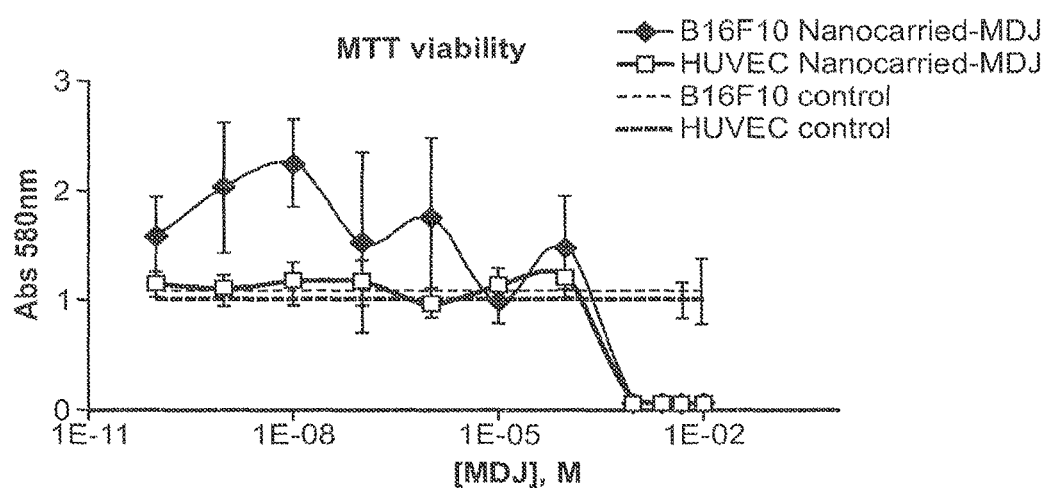
FIG. 30: Effect of MDJ-soy phosphatidyl liposome nanocarrier complex on the viability of endothelial cells (HUVEC) or murine melanoma (B16F10) after 24 h exposure, measured by MTT test.
Figure 31:
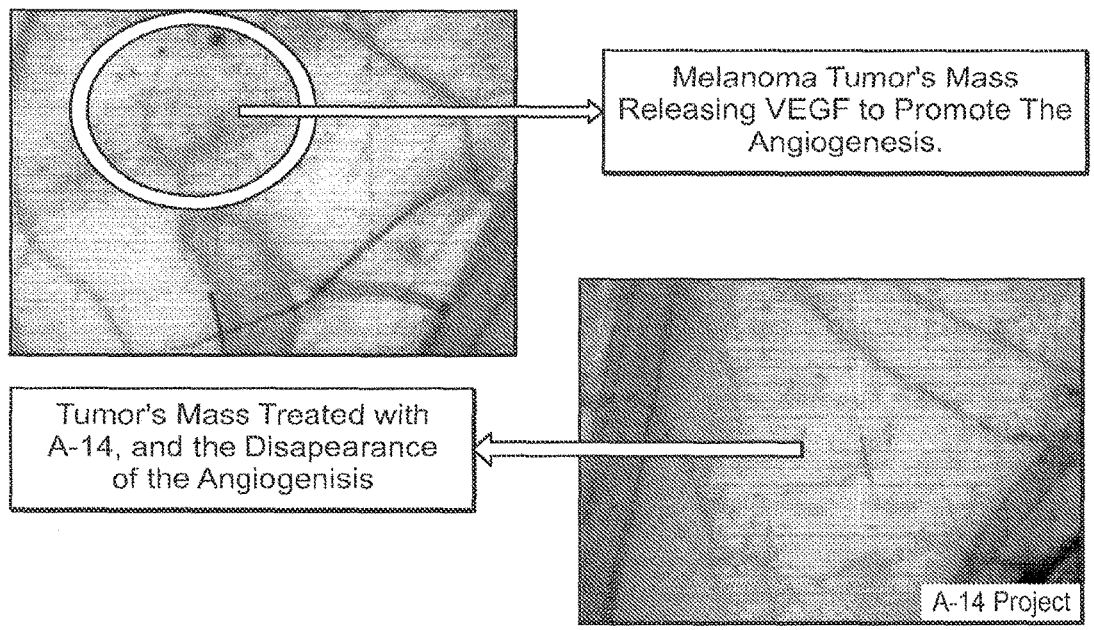
FIG. 31: Anti-angiogenesis effect of MDJ-PAMAM nanocarrier complex, with a concentration of MDJ being $10^{-3}$ M in the nanoemulsion. The top panel showed clearly the tumor mass formation of murine melanoma (B16F10) and the formation of a new vascular web to provide nutrition in order to make the tumor to grow while as shown in the bottom panel, no vascular web was formed upon treatment with the complex.
Figure 32:
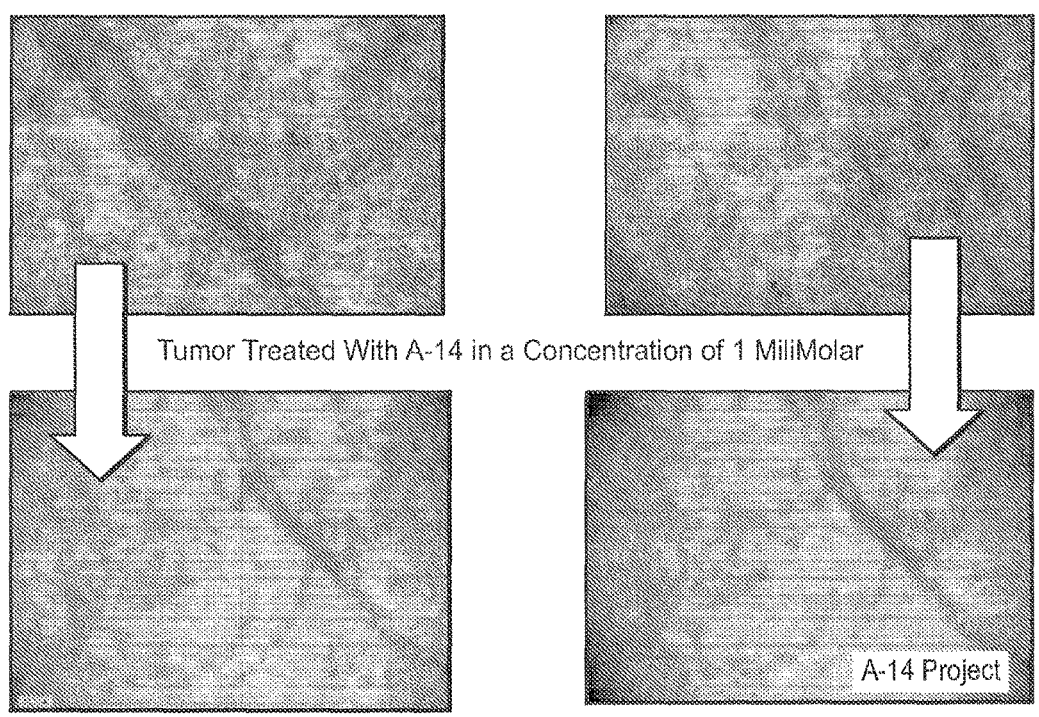
FIG. 32: Anti-angiogenesis effect of MDJ-LDE nanocarrier complex on UACC-62 cells, with a concentration of MDJ being $10^{-3}$ M in the sample.
Figure 33:
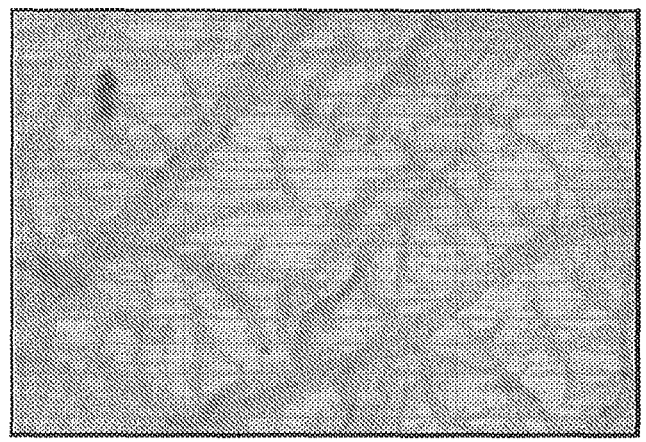
FIG. 33: Anti-angiogenesis effect of MDJ-soy phosphatidylcholine liposome nanocarrier complex on UACC-62 cells, with a concentration of MDJ being $10^{-4}$ M in the sample.
Figure 33:
Figure 34A:
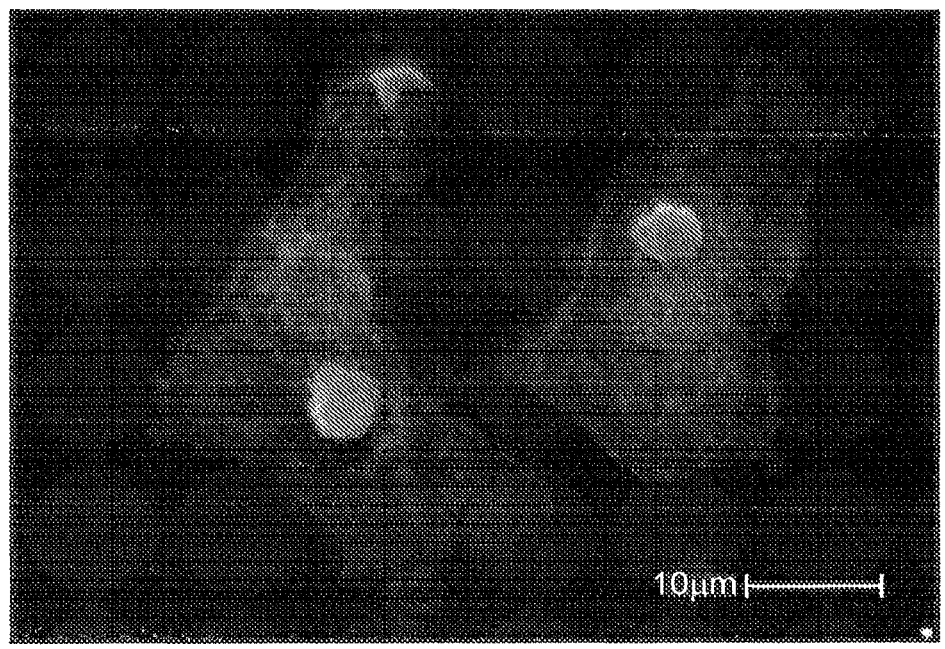
FIGS. 34A and 34B: Effect of macrophage-activated by in MDJ-LDE microcarrier complex (10 micron in size, a concentration of MDJ being $10^{-3}$ to $10^{-1}$ M) on Leukemia cells.
Figure 34B:
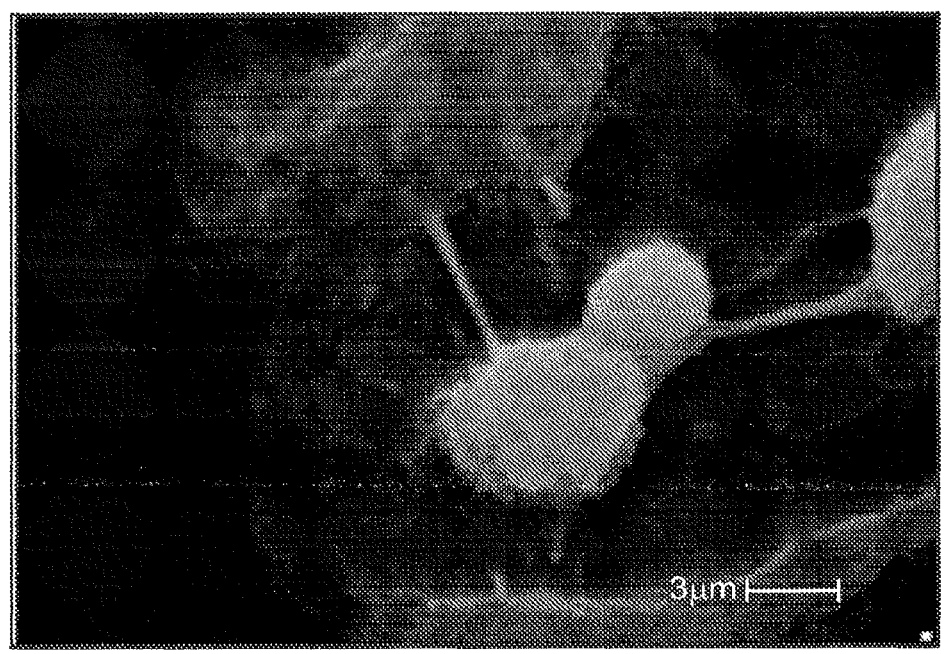
Figure 35:
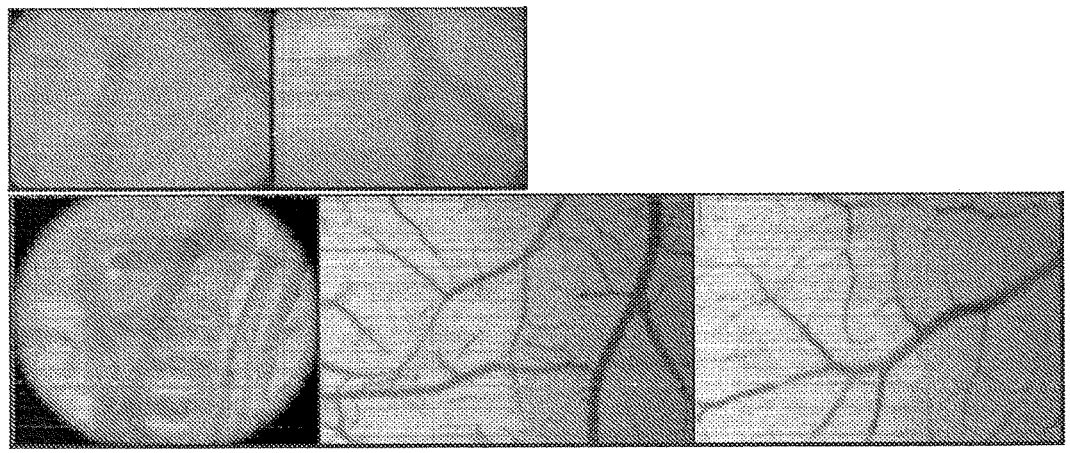
FIG. 35: In vivo angiogenesis effect of nanocarried-MDJ at low doses: the concentrations of MDJ being 10 μM in the top two images and 100 nM in the bottom three images.
Figure 36A:
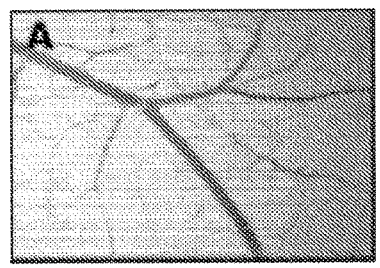
FIGS. 36A-36D: In vivo angiogenesis effect of MDJ and nanocarried-MDJ at a concentration of 30 μM (FIG. 36A: untreated.
Figure 36B:
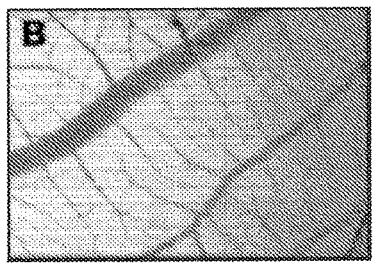
Figure 36C:
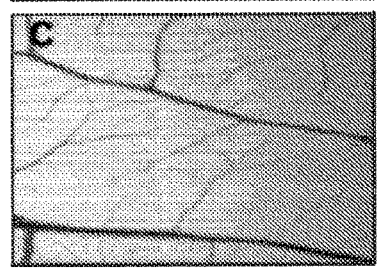
Figure 36D:
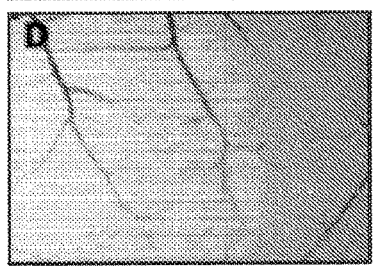

Further, as demonstrated by FIG. 28, the liposome-carried MDJ showed enhanced anti-cell growth activity when the size of the liposomes was less than 100 nm.

Example 8: In Vitro Anti-Cell Growth Assay

[This Example is Based on the Manuscript Describing the Harvard Studies]

The nanocarried MDJ (where the nanocarriers were CD, liposome, or LDE) were tested in the following 11 cell lines (3 leukemias, 2 Breast cancers, 1 Macrophage and 5 Prostrate Cancer) were purchased from the American Type Culture Collection (ATCC). The cells were grown in respective growth medium suggested by the ATCC (RPMI-1640, DMEM, EMEM or F12-k medium supplemented with 10% fetal bovine serum and penicillin/streptomycin. The details of the cell lines are presented in the Table 4 below.

TABLE 4

| Name of cell Line | Cell line Description |
|---|---|
| DU-145 | Human Prostrate Cancer |
| CRL-2505 | Human Prostrate Cancer |
| CRL-1740 | Human Prostrate Cancer |

TABLE 4-continued

| Name of cell Line | Cell line Description |
|---|---|
| DU-145 (HTB-81) | Human Prostate Cancer |
| PC-3 (CRL-1435) | Human Prostate Cancer |
| MCF-7 (HTB-22) | Human Breast Cancer |
| CRL-2314 | Human Breast Cancer |
| Nomo-1 | Human Acute myeloid Leukemia |
| MOLM-14 | Human Acute myeloid Leukemia |
| TIB-152 | Human Acute lymphoblastic Leukemia |
| Macrophage | Human Phagocytic cells |

The nanocarried MDJ formulation was dissolved in Milli-Q water and stored at room temperature. Before the usage, the formulation was purified using a 0.22 micron filter to avoid contamination.

Three million cells from each cell line were distributed equally into three wells of a 6-well plate and were grown overnight. The following day, the nanocarried MDJ formulation containing 1 μM of MDJ was added into one well, whereas the same concentration of empty nanocarriers (or nanoparticles) was added in the second well, and the third well carrying cells was kept intact with no drug or empty nanocarriers ("control"). The apoptotic effect of the formulation was observed at 6 hrs, 12 hrs and 24 hrs following the treatment under an inverted microscope.

Figure 38A:
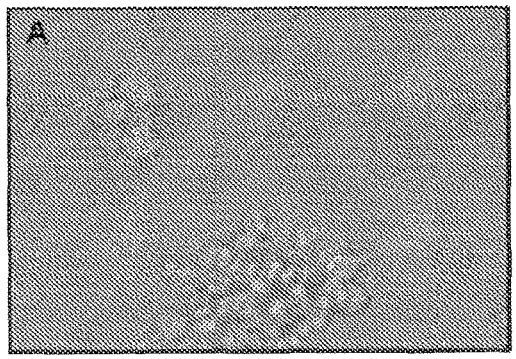
Figure 38B:
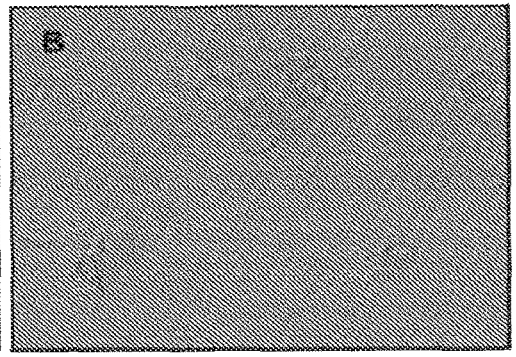
Figure 38C:
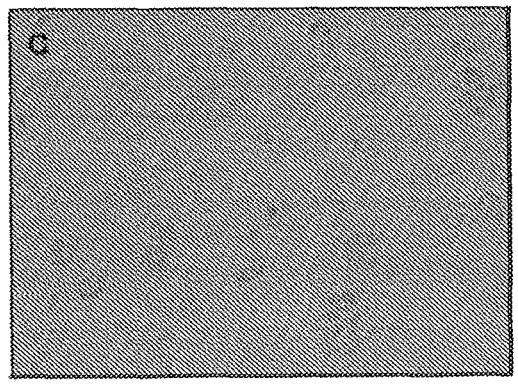
Figure 39A:
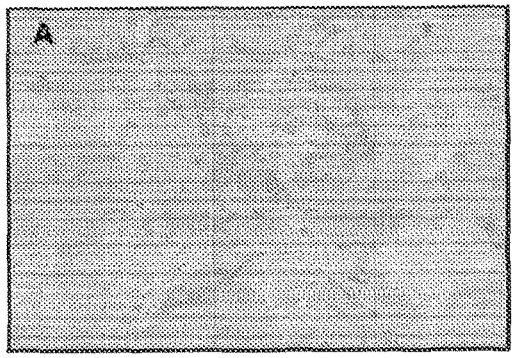
Figure 39B:
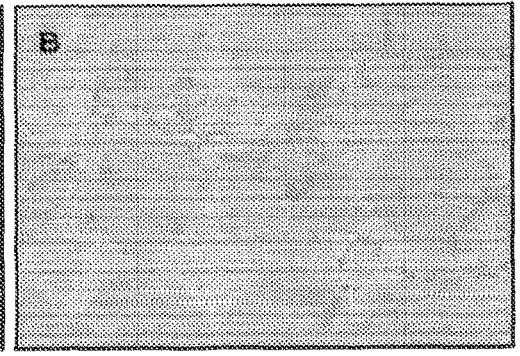
Figure 39C:
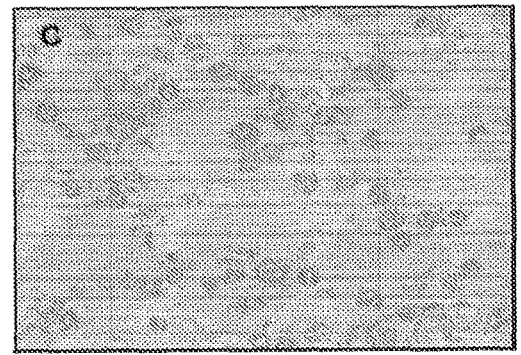
Figure 40A:
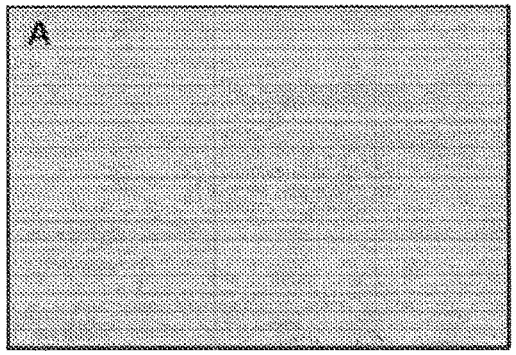
Figure 40B:
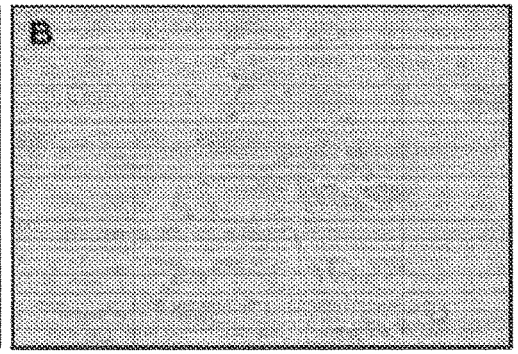
Figure 40C:
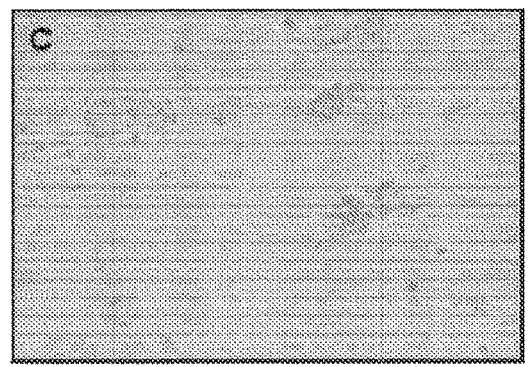
Figure 41A:
Figure 41B:
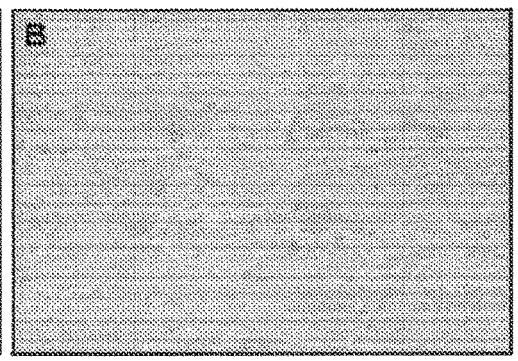
Figure 41C:
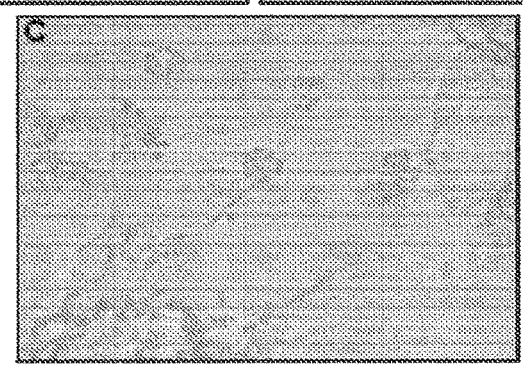
Figure 43:
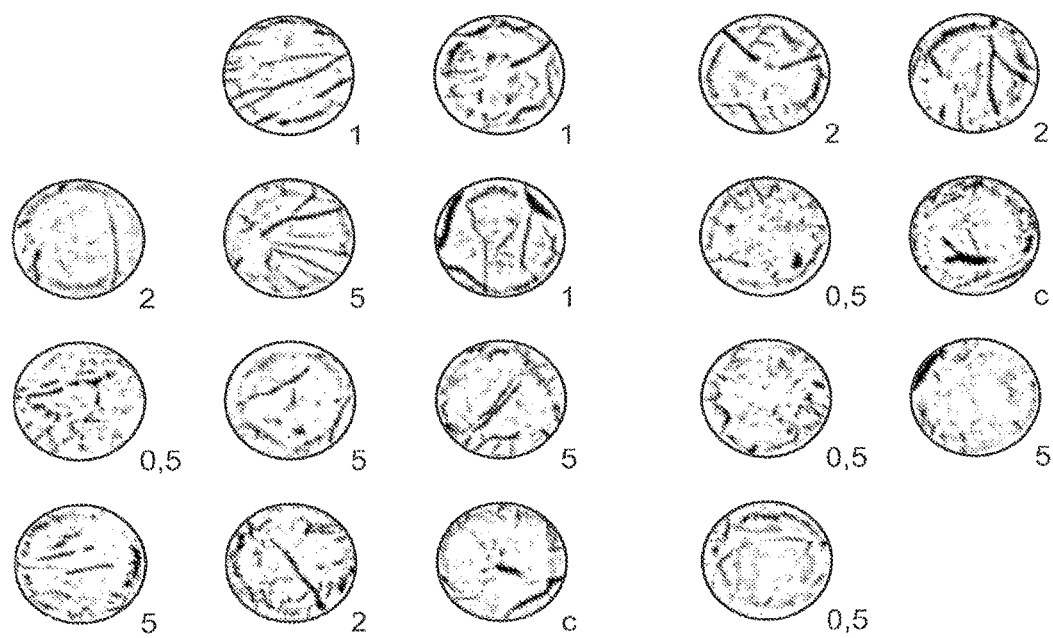
FIG. 43: Images showing the fragmentation of the vessels when contacted with the A-14 bound with zinc, calcium or amino acids. Zinc-bound A-14 demonstrated the most significant effect on vessel fragmentation compared to calcium- or amino acid-bound A-14. 1: A-14 with alanine; 2: A-14 with argentine; 0.5: A-14 with zinc; 5: A-14 with calcium and c: control. The carrier is liposome.
Figure 44A:
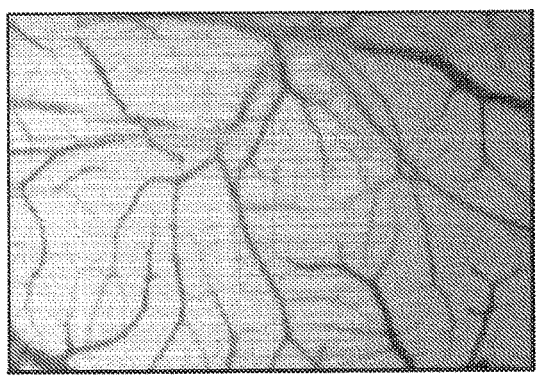
FIGS. 44A and 44B.
Figure 44B:
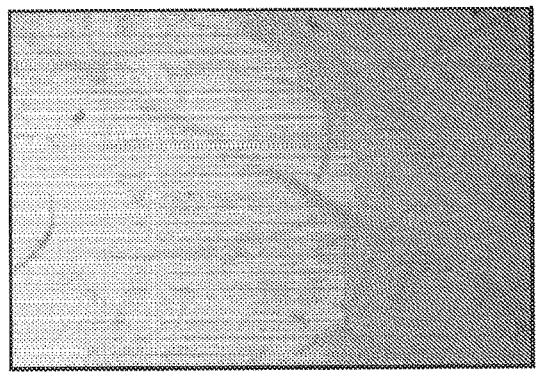
Figure 45:
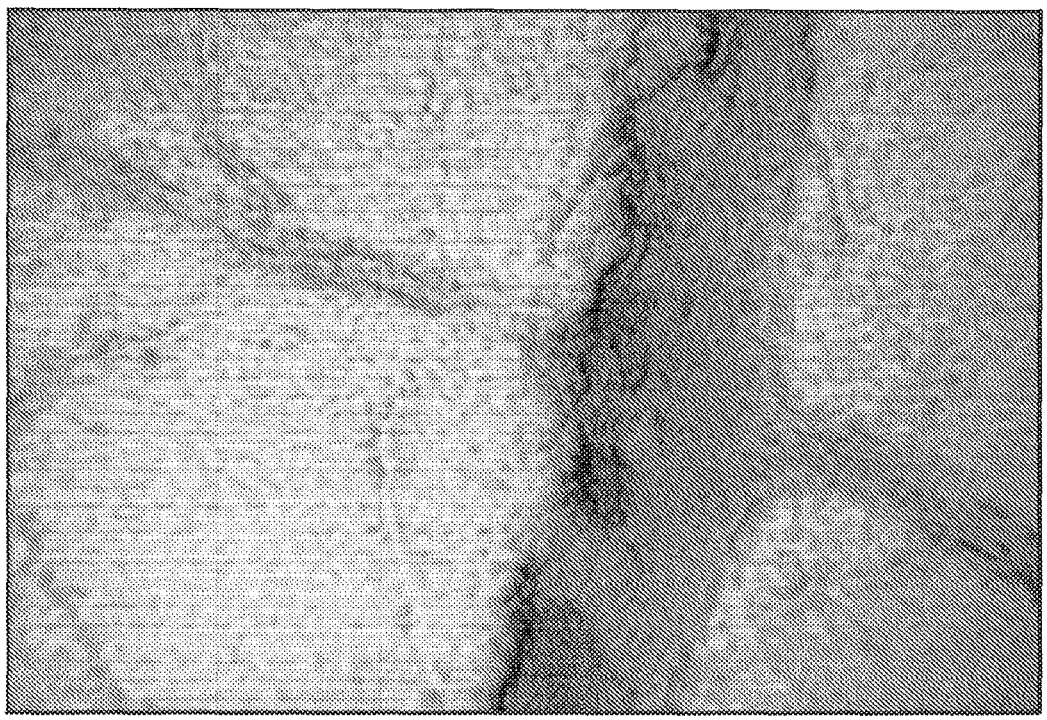
FIG. 45: Image showing destruction of the endothelial cells by amino acid-bound A-14. The carrier is liposome.
Figure 46:
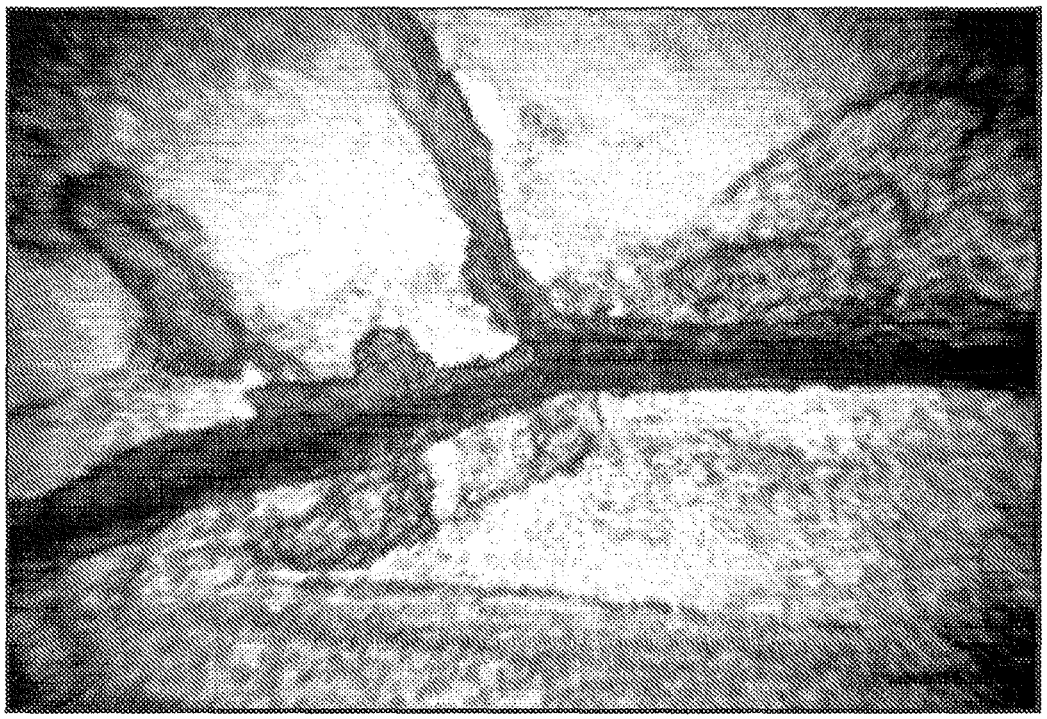
FIG. 46: Image showing the anti-angiogenesis effect around the vessels in breast cancer by zinc-bound A-14. The carrier is liposome.

The nanocarried MDJ showed a great effect of the apoptosis phenomenon in the cancer cell lines that were tested. Apoptosis effect was observed in every tested cell line, starting after 6 hours of the MDJ treatment and reached the peak after 24 hours. Some cancer cell lines, such as TIB-512, CRL-2876, and CRL-2314, were completely or nearly completely dead after 24 hours (see FIGS. 38-40) while the others showed an average of 60% to 70% cell death (see FIG. 41). The rest of the cells were in pre-apoptotic stage. The molecule had its action targeting only cancer cells, suggesting nano-carriers as an effective drug delivery agent into the cancer cells. The control cells which had just empty nanoparticles showed very little to no apoptosis.

Cancer cells have different ways of producing energy compared to healthy cells, which is also known as Warburg Hypothesis. In this hypothesis, the mitochondrion which produces the energy for cancer cells uses a non-oxidative pathway instead of oxidative pathway used by healthy cells. It has been reported that MJ targets this anomaly in mitochondria in cancer cells and provokes the release of the cytochrome C as well as other proteases and caspases. The MJ was capable to induce the swelling in mitochondria isolated from Hep 3B hepatomas cells, but not in mitochondria isolated from 3T3 non transformed cells or from normal lymphocytes. The release of cytochrome C leads to mitochondrial membrane permeability transition, membrane depolarization, osmotic swelling and thus leading to apoptosis. Macrophage cell line as listed in Table 4 was used in this study as non-transformed cells, where no effect of apoptosis was widely observed (see FIG. 42).

Studies conducted by the applicant have suggested that nanocarried MDJ exerts its cytotoxic effects independent of transcription, translation and p53 (unpublished). Previous studies (unpublished) of MDJ alone showed similar results in vitro but the drug degraded very quickly in vivo and needed very high doses to see an effect. By encapsulating the molecule in nanoparticles, it was shown that MDJ didn't degrade in vivo and was highly effective in treatment of cancer cells with a very low dose, for example, 1000 times less than what was used with the naked molecule.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

I claim:

1. A pharmaceutical composition comprising a pharmaceutically acceptable solvent and a plurality of nanocarriers or microcarriers that contain a jasmonate compound, wherein
   the nanocarriers or microcarriers are formed of an α, β, or γ cyclodextrin;
   the nanocarriers have a size ranging from 1 nanometer (nm) to 900 nm; or
   the microcarriers have a size ranging from 1 micron to 50 micron; and
   the pharmaceutical composition has a concentration of the jasmonate compound ranging from 1 nM to 1 M.

2. The pharmaceutical composition of claim 1, wherein the jasmonate compound is selected from the group consisting of jasmonic acid, 7-iso-jasmonic acid, 9,10-dihydro-jasmonic acid, 9,10-dihydro-isojasmonic acid, 2,3-didehydrojasmonic acid, 3,4-didehydrojasmonic acid, 3,7-didehydrojasmonic acid, 4,5-didehydrojasmonic acid, 4,5-didehydro-7-isojasmonic acid, cucurbic acid, 6-epi-cucurbic acid, 6-epi-cucurbic acid-lactone, 12-hydroxy-jasmonic acid, 12-hydroxy-jasmonic acid-lactone, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, tuberonic acid-O-β-glucopyranoside, cucurbic acid-O-β-glucopyranoside, 5,6-didehydro-jasmonic acid, 6,7-didehydro-jasmonic acid, 7,8-didehydro-jasmonic acid, cis-jasmone, dihydrojasmone, and a lower alkyl ester thereof.

3. The pharmaceutical composition of claim 1, wherein the jasmonate compound is methyl jasmonate and has a concentration of about 1 nM to 1 μM.

4. The pharmaceutical composition of claim 1, wherein the jasmonate compound is methyl jasmonate and has a concentration of about 1 μM to 100 mM.

5. The pharmaceutical composition of claim 1, wherein the nanocarriers or microcarriers further contain a non-jasmonate compound.

6. The pharmaceutical composition of claim 1, wherein the jasmonate compound is methyl dihydrojasmonate jasmonate.

7. The pharmaceutical composition of claim 1, wherein the nanocarriers are formed of a cyclodextrin and have a size ranging from 3 nm to 100 nm.

8. The pharmaceutical composition of claim 7, wherein the cyclodextrin nanocarriers have a size ranging from 3.5 nm to 11 nm.

9. The pharmaceutical composition of claim 7, wherein the cyclodextrin nanocarriers have a size ranging from 50 nm to 100 nm.

10. The pharmaceutical composition of claim 1, wherein the nanocarriers or microcarriers further contain 2-aminoethyl dihydrogen phosphate, 3,7-dimethyl-2,6-octadienal, methyl salicylate, or abscisic acid.

11. The pharmaceutical composition of claim 1, wherein the pharmaceutically acceptable solvent is water, an alcohol, or a mixture thereof.

* * * * *